US012250943B2

(12) United States Patent
Refaeli et al.

(10) Patent No.: US 12,250,943 B2
(45) Date of Patent: Mar. 18, 2025

(54) COMPOSITIONS AND METHODS FOR THE CRYOPRESERVATION OF IMMUNE CELLS

(71) Applicant: HTYR Acquistion LLC, Philadelphia, PA (US)

(72) Inventors: Yosef Refaeli, Denver, CO (US); Brian C. Turner, Denver, CO (US); Thomas R. Payne, Aurora, CO (US)

(73) Assignee: HTYR Acquisition LLC, Philadelphia, PA (US)

( * ) Notice: Subject to any disclaimer, the term of this patent is extended or adjusted under 35 U.S.C. 154(b) by 729 days.

(21) Appl. No.: 17/602,207

(22) PCT Filed: Apr. 7, 2020

(86) PCT No.: PCT/US2020/027070
§ 371 (c)(1),
(2) Date: Oct. 7, 2021

(87) PCT Pub. No.: WO2020/210231
PCT Pub. Date: Oct. 15, 2020

(65) Prior Publication Data
US 2022/0142149 A1  May 12, 2022

Related U.S. Application Data

(60) Provisional application No. 62/830,950, filed on Apr. 8, 2019.

(51) Int. Cl.
*A01N 1/02* (2006.01)
*C12N 5/078* (2010.01)

(52) U.S. Cl.
CPC ......... *A01N 1/0221* (2013.01); *A01N 1/0284* (2013.01); *C12N 5/0634* (2013.01)

(58) Field of Classification Search
None
See application file for complete search history.

(56) References Cited

U.S. PATENT DOCUMENTS

| | | |
|---|---|---|
| 4,900,322 A | 2/1990 | Adams |
| 4,963,489 A | 10/1990 | Naughton et al. |
| 5,289,858 A | 3/1994 | Grabenkort |
| 5,476,996 A | 12/1995 | Wilson et al. |
| 5,652,122 A | 7/1997 | Frankel et al. |
| 5,670,617 A | 9/1997 | Frankel et al. |
| 5,674,980 A | 10/1997 | Frankel et al. |
| 5,698,767 A | 12/1997 | Wilson et al. |
| 5,747,641 A | 5/1998 | Frankel et al. |
| 5,804,604 A | 9/1998 | Frankel et al. |
| 5,811,301 A | 9/1998 | Cameron |
| 5,824,837 A | 10/1998 | Chen et al. |
| 5,843,728 A | 12/1998 | Seed et al. |
| 5,847,082 A | 12/1998 | Rother et al. |
| 5,849,288 A | 12/1998 | Reisner |
| 5,851,828 A | 12/1998 | Seed et al. |
| 5,912,170 A | 6/1999 | Seed et al. |
| 6,004,811 A | 12/1999 | Seed et al. |
| 6,040,177 A | 3/2000 | Riddell et al. |
| 6,284,240 B1 | 9/2001 | Seed et al. |
| 6,358,739 B1 | 3/2002 | Baetge et al. |
| 6,392,013 B1 | 5/2002 | Seed et al. |
| 6,410,014 B1 | 6/2002 | Seed et al. |
| 6,451,558 B1 | 9/2002 | Cooke et al. |
| 6,451,601 B1 | 9/2002 | Baetge et al. |
| 6,645,501 B2 | 11/2003 | Dowdy |
| 6,753,162 B1 | 6/2004 | Seed et al. |
| 7,135,287 B1 | 11/2006 | Lonberg et al. |
| 7,311,920 B1 | 12/2007 | Devico et al. |
| 7,582,745 B2 | 9/2009 | Sah et al. |
| 7,767,453 B2 | 8/2010 | Zhang |
| 8,034,334 B2 | 10/2011 | Dudley et al. |
| 8,211,422 B2 | 7/2012 | Eshhar et al. |
| 8,481,492 B2 | 7/2013 | Edenhofer et al. |
| 8,637,307 B2 | 1/2014 | June et al. |
| 8,697,854 B2 | 4/2014 | Schendel et al. |
| 8,784,825 B2 | 7/2014 | Refaeli et al. |
| 8,828,723 B2 | 9/2014 | Refaeli et al. |
| 8,986,702 B2 | 3/2015 | Refaeli et al. |
| 9,150,831 B2 | 10/2015 | Cambier et al. |
| 9,169,462 B2 | 10/2015 | Refaeli et al. |
| 9,365,825 B2 | 6/2016 | Turner et al. |
| 9,775,897 B2 | 10/2017 | Refaeli et al. |
| 9,789,135 B2 | 10/2017 | Turner et al. |

(Continued)

FOREIGN PATENT DOCUMENTS

| | | |
|---|---|---|
| AU | 2762802 A1 | 5/2002 |
| AU | 2006304392 A1 | 4/2007 |

(Continued)

OTHER PUBLICATIONS

De Clercq, E., "New Nucleotide Analogues for the Treatment of Hemorrhagic Fever Virus Infections." Chem. Asian J., 2019, vol. 14, pp. 3962-3968.
Duraffour, et al., "How to treat Ebola virus infections? A lesson from the field." Current Opinion in Virology, 2017, vol. 24, pp. 9-15.
Fanale, et al., "Monoclonal Antibodies in the Treatment of Non-Hodgkin's Lymphoma." Drugs, 2007, vol. 3, pp. 333-350.
Foreign Action other than Search Report on CN 201910023181.2 Dtd Sep. 15, 2022.
Foreign Action other than Search Report on CN 201910848417.6 Dtd Nov. 3, 2022, 15 pages.
Foreign Action other than Search Report on EP 20212922.7 Dtd Sep. 1, 2022.
Gibson, et al., "How we evaluate and treat neutropenia in adults." Blood, 2014, vol. 124, No. 8, pp. 1251-1258.

(Continued)

*Primary Examiner* — Blaine Lankford
(74) *Attorney, Agent, or Firm* — Fox Rothschild LLP

(57) ABSTRACT

Provided herein are compositions and methods for the cryopreservation of immune cells, such as peripheral blood mononuclear cells (PBMCs) by pre-treating the cells with a PTD-MYC fusion protein (e.g., an HIV TAT-MYC fusion protein) prior to freezing. Kits for practicing the methods are also provided herein.

24 Claims, 5 Drawing Sheets

Specification includes a Sequence Listing.

(56) References Cited

U.S. PATENT DOCUMENTS

| | | | |
|---|---|---|---|
| 10,087,420 | B2 | 10/2018 | Turner et al. |
| 10,149,898 | B2 | 12/2018 | Refaeli et al. |
| 10,442,853 | B2 | 10/2019 | Refaeli et al. |
| 10,760,055 | B2 | 9/2020 | Cambier et al. |
| 10,864,259 | B2 | 12/2020 | Refaeli et al. |
| 11,116,796 | B2 | 9/2021 | Turner et al. |
| 11,369,678 | B2 | 6/2022 | Refaeli et al. |
| 2001/0049393 | A1 | 12/2001 | Coller et al. |
| 2002/0055478 | A1 | 5/2002 | Faris et al. |
| 2002/0076787 | A1 | 6/2002 | Baetge et al. |
| 2002/0098166 | A1 | 7/2002 | Havemann et al. |
| 2002/0155502 | A1 | 10/2002 | Balint et al. |
| 2003/0072794 | A1 | 4/2003 | Boulikas |
| 2003/0138859 | A1 | 7/2003 | Barbera-Guillem et al. |
| 2003/0220286 | A1 | 11/2003 | Abruzzese et al. |
| 2004/0224402 | A1 | 11/2004 | Bonyhadi et al. |
| 2005/0220705 | A1 | 10/2005 | Brooks et al. |
| 2005/0281816 | A1 | 12/2005 | Lamping et al. |
| 2006/0068369 | A1 | 3/2006 | Coelho et al. |
| 2006/0068469 | A1 | 3/2006 | Payne et al. |
| 2006/0115898 | A1 | 6/2006 | Zhang et al. |
| 2006/0154331 | A1 | 7/2006 | Avidan et al. |
| 2006/0156422 | A1 | 7/2006 | Dalrymple et al. |
| 2006/0222657 | A1 | 10/2006 | Dowdy et al. |
| 2007/0011753 | A1 | 1/2007 | Ito et al. |
| 2007/0047583 | A1 | 3/2007 | Assa et al. |
| 2007/0067854 | A1 | 3/2007 | Habu et al. |
| 2007/0082397 | A1 | 4/2007 | Hasson et al. |
| 2007/0093420 | A1 | 4/2007 | Yeomans et al. |
| 2007/0098715 | A1 | 5/2007 | Ettenberg et al. |
| 2007/0116691 | A1 | 5/2007 | Cambier et al. |
| 2007/0130628 | A1 | 6/2007 | Brown |
| 2007/0248618 | A1 | 10/2007 | Cohen |
| 2008/0050396 | A1 | 2/2008 | Andersen et al. |
| 2009/0291094 | A1 | 11/2009 | Refaeli et al. |
| 2010/0047217 | A1 | 2/2010 | Refaeli et al. |
| 2010/0055129 | A1 | 3/2010 | Refaeli et al. |
| 2010/0233804 | A1 | 9/2010 | Zhou et al. |
| 2010/0279351 | A1 | 11/2010 | Refaeli |
| 2010/0297763 | A1 | 11/2010 | Cambier et al. |
| 2011/0218210 | A1 | 9/2011 | Refaeli et al. |
| 2012/0003189 | A1 | 1/2012 | Pelus et al. |
| 2012/0027792 | A1 | 2/2012 | Pavlakis et al. |
| 2012/0244133 | A1 | 9/2012 | Rosenberg et al. |
| 2012/0251563 | A1 | 10/2012 | Nicchitta et al. |
| 2013/0177586 | A1 | 7/2013 | Refaeli et al. |
| 2014/0109246 | A1 | 4/2014 | Jimeno et al. |
| 2014/0255369 | A1 | 9/2014 | Turner et al. |
| 2014/0356392 | A1* | 12/2014 | Refaeli ............... C07K 14/47 435/375 |
| 2015/0164950 | A1 | 6/2015 | Turner et al. |
| 2015/0218515 | A1 | 8/2015 | Altrichter et al. |
| 2017/0044500 | A1 | 2/2017 | Cooper et al. |
| 2018/0036396 | A1* | 2/2018 | Refaeli ............ A61K 2239/57 |
| 2019/0060434 | A1 | 2/2019 | Refaeli et al. |
| 2020/0215188 | A1 | 7/2020 | Refaeli et al. |
| 2021/0121550 | A1 | 4/2021 | Refaeli et al. |

FOREIGN PATENT DOCUMENTS

| | | | |
|---|---|---|---|
| CA | 2584738 | A1 | 4/2006 |
| CA | 2626525 | A1 | 4/2007 |
| CN | 1206044 | | 1/1999 |
| CN | 1357620 | A | 7/2002 |
| CN | 1659187 | | 8/2005 |
| CN | 101045914 | A | 10/2007 |
| CN | 101330830 | A | 12/2008 |
| CN | 102027105 | A | 4/2011 |
| CN | 102083960 | A | 6/2011 |
| CN | 102083970 | | 6/2011 |
| CN | 103998604 | | 8/2014 |
| CN | 104353066 | A | 2/2015 |
| CN | 104640551 | | 5/2015 |
| EP | 0 367 76 | A2 | 9/1981 |
| EP | 0 213 469 | A2 | 3/1987 |
| EP | 1 103 615 | A1 | 5/2001 |
| EP | 1 357 184 | | 10/2003 |
| EP | 1 792 627 | | 6/2007 |
| GB | 2 387 599 | | 10/2003 |
| JP | 2000-175692 | | 6/2000 |
| JP | 2000-189157 | | 7/2000 |
| JP | 2001-501909 | | 2/2001 |
| JP | 2001-518300 | | 10/2001 |
| JP | 2002-541786 | A | 12/2002 |
| JP | 2003-513672 | A | 4/2003 |
| JP | 2003-514565 | | 4/2003 |
| JP | 2003-265189 | | 9/2003 |
| JP | 2004-519245 | A | 7/2004 |
| JP | 2005-523012 | | 8/2005 |
| JP | 2005-525085 | | 8/2005 |
| JP | 2005-232148 | | 9/2005 |
| JP | 2005-527211 | | 9/2005 |
| JP | 2006-519781 | A | 8/2006 |
| JP | 2009-511081 | A | 3/2009 |
| JP | 2011-528567 | A | 11/2011 |
| JP | 2012-501347 | A | 1/2012 |
| JP | 2014-527980 | A | 10/2014 |
| JP | 2015-524415 | A | 8/2015 |
| JP | 6167130 | B2 | 8/2015 |
| JP | 2015-525209 | A | 9/2015 |
| JP | 2016-510996 | A | 4/2016 |
| JP | 2017-513498 | | 6/2017 |
| JP | 6484293 | B2 | 3/2019 |
| JP | 6655050 | B2 | 2/2020 |
| WO | WO-86/03780 | A1 | 7/1986 |
| WO | WO-92/15322 | | 9/1992 |
| WO | WO-94/04686 | | 3/1994 |
| WO | WO-94/19465 | | 9/1994 |
| WO | WO-95/14078 | | 5/1995 |
| WO | WO-98/10058 | | 3/1998 |
| WO | WO-98/52614 | | 11/1998 |
| WO | WO-99/16884 | | 4/1999 |
| WO | WO-99/45962 | | 9/1999 |
| WO | WO-99/53023 | | 10/1999 |
| WO | WO-99/53028 | | 10/1999 |
| WO | WO-00/09669 | | 2/2000 |
| WO | WO-00/61617 | A2 | 10/2000 |
| WO | WO-00/62067 | | 10/2000 |
| WO | WO-01/34824 | A2 | 5/2001 |
| WO | WO-01/38548 | | 5/2001 |
| WO | WO-02/057436 | | 7/2002 |
| WO | WO-02/074968 | A1 | 9/2002 |
| WO | WO-03/008630 | | 1/2003 |
| WO | WO-03/020763 | | 3/2003 |
| WO | WO-03/033701 | | 4/2003 |
| WO | WO-03/038057 | | 5/2003 |
| WO | WO-03/039462 | | 5/2003 |
| WO | WO-03/057171 | A2 | 7/2003 |
| WO | WO-03/089580 | | 10/2003 |
| WO | WO-03/089630 | | 10/2003 |
| WO | WO-03/094849 | | 11/2003 |
| WO | WO-03/097675 | | 11/2003 |
| WO | WO-2004/033685 | A1 | 4/2004 |
| WO | WO-2004/035535 | | 4/2004 |
| WO | WO-2004/044004 | A2 | 5/2004 |
| WO | WO-2004/050885 | | 6/2004 |
| WO | WO-2004/050895 | A2 | 6/2004 |
| WO | WO-2004/074322 | A1 | 9/2004 |
| WO | WO-2004/084805 | | 10/2004 |
| WO | WO-2005/014785 | | 2/2005 |
| WO | WO-2005/049073 | A2 | 6/2005 |
| WO | WO-2005/084158 | | 9/2005 |
| WO | WO-2005/113595 | A2 | 12/2005 |
| WO | WO-2005/114215 | A2 | 12/2005 |
| WO | WO-2006/000830 | A2 | 1/2006 |
| WO | WO-2006/032876 | | 3/2006 |
| WO | WO-2006/116512 | | 11/2006 |
| WO | WO-2006/125962 | A2 | 11/2006 |
| WO | WO-2007/047583 | A2 | 4/2007 |
| WO | WO-2007/067183 | | 6/2007 |
| WO | WO-2008/038002 | A2 | 4/2008 |
| WO | WO-2008/039818 | A2 | 4/2008 |
| WO | WO-2008/112922 | | 9/2008 |

(56) References Cited

FOREIGN PATENT DOCUMENTS

| WO | WO-2009/059304 | | 5/2009 |
|---|---|---|---|
| WO | WO-2009/139930 | A2 | 11/2009 |
| WO | WO-2010/011644 | | 1/2010 |
| WO | WO-2010/025421 | A2 | 3/2010 |
| WO | WO-2011/100477 | A2 | 8/2011 |
| WO | WO-2012/055170 | | 5/2012 |
| WO | WO-2013/039889 | A1 | 3/2013 |
| WO | WO-2013/166321 | A1 | 11/2013 |
| WO | WO-2014/018863 | A1 | 1/2014 |
| WO | WO-2014/039908 | A1 | 3/2014 |
| WO | WO-2014/083173 | A1 | 6/2014 |
| WO | WO-2014/133567 | A1 | 9/2014 |
| WO | WO-2014/133568 | A1 | 9/2014 |
| WO | WO-2014/164606 | A1 | 10/2014 |
| WO | WO-2016/105542 | A2 | 6/2016 |
| WO | WO-2017/059319 | A2 | 4/2017 |
| WO | WO-2017/123978 | A1 | 7/2017 |
| WO | WO-2018/104909 | A2 | 6/2018 |

OTHER PUBLICATIONS

Jacobson, et al., "How I treat Burkitt lymphoma in adults." Blood, 2014, vol. 124, No. 19, pp. 2913-2920.
Namikawa, et al., "A case of ABO-incompatible blood transfusion treated by plasma exchange therapy and continuous hemodiafiltration." CEN Case Reports, 2018, vol. 7, pp. 114-120.
Non-Final Office Action on U.S. Appl. No. 17/009,279 Dtd Oct. 27, 2022.
Yu, et al., "Chapter 1: Clinical Overview of Cancer," Clinical References for Cancers (Chinese), May 31, 2004, pp. 151 and 152.
"myc proto-oncogene protein [*Homo sapiens*]", NCBI Protein Database, NCBI, retrieved Jul. 24, 2017 from URL: https://www.ncbi.nlm.nih.gov/protein/71774083?report=genbank&log$=protalign&blast_rank=1&RID=RC7XFBOS014 (4 pages).
"Stem Cell", Wikipedia, 2008, retrieved Nov. 13 from URL: http://en.wikipedia.org/wiki/Stem_cell (11 pages).
Altman et al., "Phenotypic Analysis of Antigen-Specific T Lymphocytes", Science, vol. 274, 1996, pp. 94-96 (4 pages).
Amino Acid, NCBI, 2018 (8 pages).
Andersen et al., "Parallel detection of antigen-specific T cell responses by combinatiorial encoding of MHC multimers", Nature Protocols, vol. 7, No. 5, 2012, pp. 891-902, DOI: 10.1038/nprot.2012.037 (12 pages).
Application for U.S. Appl. No. 12/048,148, filed Mar. 13, 2008 (50 pages).
Application for U.S. Appl. No. 12/506,894, filed Jul. 21, 2009 (59 pages).
Aubry et al., "N-Myc Shares Cellular Functions with c-Myc", DNA and Cell Biology, vol. 19, No. 6, Jun. 2000, pp. 353-364 (12 pages).
Austrian Search Report and Written Opinion SG 201101367-9 dated Mar. 23, 2012 (17 pages).
Baum, Christopher, "Insertional Mutagenesis in Gene Therapy and Stem Cell Biology", Current Opinion in Hematology, vol. 14, Jul. 2007, pp. 337-342 (6 pages).
Beerens et al., "Protein Transduction Domains and their Utility in Gene Therapy", Current Gene Therapy, vol. 3, No. 5, 2003, pp. 486-494 (9 pages).
Benassayag et al., "Human c-Myc Isoforms Differentially Regulate Cell Growth and Apoptosis in *Drosophila melanogaster*," Molecular and Cellular Biology, vol. 25, No. 22, 2005, pp. 9897-9909 (14 pages).
Berkson et al., "Pilot Screening Programme for Small Molecule Activators of p53", International Journal of Cancer, vol. 115, 2005, pp. 701-710, DOI: 10.1002/ijc.20968 (10 pages).
Bird et al., "Expansion of Human and Murine Hematopoietic Stem and Progenitor Cells Ex Vivo without Genetic Modification Using MYC and Bcl-2 Fusion Proteins", PLOS ONE, vol. 9, No. 8, e105525, 2014, pp. 1-20, DOI: 10.1371/journal.pone.0105525 (20 pages).
Bissonnette et al., "Apoptotic cell death induced by c-myc is inhibited by bcl-2", Nature, vol. 359, Oct. 8, 1992, pp. 552-554 (3 pages).
Bouchard et al., "Control of cell proliferation by Myc", Trends in Cell Biology, vol. 8, 1998, pp. 202-206 (5 pages).
Bunting et al., "Restoration of lymphocyte function in Janus kinase 3-deficient mice by retroviral-mediated gene transfer," Nature Medicine, vol. 4, No. 1, 1998, pp. 58-64 (7 pages).
Buske et al., "Deregulated expression of HOXB4 enhances the primitive growth activity of human hematopoietic cells", Blood, vol. 100, No. 3, Aug. 1, 2002, pp. 862-868 (7 pages).
Capecchi, Mario R., "Altering the Genome by Homologous Recombination", Science, vol. 244, No. 4910, Jun. 16, 1989, pp. 1288-1292 (5 pages).
Caron et al., "Endosome disruption enhances the functional nuclear delivery of Tat-fusion proteins", Biochemical and Biophysical Research Communications, vol. 319, No. 1, Jun. 18, 2004, pp. 12-20 (9 pages).
Carotta et al., "Directed differentiation and mass cultivation of pure erythroid progenitors from mouse embryonic stem cells", Blood, vol. 104, No. 6, Sep. 15, 2004, pp. 1873-1880, DOI: 10.1182/blood-2004-02-0570 (8 pages).
Chadwick et al., "Notch Signaling Induces Apoptosis in Primary Human CD34+ Hematopoietic Progenitor Cells", Stem Cells, vol. 25, 2007, pp. 203-210, DOI: 10.1634/stemcells.2005-0303 (10 pages).
Chandran et al., "Tumor-Specific Effector CD8+ T Cells That Can Establish Immunological Memory in Humans after Adoptive Transfer are Marked by Expression of IL7 Receptor and c-myc", Cancer Research, vol. 75, No. 16, 2015, pp. 3216-3226, DOI: 10.1158/0008-5472.CAN-15-0584 (12 pages).
Chang et al., "Phenotypic expression in *E. coli* of a DNA sequence coding for mouse dihydrofolate reductase", Nature, vol. 275, Oct. 19, 1978, pp. 617-624 (8 pages).
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845 (8 pages).
Cheng et al., "BCL-2, BCL-XL, Sequester BH3 Domain-Only Molecules Preventing BAX- and BAK-Mediated Mitochondrial Apoptosis", Molecular Cell, vol. 8, Sep. 2001, pp. 705-711 (7 pages).
Chi et al., "Physical Stability of Proteins in Aqueous Solution: Mechanism and Driving Forces in Nonnative Protein Aggregation," Pharmaceutical Research, vol. 20, No. 9, Sep. 2003, pp. 1325-1336 (2 pages).
Chin et al., "Essential role for oncogenic Ras in tumour maintenance", Nature, vol. 400, Jul. 29, 1999, pp. 468-472 (5 pages).
Choi et al., "Myc protein is stabilized by suppression of a novel E3 ligase complex in cancer cells", Genes & Development, vol. 24, 2010, pp. 1236-1241, DOI: 10.1101/gad.1920310 (6 pages).
Choi et al., "Status Epilepticus-Induced Somatostatinergic Hilar Interneuron Degeneration Is Regulated by Striatal Enriched Protein Tyrosine Phosphatase", Journal of Neuroscience, vol. 27, No. 11, Mar. 14, 2007, pp. 2999-3009, DOI: 10.1523/JNEUROSCI.4913-06.2007 (11 pages).
Cleland et al., "The Development of Stable Protein Formulations: A Close Look at Protein Aggregation, Deamidation, and Oxidation," Critical Reviews in Therapeutic Drug Carrier Systems, vol. 10, No. 4, Jan. 1, 1993, pp. 307-377 (75 pages).
Coeytaux et al., "The Cationic Amphipathic alpha-Helix of HIV-1 Viral Protein R (Vpr) Binds to Nucleic Acids, Permeabilizes Membranes, and Efficiently Transfects Cells", The Journal of Biological Chemistry, vol. 278, No. 20, May 16, 2003, pp. 18110-18116 (8 pages).
Coller et al., "Expression analysis with oligonucleotide microarrays reveals that MYC regulates genes involved in growth, cell cycle, signaling, and adhesion", Proceedings of the National Academy of Sciences USA, vol. 97, No. 7, 2000, pp. 3260-3265 (6 pages).
Communication pursuant to Rules 161(2) and 162 EPC for EP 17876016.1 dated Jul. 9, 2019 (3 pages).

(56) References Cited

OTHER PUBLICATIONS

Conti, et al., "Gene Therapy Using Neural Stem Cells", Methods in Molecular Biology, vol. 198, 2002, pp. 233-244, XP009120658 (12 pages).
Coppola et al., "Constitutive c-myc oncogene expression blocks mouse erythroleukaemia cell differentiation but not commitment", Nature, vol. 320, Apr. 24, 1986, pp. 760-763 (4 pages).
Corrected Notice of Allowability for U.S. Appl. No. 15/179,735 dated Jun. 15, 2018 (2 pages).
Corrected Notice of Allowability for U.S. Appl. No. 15/179,735 dated Jun. 8, 2018 (2 pages).
Corrected Notice of Allowability for U.S. Appl. No. 16/042,904 dated Mar. 6, 2020 (4 pages).
Corrected Notice of Allowance for U.S. Appl. No. 15/643,133 dated Jun. 8, 2020 (2 pages).
Corrected Notice of Allowance for U.S. Appl. No. 15/717,675 dated Jan. 10, 2020 (2 pages).
Corrected Notice of Allowance for U.S. Appl. No. 15/717,675 dated Nov. 6, 2019 (4 pages).
Corrected Notice of Allowance for U.S. Appl. No. 16/042,904 dated Jan. 29, 2020 (2 pages).
Corrected Notice of Allowance for U.S. Appl. No. 16/042,904 dated Jun. 2, 2020 (4 pages).
Corrected Notice of Allowance for U.S. Appl. No. 16/042,904 dated Jun. 22, 2020 (4 pages).
Corrected Notice of Allowance for U.S. Appl. No. 16/261,207 dated Feb. 1, 2021 (4 pages).
D'Alessandro et al., "Red blood cell storage: the story so far", Blood transfusion = Trasfusione del sangue, vol. 8, 2010, pp. 82-88, DOI: 10.2450/2009.0122-09 (7 pages).
Dang et al., "Identification of the Human c-myc Protein Nuclear Translocation Signal", Molecular and Cellular Biology, vol. 8, No. 10, Oct. 1988, pp. 4048-4054 (7 pages).
Dang et al., "Nuclear and Nucleolar Targeting Sequences of c-erb-A, c-myb, N-myc, p53, HSP70, and HIV tat Proteins", Journal of Biological Chemistry, vol. 264, No. 30, Oct. 25, 1989, pp. 18019-18023 (5 pages).
Dang, Chi V., "c-Myc Target Genes Involved in Cell Growth, Apoptosis, and Metabolism", Molecular and Cellular Biology, vol. 19, No. 1, Jan. 1999, pp. 1-11 (11 pages).
Daugas et al., "Erythrocytes: Death of a mummy", Cell Death and Differentiation, vol. 8, No. 12, 2001, pp. 1131-1133 (3 pages).
De Boer et al., "The tac promoter: A functional hybrid derived from the trp and lac promoters", Proceedings of the National Academy of Sciences USA, Biochemistry, vol. 80, 1983, pp. 21-25 (5 pages).
De Korte, D. "New additive solutions for red cells", ISBT Science Series, vol. 11, Suppl. 1, 2016, pp. 165-170 (6 pages).
Decision of Rejection for CN 200580031545.8 dated Jul. 3, 2012, English Translation Only (11 pages).
Decision of Rejection for CN 201380048261.4 dated Apr. 16, 2019 (15 pages).
Decision of Rejection for JP 2008-536713 dated Aug. 5, 2013, English Translation Only (2 pages).
Decision of Rejection for JP 2011-520133 dated Nov. 26, 2014 (9 pages).
Decision of Rejection for JP 2011-525258 date Dec. 3, 2014 (11 pages).
Decision of Rejection for JP 2014-108137 dated Jun. 2, 2016 (25 pages).
Decision of Rejection for JP 2018-153567 dated Mar. 18, 2020 (7 pages).
Delgado et al., "Myc Roles in Hematopoiesis and Leukemia", Genes and Cancer, vol. 1, No. 6, 2010, pp. 605-616, DOI: 10.1177/1947601910377495 (12 pages).
Deocampo, et al., "Cooperation of bcl-2 and myc in the neoplastic transformation of normal rat liver epithelial cells is related to the down-regulation of gap junction-mediated intercellular communication", Carcinogenesis, vol. 21, No. 8, 2000, pp. 1501-1506 (6 pages).
Derossi et al., "Trojan peptides: the penetratin system for intracellular delivery", Cell Biology, vol. 8, Feb. 1998, pp. 84-87 (4 pages).
Dmitrovsky et al., "A Transfected c-myc Oncogene Inhibits Mouse Erytholeukemic Differentiation", Current Topics in Microbiology and Immunology, vol. 132, 1986 (4 pages).
Domashenko et al., "TAT-mediated transduction of NF-Ya peptide induces the ex vivo proliferation and egraftment potential of human hematopoietic progenitor cells," Blood, vol. 116, No. 15, Oct. 14, 2010, pp. 2676-2683 (9 pages).
Domen et al., "The Role of Apoptosis in the Regulation of Hematopoietic Stem Cells: Overexpression of BCL-2 Increase Both Their Number and Repopulation Potential", Journal of Experimental Medicine, vol. 191, No. 2, 2000, pp. 253-263 (11 pages).
Dudley et al., "Adoptive Cell Transfer Therapy Following Non-Myeloablative but Lymphodepleting Chemotherapy for the Treatment of Patients with Refractory Metastatic Melanoma", Journal of Clinical Oncology, vol. 23, No. 10, Apr. 1, 2005, pp. 2346-2357, DOI: 10.1200/JCO.2005.00.240 (12 pages).
Dvorak et al., "Cytochemical Localization of Peroxidase Activity in the Developing Erythrocyte", American Journal of Pathology, vol. 67, No. 2, 1972, pp. 303-326 (24 pages).
Eilers et al., "Chimaeras of Myc oncoprotein and steroid receptors cause hormone-dependent transformation of cells", Nature, vol. 340, No. 6228, Jul. 6, 1989, pp. 66-68 (3 pages).
Eischen et al., "Apoptosis Triggered by Myc-Induced Suppression of Bcl-XL or Bcl-2 Is Bypassed during Lymphomagenesis", Molecular and Cellular Biology, vol. 21, No. 15, Aug. 2001, pp. 5063-5070, DOI: 10.1128/MCB.21.15.5063-5070.2001 (9 pages).
Elliot et al., "Intercellular Trafficking and Protein Delivery by a Herpesvirus Structural Protein", Cell, vol. 88, Jan. 24, 1997, pp. 223-233 (11 pages).
Esdar et al., "Differentiation-associated apoptosis of neural stem cells is effected by Bcl-2 overexpression: impact on cell lineage determination" European Journal of Cell Biology, vol. 80, No. 8, Aug. 2001, pp. 539-553 (15 pages).
Examination Report for AU 2018247295 dated Dec. 6, 2019 (2 pages).
Examination Report for CA 2626525 dated Apr. 17, 2013 (4 pages).
Examination Report for CA 2626525 dated Apr. 8, 2014 (4 pages).
Examination Report for CA 2626525 dated Jul. 4, 2018 (3 pages).
Examination Report for CA 2626525 dated Jun. 13, 2017 (3 pages).
Examination Report for CA 2626525 dated Jun. 6, 2016 (3 pages).
Examination Report for CA 2626525 dated May 8, 2015 (3 pages).
Examination Report for CA 2680613 dated Nov. 21, 2013 (3 pages).
Examination Report for CA 2680613 dated Nov. 28, 2014 (4 pages).
Examination Report for CA 2723114 dated Apr. 21, 2015 (4 pages).
Examination Report for CA 2723114 dated Jul. 7, 2016 (3 pages).
Examination Report for CA 2731767 dated Jul. 25, 2012 (3 pages).
Examination Report for CA 2731767 dated Oct. 5, 2015 (3 pages).
Examination Report for CA 2731767 dated Sep. 5, 2014 (2 pages).
Examination Report for CA 2735522 dated Nov. 16, 2015 (2 pages).
Examination Report for CA 2735522 dated Oct. 2, 2014 (2 pages).
Examination Report for CA 2735522 dated Sep. 10, 2012 (3 pages).
Examination Report for CA 2879667 dated Jun. 18, 2019 (4 pages).
Examination Report for CA 2879667 dated May 25, 2020 (4 pages).
Examination Report for CA 2905285 dated Jan. 30, 2020 (5 pages).
Examination Report for CA 2905296 dated Feb. 11, 2021 (7 pages).
Examination Report for CA 2905296 dated Jan. 31, 2020 (4 pages).
Examination Report for CA 3035209 dated Feb. 3, 2020 (4 pages).
Examination Report for CA 3035209 dated Feb. 4, 2021 (4 pages).
Examination Report for CA 3065947 dated Nov. 4, 2020 (4 pages).
Examination Report for CA 3065947 dated Oct. 13, 2021 (4 pages).
Examination Report for EP 06826025.6 dated Sep. 22, 2009 (1 page).
Examination Report for EP 08743862.8 dated Sep. 23, 2010 (6 pages).
Examination Report for EP 08743862.8 dated on May 14, 2010 (6 pages).
Examination Report for EP 09747016.5 dated Apr. 9, 2013 (6 pages).
Examination Report for EP 09747016.5 dated Jul. 26, 2016 (5 pages).

(56) References Cited

OTHER PUBLICATIONS

Examination Report for EP 09747016.5 dated Jun. 12, 2017 (6 pages).
Examination Report for EP 09747016.5 dated Mar. 19, 2015 (5 pages).
Examination Report for EP 09747016.5 dated May 15, 2018 (7 pages).
Examination Report for EP 09810692.5 dated Mar. 28, 2012 (3 pages).
Examination Report for EP 09810692.5 dated Oct. 22, 2014 (3 pages).
Examination Report for EP 12187097.6 dated Jan. 22, 2015 (6 pages).
Examination Report for EP 13820331.0 dated Apr. 24, 2018 (4 pages).
Examination Report for EP 13820331.0 dated Jul. 29, 2019 (3 pages).
Examination Report for EP 14778538.0 dated Apr. 16, 2018 (4 pages).
Examination Report for EP 14779483.8 dated Apr. 28, 2021 (3 pages).
Examination Report for EP 14779483.8 dated Aug. 11, 2020 (3 pages).
Examination Report for EP 14779483.8 dated Jan. 14, 2019 (4 pages).
Examination Report for EP 14779483.8 dated Jun. 28, 2019 (4 pages).
Examination Report for EP 14779483.8 dated Jun. 29, 2018 (4 pages).
Examination Report for EP 14779483.8 dated Oct. 16, 2017 (4 pages).
Examination Report for EP 17876016.1 dated Apr. 12, 2021 (5 pages).
Examination Report for EP 17920607.3 dated Aug. 26, 2020 (5 pages).
Examination Report for EP 18154875.1 dated Sep. 6, 2019 (4 pages).
Examination Report for IN 2048/DELNP/2011 dated Sep. 15, 2016 (9 pages).
Examination Report for IN 3332/DELNP/2008 dated Aug. 23, 2013 (6 pages).
Examination Report for IN 634/DELNP/2011 dated Jun. 8, 2017 (10 pages).
Examination Report for IN 6624/DELNP/2014 dated Sep. 27, 2018 (4 pages).
Examination Report for IN 9033/DELNP/2010 dated May 19, 2017 (11 pages).
Examination Report for IN 9205/DELNP/2015 dated Nov. 28, 2019 (8 pages).
Examination Report for IN 9206/DELNP/2015 dated Dec. 26, 2019 (6 pages).
Examination Report No. 1 for AU 2009285547 dated Jul. 25, 2011 (2 pages).
Examination Report No. 1 for AU 2013292330 dated Sep. 6, 2017 (3 pages).
Examination Report No. 1 for AU 2014202016 dated May 12, 2015 (3 pages).
Examination Report No. 1 for AU 2014249200 dated Mar. 15, 2019 (4 pages).
Examination Report No. 1 for AU 2016203892 dated Apr. 12, 2017 (3 pages).
Extended European Search Report for EP 06826025.6 dated Aug. 13, 2009 (8 pages).
Extended European Search Report for EP 09747016.5 dated May 30, 2012 (8 pages).
Extended European Search Report for EP 09800871.7 dated Jun. 24, 2011 (5 pages).
Extended European Search Report for EP 09810692.5 dated Jul. 11, 2011 (5 pages).
Extended European Search Report for EP 12187077.8 dated Mar. 25, 2013 (7 pages).
Extended European Search Report for EP 12187097.6 dated Mar. 27, 2013 (8 pages).
Extended European Search Report for EP 13188850.0 dated May 27, 2014 (8 pages).
Extended European Search Report for EP 13820331.0 dated Oct. 10, 2016 (9 pages).
Extended European Search Report for EP 14778538.0 dated Sep. 29, 2016 (17 pages).
Extended European Search Report for EP 14779483.8 dated Dec. 23, 2016 (5 pages).
Extended European Search Report for EP 15175802.6 dated Dec. 14, 2015 (7 pages).
Extended European Search Report for EP 17876016.1 dated Jun. 26, 2020 (7 pages).
Extended European Search Report for EP 18154875.1 dated Apr. 24, 2018 (8 pages).
Extended European Search Report for EP 18841366.0 dated Mar. 16, 2021 (7 pages).
Extended European Search Report for EP 20212922.7 dated May 26, 2021 (7 pages).
Extended European Search Report for EP 21170329.3 dated Oct. 22, 2021 (10 pages).
Extended Search Report for EP 17920607.3 dated Dec. 11, 2019 (7 pages).
Extended Search Report for EP 19157513.3 dated Apr. 1, 2019 (13 pages).
Fanidi et al., "Cooperative interaction between c-myc and bcl-2 proto-oncogenes", Nature, vol. 359, Oct. 8, 1992, pp. 554-556 (3 pages).
Felsher et al., "Reversible Tumorigenesis by MYC in Hematopoietic Lineages", Molecular Cell, vol. 4, Aug. 1999, pp. 199-207 (9 pages).
Fifth Office Action for CN 200980126312.4 dated Jan. 22, 2014, English Translation Only (3 pages).
Filing Receipt for IL 265409 dated Oct. 19, 2021 (2 pages).
Final Office Action for U.S. Appl. No. 11/583,970 dated Apr. 9, 2014 (20 pages).
Final Office Action for U.S. Appl. No. 11/583,970 dated Nov. 17, 2011 (16 pages).
Final Office Action for U.S. Appl. No. 11/583,970 dated Nov. 26, 2008 (14 pages).
Final Office Action for U.S. Appl. No. 11/583,970 dated Nov. 4, 2009 (10 pages).
Final Office Action for U.S. Appl. No. 12/048,148 dated Feb. 15, 2013 (17 pages).
Final Office Action for U.S. Appl. No. 12/467,957 dated Feb. 28, 2011 (8 pages).
Final Office Action for U.S. Appl. No. 12/467,957 dated Sep. 17, 2014 (9 pages).
Final Office Action for U.S. Appl. No. 12/506,894 dated Oct. 9, 2014 (15 pages).
Final Office Action for U.S. Appl. No. 12/550,166 dated May 11, 2012 (12 pages).
Final Office Action for U.S. Appl. No. 12/701,383 dated Nov. 13, 2014 (18 pages).
Final Office Action for U.S. Appl. No. 12/701,383 dated Nov. 16, 2011 (14 pages).
Final Office Action for U.S. Appl. No. 13/795,659 dated Jul. 11, 2014 (16 pages).
Final Office Action for U.S. Appl. No. 13/795,659 dated Mar. 26, 2015 (18 pages).
Final Office Action for U.S. Appl. No. 13/797,648 dated Apr. 1, 2015 (12 pages).
Final Office Action for U.S. Appl. No. 13/797,648 dated Feb. 8, 2017 (18 pages).
Final Office Action for U.S. Appl. No. 14/461,105 dated Sep. 15, 2016 (6 pages).
Final Office Action for U.S. Appl. No. 14/509,870 dated Feb. 3, 2017 (16 pages).
Final Office Action for U.S. Appl. No. 14/873,296 dated Jan. 24, 2018 (17 pages).

(56) References Cited

OTHER PUBLICATIONS

Final Office Action for U.S. Appl. No. 15/244,138 dated Jun. 4, 2018 (15 pages).
Final Office Action for U.S. Appl. No. 15/244,138 dated Mar. 14, 2019 (14 pages).
Final Office Action for U.S. Appl. No. 15/668,451 dated May 24, 2018 (10 pages).
Final Office Action for U.S. Appl. No. 15/717,675 dated Jun. 27, 2019 (10 pages).
Final Office Action for U.S. Appl. No. 16/042,904 dated Nov. 1, 2019 (10 pages).
Final Office Action for U.S. Appl. No. 16/184,086 dated Jun. 9, 2020 (7 pages).
Final Office Action for U.S. Appl. No. 16/901,956 dated Aug. 6, 2021 (10 pages).
Final Office Action Response for U.S. Appl. No. 11/583,970 dated Feb. 4, 2010 (10 pages).
Final Office Action Response for U.S. Appl. No. 11/583,970 dated Jan. 28, 2009 (15 pages).
Final Rejection for KR 10-2009-7021320 dated May 29, 2013 (6 pages).
Final Rejection for KR 10-2010-7028384 dated Mar. 28, 2017 (6 pages).
First Office Action and Search Report for CN 201780082261.4 dated Jul. 28, 2020 (15 pages).
First Office Action for CN 200680045545.8 dated Dec. 31, 2010, English Translation Only (8 pages).
First Office Action for CN 200880015602.7 dated Jan. 31, 2012 (16 pages).
First Office Action for CN 200980126312.4 dated Jan. 30, 2012 (14 pages).
First Office Action for CN 200980127166.7 dated Dec. 5, 2012 (4 pages).
First Office Action for CN 201380048261.4 dated May 24, 2018 (17 pages).
First Office Action for CN 201410168106.2 dated Sep. 16, 2015 (9 pages).
First Office Action for CN 201410479685.2 dated Nov. 17, 2015 (12 pages).
First Office Action for CN 201480026147.6 dated Oct. 25, 2016 (13 pages).
First Office Action for CN 201480026500.0 dated Aug. 10, 2017 (22 pages).
First Office Action for CN 201510760532X dated May 11, 2018 (13 pages).
First Office Action for CN 201780052978.4 dated Sep. 23, 2021 (10 pages).
First Office Action for CN 201810243366.X dated Jan. 25, 2021 (11 pages).
Foreign Search Report and Written Opinion issued for SG Appl. Ser. No. 10201707390V dated Oct. 13, 2021 (9 pages).
Fourth Office Action for CN 200880015602.7 dated Nov. 11, 2013, English Translation Only (6 pages).
Fourth Office Action for CN 201410168106.2 dated Jun. 22, 2017 (8 pages).
Futaki, Chemistry and Biology (Kagaku to Seibutsu), vol. 43, No. 10, Oct. 1, 2005, pp. 649-653.
Gandarillas et al., "c-Myc promotes differentiation of human epidermal stem cells", Genes & Development, vol. 11, 1997, pp. 2869-2882 (15 pages).
Gauss et al., "DEAE-dextran enhances electroporation of mammalian cells", Nucleic Acids Research, vol. 20, No. 24, 1992, pp. 6739-6740 (2 pages).
Goeddel et al., "Direct expression in *Escherichia coli* of a DNA sequence coding for human growth hormone", Nature, vol. 281, Oct. 18, 1979, pp. 544-548 (5 pages).
Goeddel et al., "Synthesis of human fibroblast interferon by *E. coli*", Nucleic Acids Research, vol. 8, No. 18, Aug. 12, 1980, pp. 4057-4074 (18 pages).

Gross et al., "BCL-2 family members and the mitochondria in apaptosis", Genes & Development, vol. 13, No. 15, Aug. 1999, pp. 1899-1911 (14 pages).
Grumont et al., "The Mitogen-Induced Increase in T Cell Size Involves PKC and NFAT Activation of Rel/NF-kappaB-Dependent c-myc Expression", Immunity, vol. 21, Jul. 2004, pp. 19-30 (12 pages).
Guzman et al., "Preferential induction of apoptosis for primary human leukemic stem cells", Proceedings of the National Academy of Sciences, vol. 99, No. 25, Dec. 10, 2002, pp. 16220-16225, DOI: 10.1073/pnas.252462599 (6 pages).
Habib et al., "Myc Stimulates B lymphocyte differentiation and amplifies calcium signaling", The Journal of Cell Biology, vol. 179, No. 4, 2007, pp. 717-731, DOI: 10.1083/jcb.200704173 (11 pages).
Hann et al., "Proteins Encoded by the Human c-myc Oncogene: Differential Expression in Neoplastic Cells", Molecular and Cellular Biology, vol. 4, No. 11, Nov. 1984, pp. 2486-2497 (12 pages).
Henikoff et al., "Amino acid substitution matrices from protein blocks", Proceedings of the National Academy of Sciences USA, vol. 89, Nov. 1992, pp. 10915-10919 (5 pages).
Hiramatsu et al., "Complete reconstitution of human lymphocytes from cord blood CD34+ cells using the NOD/SCID/gamma-c-null mice model", Blood, vol. 102, No. 3, Aug. 1, 2003, pp. 873-880 (8 pages).
Hirose et al., "Immortalization of Erythroblasts by c-MYC and BCL-XL Enables Large-Scale Erythrocyte Production from Human Pluripotent Stem Cells", Stem Cell Reports, vol. 1, Dec. 17, 2013, pp. 99-508 (10 pages).
Ho et al., "Synthetic Protein Transduction Domains: Enhanced Transduction Potential in Vitro and in Vivo", Cancer Research, vol. 61, Jan. 15, 2001, pp. 474-477 (5 pages).
Hoffman, Ronald, "Progress in the development of systems for in vitro expansion of human hematopoietic stem cells", Current Opinion in Hematology, vol. 6, No. 3, 1999, pp. 184 (14 pages).
Horton et al., "Continuous MLL-ENL Expression Is Necessary to Establish a 'Hox Code' and Maintain Immortalization of Hematopoietic Progenitor Cells", Cancer Research, vol. 65, No. 20, Oct. 15, 2005, pp. 9245-9252, DOI: 10.1158/0008-5472.CAN-05-1691 (9 pages).
Hoshimaru et al., "Differentiation of the immortalized adult neuronal progenitor cell line HC2S2 into neurons by regulatable suppression of the v-myc oncogene", Proceedings of the National Academy of Sciences USA, Neurobiology, vol. No. 4, Feb. 1996, pp. 1518-1523 (6 pages).
Howard et al., "Transplantation of apoptosis-resistant embryonic stem cells into the injured rat spinal cord", Somatosensory and Motor Research, vol. 22, No. 1/2, Mar./Jun. 2005, pp. 37-44, DOI: 10.1080/08990220500084909 (9 pages).
Huang et al., "Dynamic Regulation of c-Myc proto-oncogene expression during lymphocyte development revealed by a GFP-c-Myc knock-in mouse", European Journal of Immunology, vol. 38, No. 2, 2008, pp. 342-349, DOI: 10.1002/eji.200737972 (8 pages).
Huang et al., "Negative Control of the Myc Protein by the Stress-Responsive Kinase Pak2", Molecular and Cellular Biology, vol. 24, No. 4, Feb. 2004, pp. 1582-1594, DOI: 10.1128/MCB.24.4.1582-1594.2004 (13 pages).
Huettner et al., "Reversibility of acute B-cell leukaemia induced by BCR-ABL1", Nature Genetics, vol. 24, Jan. 2000, pp. 57-60 (4 pages).
International Preliminary Report on Patentability, Ch. I, for PCT/US09/55443 dated Mar. 1, 2011 (6 pages).
International Preliminary Report on Patentability, Ch. I, for PCT/US2006/040379 dated Apr. 23, 2008 (5 pages).
International Preliminary Report on Patentability, Ch. I, for PCT/US2008/056896 dated Sep. 15, 2009 (4 pages).
International Preliminary Report on Patentability, Ch. I, for PCT/US2008/082263 dated May 4, 2010 (6 pages).
International Preliminary Report on Patentability, Ch. I, for PCT/US2009/003105 dated Nov. 17, 2010 (6 pages).
International Preliminary Report on Patentability, Ch. I, for PCT/US2009/051242 dated Jan. 25, 2011 (6 pages).
International Preliminary Report on Patentability, Ch. I, for PCT/US2009/055443 dated Mar. 1, 2011 (6 pages).

(56) References Cited

OTHER PUBLICATIONS

International Preliminary Report on Patentability, Ch. I, for PCT/US2013/051384 dated Jan. 29, 2015 (10 pages).
International Preliminary Report on Patentability, Ch. I, for PCT/US2014/022971 dated Sep. 24, 2015 (8 pages).
International Preliminary Report on Patentability, Ch. I, for PCT/US2014/022977 dated Sep. 15, 2015 (9 pages).
International Preliminary Report on Patentability, Ch. I, for PCT/US2017/045336 dated Feb. 13, 2020 (8 pages).
International Preliminary Report on Patentability, Ch. I, for PCT/US2017/064206 dated Jun. 13, 2019 (13 pages).
International Preliminary Report on Patentability, Ch. I, for PCT/US2019/062200 dated Jun. 3, 2021 (9 pages).
International Preliminary Report on Patentability, Ch. I, for PCT/US2020/027070 dated Oct. 21, 2021 (9 pages).
International Search Report and Written Opinion for PCT/US17/45336 dated Nov. 3, 2017 (15 pages).
International Search Report and Written Opinion for PCT/US2006/040379 dated Sep. 24, 2007 (7 pages).
International Search Report and Written Opinion for PCT/US2008/056896 dated Aug. 14, 2008 (5 pages).
International Search Report and Written Opinion for PCT/US2008/082263 dated Jun. 25, 2009 (8 pages).
International Search Report and Written Opinion for PCT/US2009/003105 dated Jan. 15, 2010 (9 pages).
International Search Report and Written Opinion for PCT/US2009/051242 dated Feb. 19, 2010 (9 pages).
International Search Report and Written Opinion for PCT/US2009/055443 dated Jun. 30, 2010 (11 pages).
International Search Report and Written Opinion for PCT/US2013/051384 dated Nov. 13, 2013 (15 pages).
International Search Report and Written Opinion for PCT/US2014/022971 dated Aug. 13, 2014 (12 pages).
International Search Report and Written Opinion for PCT/US2014/022977 dated Aug. 28, 2014 (13 pages).
International Search Report and Written Opinion for PCT/US2017/064206 dated Mar. 19, 2018 (17 pages).
International Search Report and Written Opinion for PCT/US2018/044740 dated Oct. 16, 2018 (13 pages).
International Search Report and Written Opinion for PCT/US2019/062200 dated Jan. 16, 2020 (13 pages).
International Search Report and Written Opinion for PCT/US2020/027070 dated Sep. 18, 2020 (13 pages).
International Search Report and Written Opinion for PCT/US2020/032702 dated Nov. 18, 2020 (16 pages).
Invitation for EP 09810692.5 dated Feb. 25, 2014 (3 pages).
Invitation for EP 15175802.6 dated Jan. 31, 2017 (4 pages).
Invitation to Pay Additional Fees and, Where Applicable, Protest Fee for PCT/US2014/22971 dated May 27, 2014 (2 pages).
Invitation to Pay Additional Fees and, Where Applicable, Protest Fee, for PCT/US2020/027070 dated Jul. 21, 2020 (2 pages).
Iritani et al., "c-Myc enhances protein synthesis and cell size during B lymphocyte development", Proceedings of the National Academy of Sciences, vol. 96, No. 23, Nov. 9, 1999, pp. 13180-13185 (6 pages).
Iritani et al., "Modulation of T-lymphocyte development, growth and cell size by the Myc antagonist and transcriptional repressor Mad1", The EMBO Journal, vol. 21, No. 18, 2002, pp. 4820-4830 (11 pages).
Jadlowsky et al., "Dominant negative mutant Cyclin T1 proteins inhibit HIV transcription by specifically degrading Tat", Retrovirology, vol. 5, No. 63, 2008, DOI: 10.1186/1742-4690-5-63 (12 pages).
Jayapal et al., "Down-regulation of Myc Is Essential for Terminal Erythroid Maturation", Journal of Biological Chemistry, vol. 285, No. 51, Dec. 17, 2010, pp. 40252-40265, DOI: 10.1074/jbc.M110.181073 (14 pages).
Johnson et al., "Lymphomas with concurrent BCL2 and MYC translocations: the critical factors associated with survival", Blood, vol. 114, No. 11, Sep. 10, 2009, pp. 2273-2279 (7 pages).
Ju et al., "Anti-apoptotic therapy with a Tat fusion protein against excitotoxic insults in vitro and in vivo", Experimental Neurology, vol. 210, No. 2, 2008, pp. 602-607, DOI: 10.1016/j.expneurol.2007.12.008 (6 pages).
Kaptein et al., "Anti-IgM-mediated Regulation of c-myc and Its Possible Relationship to Apoptosis", The Journal of Biological Chemistry, vol. 271, No. 31, Aug. 2, 1996, pp. 18875-18884 (11 pages).
Karon et al., "Temporal sequence of major biochemical events during Blood Bank storage of packed red blood cells", Blood Transfusion, vol. 10, 2012, pp. 453-461, DOI: 10.2450/2012.0099-11 (9 pages).
Kashio et al., "A Protein Derived From the Fusion of TAT Peptide and FNK, a Bcl-XL Derivative, Prevents Cochlear Hair Cell Death From Aminoglycoside Ototoxicity In Vivo", Journal of Neuroscience Research, vol. 85, No. 7, 2007, pp. 1403-1412, DOI: 10.1002/jnr.21260 (10 pages).
Kelso et al., "Survival of the Myeloid Progenitor Cell Line FDC-P1 is Prolonged by Interferon-gamma or Interleukin-4", Growth Factors, vol. 6, No. 3, 1992, pp. 233-242 (10 pages).
Kitada et al., "Reversal of Chemoresistance of Lymphoma Cells by Antisense-Mediated Reduction of bcl-2 Gene Expression", Antisense Research and Development, vol. 4, 1994, pp. 71-79 (9 pages).
Korbling et al., "Allogeneic Blood Stem Cell Transplantation: Peripheralization and Yield of Donor-Derived Primitive Hematopoietic Progenitor Cells (CD34+Thy-1dim) and Lymphoid Subsets, and Possible Predictors of Engraftment and Graft-Versus-Host Disease", Blood, vol. 86, No. 7, Oct. 1, 1995, pp. 2842-2848 (7 pages).
Krosl et al., "In vitro expansion of hematopoietic stem cells by recombinant TAT-HOXB4 protein" Nature Medicine, vol. 9, No. 11, Nov. 2003, pp. 1428-1432, DOI: 10.1038/nm951 (5 pages).
Lang et al., "Mechanisms and Significance of Erypotosis, the Suicidal Death of Erythrocytes", Blood Purification, vol. 33, 2012, pp. 125-130, DOI: 10.1159/00034163 (6 pages).
Laurenti et al., "Hematopoietic Stem Cell Function and Survival Depend on c-Myc and N-Myc Activity", Cell Stem Cell, vol. 3, 2008, pp. 611-624, DOI: 10.1016/j.stem.2008.09.005 (14 pages).
Levesque et al., "The endosteal 'osteoblastic' niche and its role in hematopoietic stem cell homing and mobilization", Leukemia, vol. 24, 2010, pp. 1979-1992, DOI: 10.1038/leu.2010.214 (14 pages).
Li et al., "Reconstitution of functional human B lymphocytes in NOD/SCID mice engrafted with ex vivo expanded CD34+ cord blood cells", Experimental Hematology, vol. 30, 2002, pp. 1036-1043 (8 pages).
Littlewood et al., "A modified oestrogen receptor ligand-binding domain as an improved switch for the regulation of heterologous proteins", Nucleic Acids Research, vol. 23, No. 10, 1995, pp. 1686-1690 (5 pages).
MacPherson et al., "Activity-Dependent Gene Regulation in Conditionally-Immortalized Muscle Precursor Cell Lines," Journal of Cellular Biochemistry, vol. 91, No. 4, 2004, pp. 821-839, DOI: 10.1002/jcb.10784 (19 pages).
McCarthy, Nicola, "Underground movement", Nature Reviews: Cancer, vol. 7, Nov. 2007, DOI: 10.1038/nrc2257 (1 page).
McNiece et al, "Ex-vivo expansion of hematopoietic progenitor cells: preliminary results in breast cancer", Hematology and Cell Therapy, vol. 41, No. 2, 1999, pp. 82-86 DOI: 10.1007/s00282-999-0082-y (6 pages).
Melkonyan et al., "Electroporation efficiency in mammalian cells is increased by dimethyl sulfoxide (DMSO)", Nucleic Acids Research, vol. 24, No. 21, 1996, pp. 4356-4357, DOI: 10.1093/nar/24.21.4356 (2 pages).
Merino et al., "Developmental regulation of the Bcl-2 protein and susceptibility to cell death in B lymphocytes", The EMBO Journal, vol. 13, No. 3, 1994, pp. 683-691, DOI: 10.1002/j.1460-2075.1994.tb06307.x (9 pages).
Miharada et al., "Efficient enucleation of erythroblasts differentiated in vitro from hematopoietic stem and progenitor cells", Nature Biotechnology, vol. 24, No. 10, 2006, pp. 1255-1256, DOI: 10.1038/nbt1245 (2 pages).
Miller et al., "Expansion in vitro of adult murine hematopoietic stem cells with transplantable lympho-myeloid reconstituting ability",

(56) References Cited

OTHER PUBLICATIONS

Proceedings of the National Academy of Sciences USA, vol. 94, Dec. 1997, pp. 13648-13653, DOI: 10.1073/pnas.94.25.13648 (6 pages).
Moore et al., "In Vitro Maintenance of Highly Purified, Transplantable Hematopoietic Stem Cells", Blood, vol. 89, No. 12, 1997, pp. 4337-4347, DOI: 10.1182/blood.V89.12.4337 (12 pages).
Mooslehner et al., "Retroviral Integration Sites in Transgenic Mov Mice Frequently Map in the Vicinity of Transcribed DNA Regions", Journal of Virology, vol. 64, 1990, pp. 3056-3058, DOI: 10.1128/jvi.64.6.3056-3058.1990 (3 pages).
Muchmore et al., "X-ray and NMR structure of human Bcl-XL, an inhibitor of programmed cell death", Nature, vol. 381, May 23, 1996, pp. 335-341, DOI: 10.1038/381335a0 (7 pages).
Murphy et al., "Id2 Is Dispensable for Myc-Induced Epidermal Neoplasia", Molecular and Cellular Biology, vol. 24, No. 5, Mar. 2004, pp. 2083-2090, DOI: 10.1128/MCB.24.5.2083-2090.2004 (8 pages).
Non Final Office Action for U.S. Appl. No. 11/583,970 dated May 9, 2011 (11 pages).
Non Final Office Action for U.S. Appl. No. 12/048,148 dated Oct. 13, 2011 (10 pages).
Non Final Office Action for U.S. Appl. No. 12/962,197 dated Aug. 26, 2011 (12 pages).
Non-Final Office Action for U.S. Appl. No. 11/583,970 dated Mar. 12, 2008 (16 pages).
Non-Final Office Action for U.S. Appl. No. 11/583,970 dated Mar. 23, 2009 (12 pages).
Non-Final Office Action for U.S. Appl. No. 11/583,970 dated Sep. 20, 2013 (20 pages).
Non-Final Office Action for U.S. Appl. No. 12/048,148 dated Jan. 19, 2011 (7 pages).
Non-Final Office Action for U.S. Appl. No. 12/048,148 dated May 11, 2012 (10 pages).
Non-final Office Action for U.S. Appl. No. 12/467,957 dated Apr. 4, 2014 (14 pages).
Non-Final Office Action for U.S. Appl. No. 12/467,957 dated Oct. 13, 2010 (15 pages).
Non-Final Office Action for U.S. Appl. No. 12/506,894 dated Apr. 27, 2012 (14 pages).
Non-Final Office Action for U.S. Appl. No. 12/506,894 dated Apr. 3, 2015 (16 pages).
Non-Final Office Action for U.S. Appl. No. 12/550,166 dated Jan. 11, 2012 (8 pages).
Non-Final Office Action for U.S. Appl. No. 12/701,383 dated Apr. 28, 2011 (10 pages).
Non-Final Office Action for U.S. Appl. No. 12/701,383 dated Jun. 13, 2014 (26 pages).
Non-Final Office Action for U.S. Appl. No. 13/795,659 dated Mar. 10, 2014 (12 pages).
Non-Final Office Action for U.S. Appl. No. 13/795,659 dated Nov. 26, 2014 (13 pages).
Non-Final Office Action for U.S. Appl. No. 13/797,648 dated Apr. 3, 2014 (14 pages).
Non-Final Office Action for U.S. Appl. No. 13/797,648 dated Apr. 19, 2018 (14 pages).
Non-Final Office Action for U.S. Appl. No. 13/797,648 dated Jun. 17, 2016 (17 pages).
Non-Final Office Action for U.S. Appl. No. 14/415,325 dated Dec. 23, 2016 (14 pages).
Non-Final Office Action for U.S. Appl. No. 14/461,105 dated Mar. 20, 2017 (7 pages).
Non-Final Office Action for U.S. Appl. No. 14/461,105 dated Mar. 22, 2016 (8 pages).
Non-Final Office Action for U.S. Appl. No. 14/509,870 dated Jul. 12, 2016 (21 pages).
Non-Final Office Action for U.S. Appl. No. 14/661,786 dated Aug. 27, 2015 (19 pages).
Non-Final Office Action for U.S. Appl. No. 14/873,296 dated Aug. 17, 2017 (18 pages).
Non-Final Office Action for U.S. Appl. No. 15/179,735 dated Feb. 26, 2018 (12 pages).
Non-Final Office Action for U.S. Appl. No. 15/244,138 dated Jan. 22, 2018 (28 pages).
Non-Final Office Action for U.S. Appl. No. 15/643,133 dated Nov. 1, 2019 (9 pages).
Non-Final Office Action for U.S. Appl. No. 15/668,451 dated Dec. 7, 2017 (15 pages).
Non-Final Office Action for U.S. Appl. No. 15/717,675 dated Feb. 14, 2019 (17 pages).
Non-Final Office Action for U.S. Appl. No. 15/785,000 dated Jun. 1, 2018 (10 pages).
Non-Final Office Action for U.S. Appl. No. 15/828,971 dated Jul. 8, 2019 (11 pages).
Non-Final Office Action for U.S. Appl. No. 16/042,904 dated Jul. 12, 2019 (12 pages).
Non-Final Office Action for U.S. Appl. No. 16/184,086 dated Feb. 13, 2020 (10 pages).
Non-Final Office Action for U.S. Appl. No. 16/261,207 dated May 13, 2020 (20 pages).
Non-Final Office Action for U.S. Appl. No. 16/742,082 dated Jan. 11, 2021 (10 pages).
Non-Final Office Action for U.S. Appl. No. 16/742,150 dated Sep. 28, 2021 (18 pages).
Non-Final Office Action for U.S. Appl. No. 16/901,956 dated Mar. 18, 2021 (13 pages).
Non-Final Office Action Response U.S. Appl. No. 11/583,970 dated Jun. 24, 2009 (11 pages).
Non-Final Office Action Response for U.S. Appl. No. 11/583,970 dated Aug. 12, 2008 (12 pages).
Non-Final Office Action Response for U.S. Appl. No. 12/701,383 dated Aug. 25, 2011 (20 pages).
Notice of Acceptance for AU 2009246876 dated Mar. 19, 2015 (3 pages).
Notice of Acceptance for AU 2009274172 dated Aug. 3, 2015 (2 pages).
Notice of Acceptance for AU 2012216462 dated Apr. 10, 2015 (2 pages).
Notice of Allowability for U.S. Appl. No. 15/643,133 dated Sep. 4, 2020 (2 pages).
Notice of Allowability for U.S. Appl. No. 16/184,086 dated Nov. 5, 2020 (2 pages).
Notice of Allowability for U.S. Appl. No. 16/261,207 dated Dec. 23, 2020 (4 pages).
Notice of Allowance for U.S. Appl. No. 11/583,970 dated Aug. 29, 2014 (11 pages).
Notice of Allowance for U.S. Appl. No. 12/467,957 dated Nov. 26, 2014 (7 pages).
Notice of Allowance for U.S. Appl. No. 12/506,894 dated Jun. 16, 2015 (8 pages).
Notice of Allowance for U.S. Appl. No. 12/550,166 date Nov. 26, 2012 (9 pages).
Notice of Allowance for U.S. Appl. No. 12/550,166 dated Apr. 28, 2014 (5 pages).
Notice of Allowance for U.S. Appl. No. 12/701,383 dated May 22, 2015 (9 pages).
Notice of Allowance for U.S. Appl. No. 13/777,967 dated Jul. 14, 2014 (11 pages).
Notice of Allowance for U.S. Appl. No. 13/795,659 dated Mar. 1, 2016 (8 pages).
Notice of Allowance for U.S. Appl. No. 13/795,659 dated Sep. 29, 2015 (11 pages).
Notice of Allowance for U.S. Appl. No. 13/797,648 dated Dec. 6, 2018 (9 pages).
Notice of Allowance for U.S. Appl. No. 14/415,325 dated Jun. 9, 2017 (13 pages).
Notice of Allowance for U.S. Appl. No. 14/461,105 dated Jun. 2, 2017 (7 pages).
Notice of Allowance for U.S. Appl. No. 14/509,870 dated Jun. 22, 2017 (10 pages).
Notice of Allowance for U.S. Appl. No. 14/661,786 dated Apr. 25, 2016 (9 pages).

(56) References Cited

OTHER PUBLICATIONS

Notice of Allowance for U.S. Appl. No. 15/179,735 dated May 29, 2018 (10 pages).
Notice of Allowance for U.S. Appl. No. 15/244,138 dated Jun. 5, 2019 (8 pages).
Notice of Allowance for U.S. Appl. No. 15/643,133 dated May 15, 2020 (8 pages).
Notice of Allowance for U.S. Appl. No. 15/668,451 dated Aug. 10, 2018 (7 pages).
Notice of Allowance for U.S. Appl. No. 15/717,675 dated Sep. 17, 2019 (7 pages).
Notice of Allowance for U.S. Appl. No. 15/785,000 dated Sep. 26, 2018 (7 pages).
Notice of Allowance for U.S. Appl. No. 15/828,971 dated Nov. 1, 2019 (7 pages).
Notice of Allowance for U.S. Appl. No. 16/042,904 dated Dec. 11, 2019 (7 pages).
Notice of Allowance for U.S. Appl. No. 16/042,904 dated Mar. 20, 2020 (7 pages).
Notice of Allowance for U.S. Appl. No. 16/184,086 dated Aug. 26, 2020 (7 pages).
Notice of Allowance for U.S. Appl. No. 16/261,207 dated Nov. 16, 2020 (7 pages).
Notice of Allowance for U.S. Appl. No. 16/742,082 dated Apr. 14, 2021 (6 pages).
Notice of Defects for IL 224494 dated Apr. 23, 2017 (2 pages).
Notice of Defects for IL 232432 dated May 22, 2016.
Notice of Supplementary European Search Report for EP 06826025.6 dated Sep. 1, 2009 (3 pages).
Notification of Defects for IL 190946 dated May 14, 2015, English Translation Only (2 pages).
Notification of Defects for IL 190946 dated Jul. 3, 2012, English Translation Only (1 page).
Notification of Defects for IL 200919 dated Jan. 17, 2013 (4 pages).
Notification of Defects for IL 2053539 dated Jun. 26, 2016.
Notification of Defects for IL 208810 dated Jan. 2, 2013, English Translation Only (4 pages).
Notification of Defects for IL 208810 dated Sep. 18, 2017.
Notification of Defects for IL 209343 dated Aug. 14, 2012 (3 pages).
Notification of Defects for IL 209968 dated Aug. 21, 2012 (4 pages).
Notification of Defects for IL 236763 dated Sep. 17, 2018 (8 pages).
Notification of Defects for IL 241192 dated Dec. 1, 2019 (4 pages).
Notification of Defects for IL 24199 dated Nov. 29, 2017, English Translation Only (2 pages).
Notification of Defects for IL 249700 dated Nov. 18, 2018 (3 pages).
Notification of Defects for IL 249700 dated Nov. 23, 2017 (2 pages).
Notification of Defects for IL 265409 dated Jun. 22, 2020 (8 pages).
Notification of Defects for IL 266009 dated Dec. 25, 2019 (5 pages).
Notification of Defects for IL 272532 dated Jun. 8, 2020 (8 pages).
Notification of Defects for IL 272532 dated Nov. 15, 2020 (8 pages).
Notification of Defects IL 266009 dated Jun. 29, 2020 (3 pages).
Notification of Defects for IL 200919 dated Dec. 5, 2011, English Translation Only (2 pages).
Notification of Detects for IL 266867 dated Oct. 24, 2020 (3 pages).
Notification prior to Allowance for IL 209343 dated Apr. 7, 2014, English Translation Only (2 pages).
Notification Prior to Examination for IL 232432 dated May 15, 2014, English translation only (3 pages).
Notification Prior to Examination for IL 208810 dated Nov. 2, 2011, English Translation Only (3 pages).
Notification Prior to Examination for IL 209343 dated Nov. 2, 2011, English Translation Only (3 pages).
Notification Prior to Examination for IL 209968 dated Nov. 2, 2011, English Translation Only (3 pages).
Notification Prior to Examination for IL 241192 dated Dec. 13, 2015.
Notification Prior to Examination for IL 241299 dated Dec. 15, 2015.
Notification Prior to Examination for IL 264977 dated Feb. 16, 2020.
Notification Prior to Examination for IL 265409 dated Mar. 19, 2019.
Notification Prior to Examination for IL 266867 dated May 10, 2020.
Notification Prior to Examination for IL 272147 dated Nov. 1, 2020.
Notification Prior to Examination for IL 272532 dated Feb. 9, 2020.
Notification Prior to Examination for IL 278426 dated Nov. 4, 2020.
Notification Prior to Examination for IL 278426 dated Sep. 5, 2021.
Notification Prior to Examination for IL 280751 dated Feb. 11, 2021.
Notification Prior to Examination for IL 284998 dated Jul. 22, 2021.
Office Action for EU 201001762/28 dated Oct. 16, 2013, English Translation Only (1 page).
Office Action for IL 190946 dated Apr. 22, 2013, English Translation Only (1 page).
Office Action for IL 200919 dated May 19, 2014, English Translation Only (3 pages).
Office Action for IL 208810 dated Jan. 13, 2015, English Translation Only (3 pages).
Office Action for IL 208810 dated Jun. 27, 2018 (2 pages).
Office Action for IL 209968 dated Jan. 2, 2014, English Translation Only (2 pages).
Office Action for IL 232432 dated Mar. 8, 2015, English Translation Only (3 pages).
Office Action for IL 241192 dated Jul. 30, 2018 (6 pages).
Office Action for IL 256512 dated Jul. 29, 2018 (5 pages).
Office Action for IL 281425 dated Oct. 21, 2021 (3 pages).
Office Action for KR 10-2008-7011791 dated Jan. 15, 2014 (6 pages).
Office Action for KR 10-2008-7011791 dated May 28, 2013 (6 pages).
Office Action for KR 10-2009-7021320 dated Jul. 29, 2011 (7 pages).
Office Action for KR 10-2009-7021320 dated Sep. 18, 2012 (11 pages).
Office Action for KR 10-2010-7028384 dated Aug. 18, 2016 (12 pages).
Office Action for KR 10-2013-7020078 dated Sep. 17, 2014 (8 pages).
Office Action for KR 10-2013-7028338 dated Jan. 15, 2014 (3 pages).
Office Action for MX MX/a/2015/012168 dated Aug. 31, 2018 (5 pages).
Okuyama, et al., "Abotosis and oncogenes", The Medical Frontline, vol. 49, No. 6, 2003, pp. 1096-1101 (13 pages).
Opferman et al., "Anti-apoptotic BCL-2 family members in development", Cell Death and Differentiation, vol. 25, 2018, pp. 37-45, DOI: 10.1038/ckk.2017.170 (9 pages).
Oral Proceedings Summons for EP 08743862.8 dated May 14, 2012 (6 pages).
Ouyang, et al., "Pathophysiology: the Mechanism of Disease and the Basis of Prevention and Treatment", Wuhan University Press, 1st Ed., pp. 128-129 (8 pages).
Pan et al., "Reprogramming human fibroblasts using HIV-1 Tat recombinant proteins OCT4, SOX2, KLF4 and c-MYC", Molecular Biology Reports, vol. 37, 2010, pp. 2117-2124, DOI: 10.1007/s11033-009-9680-6 (8 pages).
Partial Supplementary European Search Report for EP 13820331.0 dated Jun. 30, 2016 (6 pages).
Partial Supplementary European Search Report for EP 14778538.0 dated Jul. 8, 2016 (7 pages).
Patel et al., "The c-MYC Oncoprotein Is a Substrate of the Acetyltransferases hGCN5/PCAF and TIP60", Molecular and Cellular Biology, vol. 24, No. 24, Dec. 2004, pp. 10826-10834, DOI: 10.1128/MCB.24.24.10826-10834.2004 (9 pages).
Patent Examination Report No. 1 for AU 2006304392 dated Jul. 16, 2012 (3 pages).
Patent Examination Report No. 1 for AU 2009246876 dated Jan. 17, 2014 (6 pages).
Patent Examination Report No. 1 for AU 2009274172 dated Jul. 24, 2014 (3 pages).
Patent Examination Report No. 1 for AU 2012216462 dated Mar. 6, 2014 (3 pages).

(56) References Cited

OTHER PUBLICATIONS

Patent Examination Report No. 1 for AU 2014249202 dated Nov. 18, 2015 (2 pages).
Patent Examination Report No. 1 for AU 2015205879 dated Mar. 15, 2016 (9 pages).
Penuela et al., "Erythropoietin reduces storage lesions and decreases apoptosis indices in blood bank red blood cells", Brazilian Journal of Hematology and Hemotherapy, vol. 38, No. 1, 2016, pp. 15-20 (6 pages).
Pierelli et al., "Modulation of bcl-2 and p27 in human primitive proliferating hematopoietic progenitors by autocrine TGF-beta1 is a cell cycle-independent effect and influences their hematopoietic potential," Blood, vol. 95, 2000, pp. 3001-3010 (10 pages).
Pinto Do O et al., "Hematopoietic progenitor/stem cells immortalized by Lhx2 generate functional hematopoietic cells in vivo", Blood, vol. 99, No. 11, 2002, pp. 3939-3946 (9 pages).
Podsypanina et al., "Oncogene cooperation in tumor maintenance and tumor recurrence in mouse mammary tumors induced by Myc and mutant Kras", Proceedings of the National Academy of Sciences, vol. 105, No. 13, 2008, pp. 5242-5247 (6 pages).
Polenakovic et al., "Is Erythropoietin a Survival Factor for Red Blood Cells?" Journal of the American Society of Nephrology, vol. 7,, No. 8, 1996, pp. 1178-1182, DOI: 10.1681/ASN.V781178 (5 pages).
Pollock et al., "A conditionally immortal clonal stem cell line from human cortical neuroepithelium for the treatment of ischemic stroke", Experimental Neurology, vol. 199, No. 1, 2006, pp. 143-155, DOI: 10.1016/j.expneurol.2005.12.011 (13 pages).
Pre-Appeal Examination Report for JP 2014-108137 dated Dec. 7, 2016 (15 pages).
Prochownik et al., "Deregulated expression of c-myc by murine erythroleukaemia cells prevents differentiation", Nature, vol. 322, Aug. 28, 1986, pp. 848-850 (3 pages).
Qin et al., "Nuclear Factor kappaB Nuclear Translocation Upregulates c-Myc and p53 Expression during NMDA Receptor-Mediated Apoptosis in Rat Striatum", The Journal of Neuroscience, vol. 19, No. 10, May 15, 1999, pp. 4023-4033 (11 pages).
Rabbitts et al., "Metabolism of c-myc gene products: c-myc mRNA and protein expression in the cell cycle", The EMBO Journal, vol. 4, No. 8, 1985, pp. 2009-2015 (7 pages).
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270, DOI: 10.1158/0008-5472.CAN-05-3940 (7 pages).
Raymon et al., "Immortalized Human Dorsal Root Ganglion Cells Differentiate into Neurons with Nociceptive Properties", The Journal of Neuroscience, vol. 19, No. 13, 1999, pp. 5420-5428 (9 pages).
Re-Examination Report for AU 2009285547 dated Apr. 23, 2015 (3 pages).
Reason for Refusal for KR 10-2017-7017674 dated Oct. 23, 2017 (12 pages).
Reasons for Refusal for JP 2008-536713 dated Jul. 3, 2012 (6 pages).
Reasons for Refusal for JP 2009-553785 dated Jun. 19, 2012 (7 pages).
Reasons for Refusal for JP 2009-553785 dated Apr. 22, 2014 (10 pages).
Reasons for Refusal for JP 2011-520133 dated Feb. 5, 2014 (9 pages).
Reasons for Refusal for JP 2011-525258 dated Feb. 17, 2014 (8 pages).
Reasons for Refusal for JP 2012-221023 dated Apr. 22, 2014 (4 pages).
Reasons for Refusal for JP 2016-501117 dated Dec. 17, 2018 (4 pages).
Reasons for Refusal for JP 2017-123838 dated Jul. 18, 2018 (6 pages).
Reasons for Refusal for JP 2017-166334 dated Apr. 24, 2019 (6 pages).
Reasons for Refusal for JP 2017-166334 dated Oct. 22, 2018 (7 pages).
Reasons for Refusal for JP 2018-048138 dated Feb. 12, 2019 (6 pages).
Reasons for Refusal for JP 2018-153567 dated Jul. 25, 2019 (8 pages).
Reasons for Refusal for JP 2019-006759 dated Feb. 20, 2020 (5 pages).
Reasons for Refusal for JP 2019-138912 dated Jun. 15, 2020 (7 pages).
Reasons for Refusal for JP 2019-512193 dated May 13, 2020 (6 pages).
Reasons for Refusal for JP 2020-193475 dated Oct. 25, 2021 (4 pages).
Reasons for Rejection for JP 2014-108137 dated Aug. 18, 2015 (12 pages).
Reasons for Rejection for JP 2014-108137 dated Nov. 1, 2017 (13 pages).
Reasons for Rejection for JP 2015-075703 dated Dec. 8, 2016 (6 pages).
Reasons for Rejection for JP 2015-075703 dated May 11, 2016 (11 pages).
Reasons for Rejection for JP 2015-523297 dated Apr. 3, 2017 (8 pages).
Reasons for Rejection for JP 2015-523297 dated Jul. 19, 2017 (8 pages).
Reasons for Rejection for JP 2016-027812 dated Mar. 1, 2017 (9 pages).
Reasons for Rejection for JP 2016-501113 dated Dec. 28, 2017 (13 pages).
Reasons for Rejection for JP 2016-501117 dated Apr. 17, 2017 (11 pages).
Reasons for Rejection for JP 2016-501117 dated Nov. 15, 2017 (9 pages).
Reasons for Rejection for JP 2018-017287 dated Apr. 18, 2019 (13 pages).
Reasons for Rejection for JP 2019-006759 dated Aug. 6, 2020 (4 pages).
Reasons for Rejection for JP 2019-025374 dated Mar. 9, 2020 (8 pages).
Reasons for Rejection for JP 2019-138912 dated Oct. 21, 2020 (6 pages).
Reasons for Rejection for JP 2019-512193 dated Sep. 30, 2019 (8 pages).
Reasons for Rejection for JP 2019-529651 dated Jul. 15, 2020 (6 pages).
Reasons for Rejection for JP 2020-115359 dated Jul. 28, 2021 (6 pages).
Reasons for Rejection for JP 2020-119082 dated Aug. 23, 2021 (6 pages).
Reasons for Rejection for JP 2020-119610 dated Jul. 12, 2021 (6 pages).
Reasons of Refusal for JP 2012-221023 dated Jun. 24, 2014, English Translation Only (2 pages).
Reexamination Notification for CN 201380048261.4 dated May 11, 2021 (16 pages).
Refaeli et al., "The B Cell Antigen Receptor and Overexpression of MYC Can Cooperate in the Genesis of B-Cell Lymphomas", PLOS Biology, vol. 6, Issue 6, e152, 2008, pp. 1208-1225, DOI: 10.1371/journal.pbio.0060152 (18 pages).
Refaeli et al., "The protooncogene MYC can break B cell tolerance", Proceedings of the National Academy of Sciences, vol. 102, No. 11, Mar. 2005, pp. 4097-4102, DOI: 10.1073/pnas.0409832102 (6 pages).
Request for ReExamination for CN 200680045545.8 dated Oct. 12, 2012 (17 pages).
Response for EP 09800871.7 dated Feb. 6, 2013 (9 pages).
Response for EP 09800871.7 dated Jan. 20, 2012 (5 pages).
Response for EP 09800871.7 dated Jul. 10, 2012 (5 pages).
Response for EP 09810692.5 dated Jan. 31, 2012 (7 pages).
Response for EP 09810692.5 dated Jul. 30, 2012 (5 pages).
Response to Final Office Action for U.S. Appl. No. 11/583,970 dated Feb. 16, 2012 (14 pages).

(56) References Cited

OTHER PUBLICATIONS

Response to Final Office Action for U.S. Appl. No. 12/701,383 dated Feb. 15, 2012 (13 pages).
Response to First Office Action for CN 200680045545.8 dated Jul. 15, 2011 (22 pages).
Response to Office Action for JP 2008-536713 dated Oct. 3, 2012 (21 pages).
Response to Second Office Action for CN 200680045545.8 dated Jan. 30, 2012 (23 pages).
Restriction Requirement for U.S. Appl. No. 11/583,970 dated Nov. 13, 2007 (14 pages).
Restriction Requirement for U.S. Appl. No. 12/701,383 dated Jan. 25, 2011 (10 pages).
Richter et al., "Lhx2 expression in hematopoietic progenitor/stem cells in vivo causes a chronic myeloproliferative disorder and altered globin expression", Journal of Hematology, vol. 88, No. 12, 2003, pp. 1336-1347 (12 pages).
Roh et al., "Transgenic Mice for Cre-Inducible Overexpression of the Oncogenes c-MYC and Pim-1 in Multiple Tissues", Genesis: The Journal of Genetics and Development, vol. 44, 2006, pp. 447-453, DOI: 10.1002/dvg.20235 (7 pages).
Rosenwald et al., "Increased expression of eukaryotic translation initiation factors eIF-4E and eIF-2alpha in response to growth induction by c-myc", Proceedings of the National Academy of Sciences USA, vol. 90, 1993, pp. 6175-6178 (4 pages).
Rubinstein et al., "Ex Vivo Interleukin-12-Priming During CD8+ T Cell Activation Dramatically Improves Adoptive T Cell Transfer Antitumor Efficacy in a Lymphodepleted Host", Journal of the American College of Surgeons, vol. 214, No. 4, 2002, pp. 700-707 (8 pages).
Rudolph et al., "Expression of Mad1 in T cells leads to reduced thymic cellularity and impaired mitogen-induced proliferation", Oncogene, vol. 20, 2001, pp. 1164-1175 (12 pages).
Satoh et al, "Roles for c-Myc in Self-renewal of Hematopoietic Stem Cells", The Journal of Biological Chemistry, vol. 279, No. 24, 2004, pp. 24986-24993, DOI: 10.1074/jbc.M400407200 (9 pages).
Sauer, Brian "Inducible Gene Targeting in Mice Using the Cre/lox System", Methods: A Companion to Methods in Enzymology, vol. 14, No. ME980593, 1998, pp. 381-392 (12 pages).
Schiedlmeier et al., "High-level ectopic HOXB4 expression confers a profound in vivo competitive growth advantage on human cord blood CD34+ cells, but impairs lymphomyeloid differentiation", Blood, vol. 101, No. 5, Mar. 1, 2003, pp. 1759-1768, DOI: 10.1182/blood-2002-03- 0767 (10 pages).
Schmidt et al., "Transgenic mice bearing the human c-myc gene activated by an immunoglobulin enhancer: A pre-B-cell lymphoma model", Proceedings of the National Academy of Sciences, vol. 85, Aug. 1988, pp. 6047-6051 (5 pages).
Schneider et al., "Pharmacologic shifting of a balance between protein refolding and degradation mediated by Hsp90", Proceedings of the National Academy of Sciences, Cell Biology, vol. 93, Dec. 1996, pp. 14536-14541 (6 pages).
Schroy et al., "A Simple Method for Freezing and Thawing Cultured Cells," Methods in Cell Science (formerly known as TCA Manual), vol. 2, No. 1, 1976, pp. 309-310 (2 pages).
Schwarze et al., "In vivo protein transduction: intracellular delivery of biologically active proteins, compounds and DNA", Trends in Pharmacological Sciences, vol. 21, Feb. 2000, pp. 45-48 (4 pages).
Schwarze et al., "Protein transduction: unrestricted delivery into all cells?" Trends in Cell Biology, vol. 10, Jul. 2000, pp. 290-295 (6 pages).
Search Report and Written Opinion for SG 10201700459X dated Mar. 9, 2021 (13 pages).
Search Report and Written Opinion for SG 11202000612T dated Jul. 29, 2021 (9 pages).
Search Report for SG 10201700459X dated Feb. 1, 2021 (4 pages).
Second Office Action for CN 200680045545.8 dated Sep. 15, 2011, English Translation Only (9 pages).
Second Office Action for CN 200880015602.7 dated Oct. 31, 2012 (10 pages).
Second Office Action for CN 200980126312.4 dated Aug. 28, 2012 (12 pages).
Second Office Action for CN 200980127166.7 dated Jun. 10, 2013, English Translation Only (1 page).
Second Office Action for CN 201410168106.2 dated May 26, 2016 (5 pages).
Second Office Action for CN 201410479865.2 dated Jul. 5, 2016 (6 pages).
Second Office Action for CN 201480026147.6 dated Apr. 20, 2017 (11 pages).
Second Office Action for CN 201480026500.0 dated Apr. 27, 2018 (5 pages).
Second Office Action for Cn 201510760532.X dated Jan. 10, 2020 (14 pages).
Second Office Action for CN 201780082261.4 dated Feb. 26, 2021 (5 pages).
Seibutsugaku Jiten (Dictionary of Biology), Iwanami Shoten, The 4th edition, 1997, p. 1396 (2 pages).
Siebenlist et al., "*E. coli* RNA Polymerase Interacts Homologously with Two Different Promoters", Cell, vol. 20, Jun. 1980, pp. 269-281 (13 pages).
Silva et al., "Erythropoietin Can Promote Erythroid Progenitor Survival by Repressing Apoptosis Through Bcl-XL and Bcl-2", Blood, vol. 88, No. 5, Sep. 1, 1996, pp. 1576-1582 (8 pages).
Sipione et al., "Modeling Brain Pathologies Using Neural Stem Cells", Methods in Molecular Biology, vol. 198, 2002, pp. 245-262 (18 pages).
Snyder et al., "Regulation of NMDA receptor trafficking by amyloid-beta", Nature Neuroscience, 2005, vol. 8, No. 8, pp. 1051-1058, DOI: 10.1038/nn1503 (8 pages).
Soane et al., "TAT-mediated endocytotic delivery of the loop deletion Bcl-2 protein protects neurons against cell death", Journal of Neurochemistry, vol. 95, 2005, pp. 230-243, DOI: 10.1111/j.1471-4159.2005.03359.x (14 pages).
Song, "Cloning and expression of PTD-BDNF fusion gene and purification of expressed product", Bioengineering Pharmaceutical Research and Practice, Anhui Science and Technology Press, 1st Ed., Feb. 2009, pp. 200-201 (3 pages).
Stein et al., "TAT-MYC Recombinant Fusion Protein Enhances Hematopoietic Stem Cell Graft Performance and Immunne Cell Reconstitution after Transplantation," Blood, vol. 130, Suppl. 1, Dec. 7, 2017, pp. 3175 (2 pages).
Stevenson et al., "HIV-1 replication is controlled at the level of T cell activation and proviral integration", The EMBO Journal, vol. 9, No. 5, 1990, pp. 1551-1560 (10 pages).
Strasser et al., "Novel primitive lymphoid tumours induced in transgenic mice by cooperation between myc and bcl-2", Letters to Nature, vol. 348, 1990, pp. 331-333 (3 pages).
Sunyer, J. Oriol, "Evolutionary and Functional Relationships of B Cells from Fish and Mammals: Insights into their Novel Roles in Phagocytosis and Presentation of Particulate Antigen", Infectious Disorders—Drug Targets, vol. 12, No. 3, 2012, pp. 200-212 (24 pages).
Supplementary European Search Report for EP 08743862.8 dated Mar. 31, 2010 (1 page).
Taguchi et al., "Nuclear trafficking of macromolecules by an oligopeptide derived from Vpr of human immunodeficiency virus type-1", Biochemical and Biophysical Research Communications, vol. 320, No. 1, 2004, pp. 18-26 (10 pages).
Takahashi et al., Induction of Pluripotent Stem Cells from Mouse Embryonic and Adult Fibroblast Cultures by Defined Factors, Cell, vol. 126, Aug. 2006, pp. 663-676, DOI: 10.1016/j.cell.2006.07.024 (14 pages).
Theis et al., "Expression of the myc/His-Tagged Human Peptide Transporter hPEPT1 in Yeast for Protein Purification and Functional Analysis", Protein Expression and Purification, 2001, vol. 22, pp. 436-442 (7 pages).
Third Office Action for CN 200680045545.8 dated Feb. 15, 2015, English Translation Only (4 pages).
Third Office Action for CN 200880015602.7 dated May 9, 2013 (13 pages).
Third Office Action for CN 200980127166.7 dated Apr. 11, 2014 (6 pages).

(56) References Cited

OTHER PUBLICATIONS

Third Office Action for CN 201410168106.2 dated Nov. 28, 2016 (11 pages).
Third Office Action for CN 201480026147.6 dated Sep. 28, 2017 (5 pages).
Third Office Action for CN 201510760532.X Jul. 13, 2020 (12 pages).
Thomas et. al., "Progress and Problems with the Use of Viral Vectors for Gene Therapy", Nature, vol. 4, May 2003, pp. 346-358, DOI: 10.1038/nrg1066 (13 pages).
Trumpp et al., "c-Myc regulates mammalian body size by controlling cell number but not cell size", Nature, vol. 414, Dec. 2001, pp. 768-773 (6 pages).
Tsai et al., "Lymphohematopoietic progenitors immortalized by a retroviral vector harboring a dominant-negative retinoic acid receptor can recapitulate lymphoid, myeloid, and erythroid development", Genes & Development, vol. 8, 1994, pp. 2831-2841, DOI: 10.1101/gad.8.23.2831 (12 pages).
Varnum-Finney et al., "Pluripotent, cytokine-dependent, hematopoietic stem cells are immortalized by constitutive Notch1 signaling", Nature Medicine, vol. 6, No. 11, 2000, pp. 1278-1281 (4 pages).
Vaux et al., "Bcl-2 gene promotes hemopoietic cell survival and cooperates with c-myc to immortalize pre-B cells", Nature, vol. 335, Sep. 29, 1988, pp. 440-442 (3 pages).
Vaux et al., "Immunologic competence of B cells subjected to constitutive c-myc oncogene expression in immunoglobulin heavy chain enhancer myc transgenic mice", The Journal of Immunology, vol. 139, No. 11, Dec. 1987, pp. 3854-3860 (7 pages).
Wagner et al., "Myc-Mediated Apoptosis Is Blocked by Ectopic Expression of Bcl-2", Molecular and Cellular Biology, vol. 13, No. 4, Apr. 1993, pp. 2432-2440 (9 pages).
Wang et al., "Primitive Human Hematopoietic Cells Are Enriched in Cord Blood Compared With Adult Bone Marrow or Mobilized Peripheral Blood as Measured by the Quantitative In Vivo SCID-Repopulating Cell Assay", Blood, vol. 89, 1997, pp. 3919-3924 (6 pages).
Wang, Wei, "Instability, stabilization, and formulation of liquid protein pharmaceuticals", International Journal of Pharmaceutics, vol. 185, Issue 2, Aug. 20, 1999, pp. 129-188 (60 pages).
Wang, Wei, "Lyophilization and development of solid protein pharmaceuticals", International Journal of Pharmaceutics, vol. 203, Issues 1-2, Aug. 2000, pp. 1-60 (60 pages).
Watt et al., "Nucleotide sequence of cloned cDNA of human c-myc oncogene", Nature, vol. 303, 1983, pp. 725-728 (4 pages).
Wechsler et al., "MXI1, a Putative Tumor Suppressor Gene, Suppresses Growth of Human Glioblastoma Cells", Cancer Research, vol. 57, 1997, pp. 4905-4912 (8 pages).
Wilson et al., "c-Myc controls the balance between hematopoietic stem cell self-renewal and differentiation", Genes and Development, vol. 18, 2004, pp. 2747-2763, DOI: 10.1101/gad.313104 (18 pages).
Wu et al., "Fusion Protein Vectors to Increase Protein Production and Evaluate the Immunogenicity of Genetic Vaccines", Molecular Therapy, vol. 2, No. 3, Sep. 2000, pp. 288-297, DOI: 10.1006/mthe.2000.0126 (10 pages).
Wu et al., "Inhibition of c-myc Expression Induces Apoptosis of WEHI 231 Murine B Cells", Molecular and Cellular Biology, vol. 16, No. 9, Sep. 1996, pp. 5015-5025 (11 pages).
Wurm et al., "Large-scale transient expression of mammalian cells for recombinant protein production", Current Opinion in Biotechnology, vol. 10, 1999, pp. 156-159 (4 pages).
Xi et al., "In Vitro Large Scale Production of Human Mature Red Blood Cells from Hematopoietic Stem Cells by Coculturing with Human Fetal Liver Stromal Cells", BioMed Research International, vol. 2013, Article ID 807863, Jan. 30, 2013, DOI: 10.1155/2013/807863 (12 pages).

Xu Zhixiang, et al, "The Development of the Study On the Anti-Tumor Effect of Flt3 Ligand," Chinese Journal of Tumor Biological Therapy, vol. 7, No. 3, Sep. 30, 2000 (2 pages).
Yagihashi et al., "Detection of Anti-Survivin Antibody in Gastrointestinal Cancer Patients", Clinical Chemistry, vol. 47, No. 9, Sep. 2001, pp. 1729-1731, DOI: doi.org/10.1093/clinchem/47.9.1729 (3 pages).
Yakuzaigaku, Pharmaceutics, vol. 64, No. 3, 2004, pp. 164-167 (4 pages).
Yanai et al., "A novel stromal cell-dependent hematopoietic cell line established from temperature-sensitive SV40 T-antigen transgenic mice", Experimental Hematology, vol. 27, 1999, pp. 1087-1096 (10 pages).
Young et al., "B-cell receptor signaling in the genesis and maintenance of B-cell lymphoma", Future Oncology, vol. 4, No. 5, 2008, pp. 591-594, DOI: 10.2217/14796694.4.5.591 (4 pages).
Yu et al., "Oncology Clinical Bulletin", Shandong Science and Technology Press, 2004 (28 pages).
Zhang et al., "Cytokines regulating hematopoietic stem cell function", Current Opinion in Hematology, vol. 15, No. 4, Jul. 2008, pp. 307-311, DOI: 10.1097/MOH.0b013e3283007db5 (8 pages).
Zhang et al., "Reprogramming of somatic cells via TAT-mediated protein transduction of recombinant factors", Biomaterials, vol. 33, 2012, pp. 5047-5055, DOI: 10.1016/j.biomaterials.2012.03.061 (9 pages).
Zhuang et al., "C-MYC overexpression is required for continuous suppression of oncogene-induced senescence in melanoma cells", Oncogene, vol. 27, 2008, pp. 6623-6634 (12 pages).
Yu et al., "Molecular Biology" (in Chinese), Nanjing Normal University Press, Jul. 2007, pp. 158 and 159 (English Translation).
Zhu et al., "Modern Molecular Biology" (in Chinese), Higher Education Press, Mar. 1997, p. 422 (English Translation).
Caron, et al., "Intracellular Delivery of a Tat-eGFP Fusion Protein into Muscle Cells." Molecular Therapy, Mar. 2001, vol. 3, No. 3, pp. 310-318.
Chandran, et al., "Tumor-Specific Effector CD8 T Cells That Can Establish Immunological Memory in Humans after Adoptive Transfer Are Marked by Expression of IL7 Receptor and c-myc." Cancer Res. Aug. 15, 2015, vol. 75, No. 16, pp. 3216-3226.
Deleeuw, et al., "CD25 Identifies a Subset of CD4 FoxP3-TIL That Are Exhausted Yet Prognostically Favorable in Human Ovarian Cancer." Cancer Immunol. Res. Mar. 1, 2015, vol. 3, No. 3, pp. 245-253.
Non-Final Office Action on U.S. Appl. No. 16/598,690 Dtd Mar. 1, 2022.
Non-Final Office Action on U.S. Appl. No. 16/635,383 Dtd Feb. 18, 2022.
Vives, et al., "A Truncated HIV-1 Tat Protein Basic Domain Rapidly Translocates through the Plasma Membrane and Accumulates in the Cell Nucleus." Journal of Biol. Chemistry. Jun. 20, 1997, vol. 272, No. 25, pp. 16010-16017.
Wold et al., "Antibody Therapeutics in Oncology", Immunotherapy, Mar. 2016, pp. 1-18, vol. 2, No. 1.
Office Action issued in Canadian Application No. 2905296 dated Feb. 15, 2022.
European Communication pursuant to Article 94(3) issued in European Application No. 19157513.3 dated Mar. 3, 2022.
Notice of Reasons for Rejection issued in Japanese Application No. 2021-037508, dated Mar. 31, 2022, English Translation.
Hann, et al., "The alternatively initiated c-Myc proteins differentially regulate transcription through a noncanonical DNA-binding site." Genes & Development, 1994, No. 8, pp. 2441-2452.
Non-Final Office Action on U.S. Appl. No. 16/635,383 dated Jun. 29, 2022.

\* cited by examiner

COMPOSITIONS AND METHODS FOR THE CRYOPRESERVATION OF IMMUNE CELLS

CROSS-REFERENCE TO RELATED APPLICATIONS

This application is a national phase of International Application No. PCT/US2020/027070, filed Apr. 7, 2020, which claims the benefit of priority to U.S. Provisional Patent Application No. 62/830,950, filed Apr. 8, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 4, 2021, is named 106417-0572_Sequence_Listing.txt and is 22,016 bytes in size.

TECHNICAL FIELD

The present technology relates to compositions and methods for the cryopreservation of immune cells, such as peripheral blood mononuclear cells (PBMCs) by pre-treating the cells with a PTD-MYC fusion protein (e.g., an HIV TAT-MYC fusion polypeptide) prior to freezing. Kits for use in practicing the methods are also provided herein.

BACKGROUND

Cryopreservation is a process in which cells are preserved by cooling them to low temperatures. At these low temperatures, biological activity, including the biochemical reactions that would lead to cell death under normal conditions, are effectively stopped. However, if not properly controlled, cryopreservation can lead to cell damage and a decrease in cell viability. Further, after the freeze-thaw process, cells normally need to be cultured to ensure proper recovery. Currently, there is an unmet need for cryopreservation methods that increase cell viability and recovery after the cryopreserved cells have thawed.

SUMMARY

In one aspect, the present disclosure provides a frozen composition that includes (a) a MYC fusion polypeptide, comprising (i) a protein transduction domain, (ii) a MYC polypeptide sequence; and (b) one or more peripheral blood mononuclear cells (PBMCs) isolated from a donor subject, wherein the composition exhibits increased cell viability compared to control PBMC cells isolated from the subject. In some embodiments, the protein transduction domain sequence is a TAT protein transduction domain sequence. In some embodiments, the protein transduction domain is $TAT_{[48-57]}$. In some embodiments, the protein transduction domain is $TAT_{[57-48]}$. In some embodiments, the MYC fusion polypeptide comprises SEQ ID NO: 1. In some embodiments, the one or more peripheral blood mononuclear cells comprises a T-cell, a B-cell, an NK cell, a monocyte, a granulocyte, a macrophage, or any combination thereof. In some embodiments, the compositions further include a cell suspension medium. In some embodiments, the cell suspension medium comprises CHB media, CS5 media, or CS10 media. In some embodiments, the composition exhibits increased cell recovery when thawed as compared to control PBMCs in the absence of the MYC fusion polypeptide after a freeze-thaw cycle. In some embodiments, the composition exhibits increased expression of CD25 after cell activation as compared to control PBMCs in the absence of the MYC fusion polypeptide after a freeze-thaw cycle. In some embodiments, the present disclosure provides an immune cell bank comprising the frozen composition.

In one aspect, the present disclosure provides a method of cryopreserving peripheral blood mononuclear cells (PBMCs) that includes (a) contacting a composition comprising one or more PBMCs isolated from a donor subject with an effective amount of a MYC fusion polypeptide, comprising (i) a protein transduction domain; (ii) a MYC polypeptide sequence; and (b) cooling the PBMCs to a temperature sufficient to freeze the composition. In some embodiments, the protein transduction domain sequence is a TAT protein transduction domain sequence. In some embodiments, the protein transduction domain is $TAT_{[48-57]}$. In some embodiments, the protein transduction domain is $TAT_{[57-48]}$. In some embodiments, the MYC fusion polypeptide comprises SEQ ID NO: 1. In some embodiments, the one or more peripheral blood mononuclear cells comprises a T-cell, a B-cell, an NK cell, a monocyte, a granulocyte, or any combination thereof. In some embodiments, the method further includes suspending the PBMCs in a cell suspension medium. In some embodiments, the cell suspension medium comprises CHB media, CS5 media, or CS10 media.

In some embodiments, the composition comprising one or more PBMCs is contacted with the MYC fusion polypeptide at a concentration of about 0.5 µg/mL to about 500 µg/mL. In some embodiments, the composition comprising one or more PBMCs is contacted with the MYC fusion polypeptide at a concentration of about 0.5 µg/mL to about 10 µg/mL. In some embodiments, the composition comprising one or more PBMCs is contacted with the MYC fusion polypeptide for less than 24 hours prior to step (b). In some embodiments, the composition comprising one or more PBMCs is contacted with the MYC fusion polypeptide for about 1 hour prior to step (b). In some embodiments, the PBMCs are washed following step (a) and prior to step (b).

In some embodiments, the PBMCs are cooled using a controlled-rate cryogenic freezer. In some embodiments, the PBMCs are cooled at a rate of about −1° C. per min. In some embodiments, the temperature sufficient to freeze the composition is about −80° C. to about −190° C.

In some embodiments, the method further includes thawing of the cryopreserved cells, such that the cells exhibit one or more of increased cell viability, increased cell recovery, cell activation, or increased expression of CD25 after cell activation as compared to control PBMCs not contacted with an effective amount of the MYC fusion polypeptide.

Also provided herein are method of using cells that have been cryopreserved using a MYC fusion polypeptide.

Also provided herein are kits comprising the MYC fusion polypeptides, the MYC fusion polypeptide-modified immune cells, and/or the frozen composition of the present technology of any embodiment described herein and instructions for use.

In one aspect, the present disclosure provides an immune cell bank comprising: (a) a MYC fusion polypeptide, comprising (i) a protein transduction domain; (ii) a MYC polypeptide sequence; and (b) one or more peripheral blood mononuclear cells (PBMCs) isolated from a donor subject.

DETAILED DESCRIPTION

Figure 1:
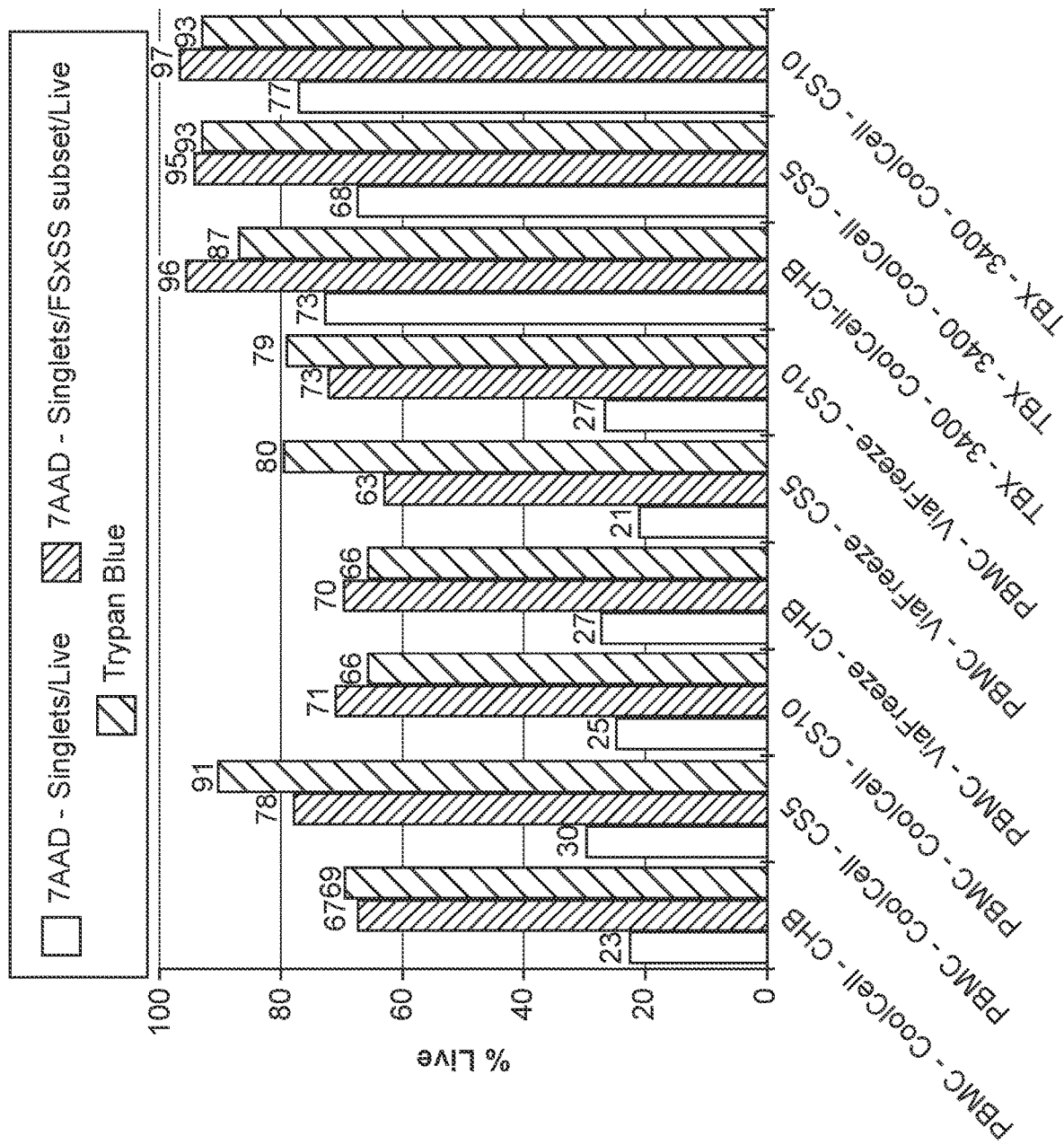
FIG. 1 illustrates the cell viability of immune cells (e.g., peripheral blood mononuclear cells (PBMC)), following pre-treatment with a PTD-MYC fusion polypeptide (TBX-3400) or vehicle control (PBMC), cryopreservation under various conditions, and thawing. Cells were stained with either 7-aminoactinomycin D (7-AAD) or trypan blue and analyzed via flow cytometry or hemocytometer to determine the extent of viable cells after thawing. Cells were frozen in CHB media, CS5 media, or CS10 media as indicated, and frozen in a CoolCell® container of VIA Freeze™ controlled rate freezer.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Unless defined otherwise, all technical and scientific terms used herein have the same meaning as commonly understood by one of ordinary skill in the art to which this disclosure belongs.

I. Definitions

The terminology used herein is for the purpose of describing particular embodiments only and is not intended to be limiting of the disclosure. As used herein, the singular forms "a", "an", and "the" are intended to include the plural forms as well, unless the context clearly indicates otherwise.

As used herein, the term "about" means that a value can vary +/−20%, +/−15%, +/−10% or +/−5% and remain within the scope of the present disclosure. For example, "a concentration of about 200 IU/mL" encompasses a concentration between 160 IU/mL and 240 IU/mL.

As used herein, the term "administration" of an agent to a subject includes any route of introducing or delivering the agent to a subject to perform its intended function. Administration can be carried out by any suitable route, including intravenously, intramuscularly, intraperitoneally, or subcutaneously. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein the term immune cell refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

The term "lymphocyte" refers to all immature, mature, undifferentiated and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells and anergic AN1/T3 cell populations.

As used herein, the term T-cell includes naïve T cells, CD4+ T cells, CD8+ T cells, memory T cells, activated T cells, anergic T cells, tolerant T cells, chimeric T cells, antigen-specific T cells, and regulatory T cells.

The term "B cell" or "B cells" refers to, by way of non-limiting example, a pre-B cell, progenitor B cell, early pro-B cell, late pro-B cell, large pre-B cell, small pre-B cell, immature B cell, mature B cell, naïve B cells, plasma B cells, activated B cells, anergic B cells, tolerant B cells, chimeric B cells, antigen-specific B cells, memory B cell, B-1 cell, B-2 cells and anergic AN1/T3 cell populations. In some embodiments, the term B cell includes a B cell that expresses an immunoglobulin heavy chain and/or light chain on its cells surface. In some embodiments, the term B cell includes a B cell that expresses and secretes an immunoglobulin heavy chain and/or light chain. In some embodiments, the term B cell includes a cell that binds an antigen on its cell-surface. In some embodiments disclosed herein, B cells or AN1/T3 cells are utilized in the processes described. In certain embodiments, such cells are optionally substituted with any animal cell suitable for expressing, capable of expressing (e.g., inducible expression), or capable of being differentiated into a cell suitable for expressing an antibody including, e.g., a hematopoietic stem cell, a naïve B cell, a B cell, a pre-B cell, a progenitor B cell, an early Pro-B cell, a late pro-B cell, a large pre-B cell, a small pre-B cell, an immature B cell, a mature B cell, a plasma B cell, a memory B cell, a B-1 cell, a B-2 cell, an anergic B cell, or an anergic AN1/T3 cell.

As used herein, "peripheral blood mononuclear cells" refers to any peripheral blood cells having a round nucleus, including lymphocytes, such as T cells, B cells, NK cells, monocytes, macrophages and dendritic cells.

As used herein "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (i.e., heterologous T-cell receptor) modified lymphocytes and CAR (i.e., chimeric antigen receptor) modified lymphocytes. In another embodiment, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells (PBMC). In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells. In one embodiment, the adoptive cell therapeutic composition may be a frozen composition comprising one or more immune cells and/or PBMCs isolated from a donor subject which have been contacted with a MYC fusion polypeptide, comprising (i) a protein transduction domain; (ii) a MYC polypeptide sequence.

The terms "MYC" and "MYC gene" are synonyms. They refer to a nucleic acid sequence that encodes a MYC polypeptide. A MYC gene comprises a nucleotide sequence of at least 120 nucleotides that is at least 60% to 100% identical or homologous, e.g., at least 60, 65%, 70%, 75%, 80%, 85%, 86%, 87%, 88%, 90%, 91%, 92%, 94%, 95%, 96%, 97%, 98%, or any other percent from about 70% to about 100% identical to sequences of NCBI Accession Number NM-002467. In some embodiments, the MYC gene is a proto-oncogene. In certain instances, a MYC gene is found on chromosome 8, at 8q24.21. In certain instances, a MYC gene begins at 128,816,862 bp from pter and ends at 128,822,856 bp from pter. In certain instances, a MYC gene is about 6 kb. In certain instances, a MYC gene encodes at least eight separate mRNA sequences-5 alternatively spliced variants and 3 unspliced variants.

The terms "MYC protein," "MYC polypeptide," and "MYC sequence" are synonyms and refer to the polymer of amino acid residues disclosed in NCBI Accession Number UniProtKB/Swiss-Prot:P01106.1 (MYC isoform 1) or NP_002458.2 (UniProtKB/Swiss-Prot:P01106.2; MYC isoform 2), and functional homologs, analogs or fragments thereof. The sequence of or UniProtKB/Swiss-Prot: P01106.1 is:

(SEQ ID NO: 2)
MPLNVSFTNRNYDLDYDSVQPYFYCDEEENFYQQQQQSELQPPAPSEDI

WKKFELLPTPPLSPSRRSGLCSPSYVAVTPFSLRGDNDGGGGSFSTADQ

LEMVTELLGGDMVNQSFICDPDDETFIKNIIIQDCMWSGFSAAAKLVSE

KLASYQAARKDSGSPNPARGHSVCSTSSLYLQDLSAAASECIDPSVVFP

YPLNDSSSPKSCASQDSSAFSPSSDSLLSSTESSPQGSPEPLVLREETP

PTTSSDSEEEQEDEEEIDVVSVEKRQAPGKRSESGSPSAGGHSKPPHSP

LVLKRCHVSTHQHNYAAPPSTRKDYPAAKRVKLDSVRVLRQISNNRKCT

SPRSSDTEENVKRRTHNVLERQRRNELKRSFFALRDQIPELENNEKAPK

VVILKKATAYILSVQAEEQKLISEEDLLRKRREQLKHKLEQLRNSCA

The sequence of NP_002458.2 (UniProtKB/Swiss-Prot: P01106.2) is:

(SEQ ID NO: 11)
MDFFRVVENQQPPATMPLNVSFTNRNYDLDYDSVQPYFYCDEEENFYQQ

QQQSELQPPAPSEDIWKKFELLPTPPLSPSRRSGLCSPSYVAVTPFSLR

GDNDGGGGSFSTADQLEMVTELLGGDMVNQSFICDPDDETFIKNIIIQD

CMWSGFSAAAKLVSEKLASYQAARKDSGSPNPARGHSVCSTSSLYLQDL

SAAASECIDPSVVFPYPLNDSSSPKSCASQDSSAFSPSSDSLLSSTESS

PQGSPEPLVLREETPPTTSSDSEEEQEDEEEIDVVSVEKRQAPGKRSES

GSPSAGGHSKPPHSPLVLKRCHVSTHQHNYAAPPSTRKDYPAAKRVKLD

SVRVLRQISNNRKCTSPRSSDTEENVKRRTHNVLERQRRNELKRSFFAL

RDQIPELENNEKAPKVVILKKATAYILSVQAEEQKLISEEDLLRKRREQ

LKIAKLEQLRNSCA

In some embodiments, the MYC polypeptide is a complete MYC polypeptide sequence. In some embodiments, the MYC polypeptide is a partial MYC polypeptide sequence. In some embodiments, the MYC polypeptide comprises at least 400 consecutive amino acids of SEQ ID NO: 2 OR 11. In some embodiments, the MYC polypeptide comprises at least 400 consecutive amino acids of SEQ ID NO: 2 OR 11 and retains at least one MYC activity. In some embodiments, the MYC polypeptide comprises at least 400, at least 410, at least 420, at least 430, or at least 450 consecutive amino acids of SEQ ID NO: 2 OR 11. In some embodiments, the MYC polypeptide comprises at least 400, at least 410, at least 420, at least 430, or at least 450 consecutive amino acids of SEQ ID NO: 2 OR 11 and retains at least one MYC activity. In some embodiments, the MYC polypeptide is c-MYC. In some embodiments, the MYC polypeptide sequence comprises the sequence shown below:

(SEQ ID NO: 3)
MDFFRVVENQQPPATMPLNVSFTNRNYDLDYDSVQPYFYCDEEENFYQQ

QQQSELQPPAPSEDIWKKFELLPTPPLSPSRRSGLCSPSYVAVTPFSLR

GDNDGGGGSFSTADQLEMVTELLGGDMVNQSFICDPDDETFIKNIIIQD

CMWSGFSAAAKLVSEKLASYQAARKDSGSPNPARGHSVCSTSSLYLQDL

SAAASECIDPSVVFPYPLNDSSSPKSCASQDSSAFSPSSDSLLSSTESS

PQGSPEPLVLREETPPTTSSDSEEEQEDEEELDVVSVEKRQAPGKRSES

GSPSAGGHSKPPHSPLVLKRCHVSTHQHNYAAPPSTRKDYPAAKRVKLD

SVRVLRQISNNRKCTSPRSSDTEENVKRRTHNVLERQRRNELKRSFFAL

RDQIPELENNEKAPKVVILKKATAYILSVQAEEQKLISEEDLLRKRREQ

LKEIKLEQLR.

In some embodiments, the MYC polypeptide sequence comprises the sequence shown below:

(SEQ ID NO: 4)
PLNVSFTNRNYDLDYDSVQPYFYCDEEENFYQQQQQSELQPPAPSEDIW

KKFELLPTPPLSPSRRSGLCSPSYVAVTPFSLRGDNDGGGGSFSTADQL

EMVTELLGGDMVNQSFICDPDDETFIKNIIIQDCMWSGFSAAAKLVSEK

LASYQAARKDSGSPNPARGHSVCSTSSLYLQDLSAAASECIDPSVVFPY

PLNDSSSPKSCASQDSSAFSPSSDSLLSSTESSPQGSPEPLVLREETPP

TTSSDSEEEQEDEEEIDVVSVEKRQAPGKRSESGSPSAGGHSKPPHSPL

VLKRCHVSTHQHNYAAPPSTRKDYPAAKRVKLDSVRVLRQISNNRKCTS

PRSSDTEENVKRRTHNVLERQRRNELKRSFFALRDQIPELENNEKAPKV

VILKKATAYILSVQAEEQKLISEEDLLRKRREQLKIAKLEQLR.

In some embodiments, a MYC polypeptide comprises an amino acid sequence that is at least 40% to 100% identical, e.g., at least 40%, 45%, 50%, 55%, 60%, 65%, 70%, 75%, 80%, 81%, 82%, 83%, 84%, 85%, 86%, 87%, 88%, 90%, 91%, 92%, 94%, 95%, 96%, 97%, 98%, 99%, or any other percent from about 40% to about 100% identical to the sequence of NCBI Accession Number NP002458.2 or Uni- ProtKB/Swiss-Prot Accession Number P01106.1. In some embodiments, MYC polypeptide refers to a polymer of 439 amino acids, a MYC polypeptide that has not undergone any post-translational modifications. In some embodiments, MYC polypeptide refers to a polymer of 439 amino acids that has undergone post-translational modifications. In some embodiments, the MYC polypeptide is 48,804 kDa. In some embodiments, the MYC polypeptide contains a basic Helix-Loop-Helix Leucine Zipper (bHLH/LZ) domain. In some embodiments, the bHLH/LZ domain comprises the sequence of: ELKRSFFALRDQIPELENNEKAPKVVILK-KATAYILSVQAEEQKLISEEDLLRKRREQLKH KLEQLR (SEQ ID NO: 5). In some embodiments, the MYC polypeptide is a transcription factor (e.g., Transcription Factor 64). In some embodiments, the MYC polypeptide contains an E-box DNA binding domain. In some embodiments, the MYC polypeptide binds to a sequence comprising CACGTG. In some embodiments, the MYC polypeptide promotes one or more of cell survival and/or proliferation. In some embodiments, a MYC polypeptide includes one or more of those described above, and includes one or more post-translational modifications (e.g., acetylation). In some embodiments, the MYC polypeptides comprise one or more additional amino acid residues at the N-terminus or C-terminus of the polypeptide. In some embodiments, the MYC polypeptides are fusion proteins. In some embodiments, the MYC polypeptides are linked to one or more additional peptides at the N-terminus or C-terminus of the polypeptide.

Proteins suitable for use in the methods described herein also includes functional variants, including proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions can be conservative amino acid substitutions. Among the common, naturally occurring amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al (1992), *Proc. Natl Acad. Sci. USA*, 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The phrases "E-box sequence" and "enhancer box sequence" are used interchangeably herein and mean the nucleotide sequence CANNTG, wherein N is any nucleotide. In certain instances, the E-box sequence comprises CACGTG. In certain instances, the basic helix-loop-helix domain of a transcription factor encoded by MYC binds to the E-box sequence. In certain instances, the E-box sequence is located upstream of a gene (e.g., p21, Bcl-2, or ornithine decarboxylase). In certain instances, the MYC polypeptide contains an E-box DNA binding domain. In certain instances, the E-box DNA binding domain comprises the sequence of KRRTHNVLERQRRN (SEQ ID NO: 6). In certain instances, the binding of the transcription factor encoded by MYC to the E-box sequence, allows RNA polymerase to transcribe the gene downstream of the E-box sequence.

The term "MYC activity" or "MYC biological activity" or "biologically active MYC" includes one or more of enhancing or inducing cell survival, cell proliferation, and/or antibody production. By way of example and not by way of limitation, MYC activity includes enhancement of expansion of anti-CD3 and anti-CD28 activated T-cells and/or increased proliferation of long-term self-renewing hematopoietic stem cells. MYC activity also includes entry into the nucleus of a cell, binding to a nucleic acid sequence (e.g., binding an E-box sequence), and/or inducing expression of MYC target genes.

The terms "patient," "subject," "individual," and the like are used interchangeably herein, and refer to an animal, typically a mammal. In one embodiment, the patient, subject, or individual is a mammal. In one embodiment, the patient, subject or individual is a human. In some embodiments the patient, subject or individual is an animal, such as, but not limited to, domesticated animals, such as equine, bovine, murine, ovine, canine, and feline.

The terms "protein transduction domain (PTD)" or "transporter peptide sequence" (also known as cell permeable proteins (CPP) or membrane translocating sequences (MTS)) are used interchangeably herein to refer to small peptides that are able to ferry much larger molecules into cells independent of classical endocytosis. In some embodiments, a nuclear localization signal can be found within the protein transduction domain, which mediates further translocation of the molecules into the cell nucleus.

The terms "treating" or "treatment" as used herein covers the treatment of a disease in a subject, such as a human, and includes: (i) inhibiting a disease, i.e., arresting its development; (ii) relieving a disease, i.e., causing regression of the disease; (iii) slowing progression of the disease; and/or (iv) inhibiting, relieving, or slowing progression of one or more symptoms of the disease. With respect to a tumor, "treating" or "treatment" also encompasses regression of a tumor, slowing tumor growth, inhibiting metastasis of a tumor, inhibiting relapse or recurrent cancer and/or maintaining remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment can be a continuous prolonged treatment for a chronic disease or a single, or few time administrations for the treatment of an acute condition.

The term "therapeutic" as used herein means a treatment and/or prophylaxis. A therapeutic effect is obtained by suppression, remission, or eradication of a disease state.

II. Overview

In one aspect, the present disclosure relates to, in part, to the cryopreservation of a composition comprising one or more immune cells (e.g., peripheral blood mononuclear cells (PBMC)) isolated from a donor subject, wherein the one or more immune cells are contacted with an effective amount of a PTD-MYC fusion polypeptide in vitro prior to cooling the composition to a temperature sufficient to freeze the composition.

In another aspect, the present disclosure relates to, in part, to the cryopreservation of a composition comprising one or more peripheral blood mononuclear cells (PBMCs) isolated from a donor subject, wherein the one or more PBMCs are contacted with an effective amount of a PTD-MYC fusion polypeptide in vitro prior to cooling the cooling the composition to a temperature sufficient to freeze the composition.

The present disclosure is based, at least in part, on the discovery, that contacting one or more immune cells and/or PBMCs isolated from a donor subject with a MYC fusion polypeptide containing a MYC polypeptide and a protein transduction domain (PTD), such as the HIV TAT protein transduction domain, and cooling the treated immune cells and/or PBMCs to a temperature sufficient to freeze the cells significantly increases cell viability and/or cell recovery, as well as significantly increases expression of CD25 after cell activation compared to control immune cells and/or PBMCs not treated with the MYC fusion polypeptide. The examples provided herein demonstrate that immune cells and/or PBMCs isolated from donor subjects which have been contacted with a TAT-MYC fusion protein prior to cryopreservation exhibit one or more of increased cell viability, increased cell recovery, increased cell activation with CD3 and CD28, or increased expression of CD25 upon cell activation when thawed as compared to control PBMCs after a freeze-thaw cycle.

In some embodiments, the present disclosure provides a method for cryopreserving immune cells, the method comprising contacting a composition comprising one or more PBMCs isolated from a donor subject with an effective amount of a MYC fusion polypeptide, comprising (i) a protein transduction domain (PTD); (ii) a MYC polypeptide sequence, and cooling the PBMCs to a temperature sufficient to freeze the composition.

In some embodiments, the present disclosure provides a method for cryopreserving peripheral blood mononuclear cells (PBMCs), the method comprising contacting a composition comprising one or more PBMCs isolated from a donor subject with an effective amount of a MYC fusion polypeptide, comprising (i) a protein transduction domain (PTD); (ii) a MYC polypeptide sequence, and cooling the PBMCs to a temperature sufficient to freeze the composition.

In some embodiments, the protein transduction domain sequence is a TAT protein transduction domain sequence. In some embodiments, the MYC polypeptide sequence comprises the amino acid sequence set forth in SEQ ID NO: 2 or 11. In some embodiments, the PTD-MYC fusion polypeptide comprises the amino acid sequence set forth in SEQ ID NO: 1.

In some embodiments, the one or more immune cells isolated from a donor subject can include B cells, T cells, natural killer (NK) cells, myeloid cells, or any combination thereof. In some embodiments, the one or more myeloid cells isolated from a donor subject can include monocytes, macrophages, dendritic cells, eosinophils, neutrophils, mast cells, basophils, granulocytes, or any combination thereof.

In some embodiments, the one or more B cells isolated from a donor subject can include a pre-B cell, a progenitor B cell, an early pro-B cell, a late pro-B cell, a large pre-B cell, a small pre-B cell, an immature B cell, a mature B cell, a naïve B cell, a plasma B cell, an activated B cell, an anergic B cell, a tolerant B cell, a chimeric B cell, an antigen-specific B cell, a memory B cell, a B-1 cell, a B-2 cell, an anergic AN1/T3 cell population, or a combination of two or more thereof.

In some embodiments, the one or more T cells isolated from a donor subject can include naïve T cells, CD4+ T cells, CD8+ T cells, memory T cells, activated T cells, anergic T cells, tolerant T cells, chimeric T cells, and antigen-specific T cells, regulatory T cells, or any combination thereof.

In some embodiments, the one or more peripheral blood mononuclear cells can be a T-cell, a B-cell, an NK cell, a monocyte, a granulocyte, or any combination thereof.

In some embodiments, the method further comprises suspending the one or more immune cells, including one or more PBMCs, in a cell suspension medium. In some embodiments, the cell suspension medium is suitable for cryopreservation of mammalian cells. In some embodiments, the cell suspension medium is suitable for cryopreservation of immune cells, including PBMCs. In some embodiments, the cell suspension medium comprises CHB media, CS5 media, or CS10 media.

In some embodiments, the immune cells are cooled using a controlled-rate cryogenic freezer. In some embodiments, the immune cells are cooled at a rate of about −1° C. per min. In some embodiments, the PBMCs are cooled using a controlled-rate cryogenic freezer. In some embodiments, the PBMCs are cooled at a rate of about −1° C. per min.

In some embodiments, the temperature sufficient to freeze the composition is about −80° C. to about −190° C. In some embodiments, the temperature sufficient to freeze the composition is about −80° C., about −82° C., about −84° C., about −86° C., about −88° C., about −90° C., about −92° C., about −94° C., about −96° C., about −98° C., about −100° C., about −105° C., about −110° C., about −115° C., about −120° C., about −125° C., about −130° C., about −135° C., about −140° C., about −145° C., about −150° C., about −155° C., about −160° C., about −165° C., about −170° C., about −175° C., about −180° C., about −185° C., about −190° C., or any integer value in between.

In some embodiments, the method further comprises thawing of the cryopreserved cells, such that the cells exhibit one or more of increased cell viability, increased cell recovery, or increased expression of CD25 after cell activation as compared to control cells not contacted with an effective amount of the MYC fusion polypeptide.

In another aspect, the present disclosure provides for a frozen composition comprising a MYC fusion polypeptide, comprising (i) a protein transduction domain; (ii) a MYC polypeptide sequence, and one or more immune cells isolated from a donor subject, wherein the composition exhibits increased cell viability compared to control immune cells isolated from the subject.

In another related aspect, the present disclosure provides for a frozen composition comprising a MYC fusion polypeptide, comprising (i) a protein transduction domain; (ii) a MYC polypeptide sequence, and one or more peripheral blood mononuclear cells (PBMCs) isolated from a donor subject, wherein the composition exhibits increased cell viability compared to control PBMCs isolated from the subject. In some embodiments, the protein transduction domain sequence is a TAT protein transduction domain sequence. In some embodiments, the MYC polypeptide sequence comprises the amino acid sequence set forth in SEQ ID NO: 2 or 11. In some embodiments, the PTD-MYC fusion polypeptide comprises the amino acid sequence set forth in SEQ ID NO: 1.

In some embodiments, the one or more immune cells isolated from a donor subject can include B cells, T cells, natural killer (NK) cells, myeloid cells, or any combination thereof. In some embodiments, the one or more myeloid cells isolated from a donor subject can include monocytes, macrophages, dendritic cells, eosinophils, neutrophils, mast cells, basophils, granulocytes, or any combination thereof.

In some embodiments, the one or more B cells isolated from a donor subject can include a pre-B cell, a progenitor B cell, an early pro-B cell, a late pro-B cell, a large pre-B cell, a small pre-B cell, an immature B cell, a mature B cell, a naïve B cell, a plasma B cell, an activated B cell, an anergic B cell, a tolerant B cell, a chimeric B cell, an antigen-specific B cell, a memory B cell, a B-1 cell, a B-2 cell, an anergic AN1/T3 cell population, or a combination of two or more thereof.

In some embodiments, the one or more T cells isolated from a donor subject can include naïve T cells, CD4+ T cells, CD8+ T cells, memory T cells, activated T cells, anergic T cells, tolerant T cells, chimeric T cells, and antigen-specific T cells, regulatory T cells, or any combination thereof.

In some embodiments, the one or more peripheral blood mononuclear cells can be a T-cell, a B-cell, an NK cell, a monocyte, a granulocyte, or any combination thereof.

In some embodiments, the composition further comprises a cell suspension medium. In some embodiments, the cell suspension medium comprises CHB media, CS5 media, or CS10 media.

In some embodiments, the composition exhibits increased cell recovery when thawed as compared to control PBMCs after a freeze-thaw cycle.

In some embodiments, the composition exhibits increased expression of CD25 after cell activation as compared to control PBMCs after a freeze thaw cycle.

In some embodiments, the compositions of the present technology can advantageously increase the utilization of immune cells and/or PBMCs in adoptive cell transfer (ACT). Adoptive cell transfer (ACT) is a form of immunotherapy that involves the transfer of immune cells with antitumor activity into patients. ACT typically involves isolation of lymphocytes with antitumor activity from a donor subject, culturing the lymphocytes in vitro to expand the population, and then infusing the lymphocytes into a patient in need thereof. In some embodiments, the immune cells and/or PBMCs are primary cells isolated from a donor.

In some embodiments, the immune cells and/or PBMCs are modified following isolation. For example, in some embodiments, the cells are immune cells (e.g., T cells) modified to expression one or more heterologous receptors or modified receptors (e.g., a chimeric antigen receptor). In some embodiments, the cells are engineered chimeric antigen receptor (CAR) T-cells. In some embodiments, the cells are engineered chimeric antigen receptor (CAR) Treg-cells.

In some embodiments, the immune cells and modified immune cells that have been cryopreserved according to the methods provided herein can be used to increase an immune response in a subject. Exemplary uses of these cells include but are not limited to cancer immunotherapy and treatment of pathogenic infections, such as viral, bacterial, or fungal infections.

In some embodiments, the immune cells and modified immune cells that have been cryopreserved according to the methods provided herein can be used to decrease an immune response in a subject. Exemplary uses of these cells (e.g., Tregs and modified Treg cells) include but are not limited to treatment of autoimmune and allergic diseases and conditions, such as multiple sclerosis (MS), lupus erythematosus, asthma, autoimmune uveitis, Crohn's disease, colitis, Graft vs. host disease (GvHD), rheumatoid arthritis, inflammatory bowel disease, diabetes, and organ or tissue transplant rejection.

In some embodiments, the compositions of the present technology can be used for in vitro or in vivo immunological studies.

In some embodiments, the compositions of the present technology can be used in methods for creating an immune cell bank for use in immunotherapy and adoptive cell transfer.

III. Methods of Obtaining and Preparing Immune Cells and/or PBMCs Prior to Cryopreservation Immune cells and/or peripheral blood mononuclear cells for use in the methods provided herein can be obtained using any suitable method known in the art. In some embodiments, the immune cells are primary immune cells. In some embodiments, the immune cells are lymphocytes, such as T and B cells. In some embodiments, the immune cells are natural killer (NK) cells. In some embodiments, the immune cells are a mixture of lymphocytes and NK cells. In some embodiments, the immune cells are peripheral blood mononuclear cells (PBMCs). In some embodiments, the T cells are removed during surgery of a tumor or a metastatic tumor in a subject. For example, in some embodiments, the T cells are isolated after removal of tumor tissue by biopsy. In some embodiments, the peripheral blood mononuclear cells (PBMCs) can be a T-cell, a B-cell, an NK cell, a monocyte, a granulocyte, or any combination thereof.

In some embodiments, the immune cells can be isolated from a sample containing a population of cells, such as a blood, lymph or tissue biopsy sample. Immune cells can be isolated from a population of cells by any means known in the art.

In some embodiments, the immune cells can be isolated from a whole blood sample, such as a peripheral blood sample. In some embodiments, immune cells can be isolated from a leukapheresis unit. In some embodiments, peripheral blood mononuclear cells can be isolated from a leukapheresis unit. In some embodiments, the peripheral blood mononuclear cell fraction can be isolated from a whole blood sample via gradient separation with any suitable density gradient media. In some embodiments, for example, the density gradient media used to isolate the peripheral blood mononuclear cell fraction is Ficoll-Paque® PLUS or Ficoll-Paque® PREMIUM. In one embodiment, the PBMC fraction is isolated from a whole blood sample via gradient separation with Ficoll-Paque® PLUS media. In some embodiments, the blood anticoagulant, ethylenediaminetetraacetic acid (EDTA), is employed to prevent coagulation of the blood sample. Accordingly, in some embodiments the methods employ collection vials coated with the EDTA. EDTA acts as a blood anticoagulant via chelation of Ca' ions in the blood sample responsible for coagulation and clotting. In some embodiments, the red blood cells of the sample are depleted from the sample.

In one embodiment, the method comprises obtaining a bulk population of immune cells from a tumor sample by any suitable method known in the art. For example, a bulk population of immune cells can be obtained from a tumor sample by dissociating the tumor sample into a cell suspension from which specific cell populations can be selected. Suitable methods of obtaining a bulk population of immune cells can include, but are not limited to, any one or more of mechanically dissociating (e.g., mincing) the tumor, enzymatically dissociating (e.g., digesting) the tumor, and aspiration (e.g., as with a needle).

The population of immune cells obtained from a sample can comprise any suitable type of immune cell including, but not limited to, B cells, T cells, natural killer (NK) cells, myeloid cells, or any combination thereof. In some embodiments, the bulk population of myeloid cells obtained from a sample can include monocytes, macrophages, dendritic cells, eosinophils, neutrophils, mast cells, basophils, granulocytes, or any combination thereof.

The population of T cells obtained from a sample can comprise any suitable type of T cell. In some embodiments, the T cells obtained from a sample can comprise naïve T cells, CD4+ T cells, CD8+ T cells, memory T cells, activated T cells, anergic T cells, tolerant T cells, chimeric T cells, and antigen-specific T cells, or any combination thereof.

The population of B cells obtained from a sample can comprise any suitable type of B cell. In some embodiments, the B cells obtained from a sample can comprise pre-B cells, progenitor B cells, early pro-B cells, late pro-B cells, large pre-B cells, small pre-B cells, immature B cells, mature B cells, naïve B cells, plasma B cells, activated B cells, anergic B cells, tolerant B cells, chimeric B cells, antigen-specific B cells, memory B cells, B-1 cells, B-2 cells, anergic AN1/T3 cell populations, or a combination of two or more thereof.

The population of immune cells obtained from a sample can comprise peripheral blood mononuclear cells (PBMCs). In some embodiments, the PBMCs obtained from a sample can comprise a T-cell, a B-cell, an NK cell, a monocyte, a granulocyte, or any combination thereof.

The sample can be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals can be non-human primates, e.g., of the order Primates, Ceboids, or Simoids (monkeys) or of the order Anthropoids (humans and apes). In some embodiments, the mammal can be a mammal of the order Rodentia, such as mice and hamsters. Preferably, the mammal is a non-human primate or a human. An exemplary mammal is a human.

In some embodiments, immune cells can be further isolated by positive or negative selection techniques. Enrichment of an immune cell population by negative selection can be accomplished with a combination of antibodies directed to surface markers unique to the negatively selected cells. Cells can be enriched by cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) can be depleted from blood preparations by a variety of methodologies, including, but not limited to anti-CD14 coated beads or columns, or utilization of the phagocytotic activity of these cells to facilitate removal.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/mL can be used. In one embodiment, a concentration of 1 billion cells/mL is used. In a further embodiment, greater than 100 million cells/mL can be used. In a further embodiment, a concentration of cells of about 10 million cells/mL, about 15 million cells/mL, about 20 million cells/mL, about 25 million cells/mL, about 30 million cells/mL, about 35 million cells/mL, about 40 million cells/mL, about 45 million cells/mL, or about 50 million cells/mL can be used. In yet another embodiment, a concentration of cells from about 75 million cells/mL, about 80 million cells/mL, about 85 million cells/mL, about 90 million cells/mL, about 95 million cells/mL, or about 100 million cells/mL can be used. In further embodiments, concentrations of about 125 million cells/mL or about 150 million cells/mL can be used. Using high concentrations can result in increased cell yield, cell activation, and cell expansion. Further, use of high cell concentrations allows more efficient capture of cells that can weakly express target antigens of interest, such as CD28-negative T cells, or from samples where there are many tumor cells present (i.e., leukemic blood, tumor tissue, etc.). Such populations of cells can have therapeutic value and therefore would be desirable to obtain. For example, using high concentration of cells allows more efficient selection of CD8+ T cells that normally have weaker CD28 expression.

In another related embodiment, it can be desirable to use lower concentrations of cells. By significantly diluting the mixture of the immune cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used can be $5 \times 10^6$/mL. In some embodiments, the concentration used can be from about $1 \times 10^5$/mL to $1 \times 10^6$/mL, or any integer value in between. Thus, the concentration used can be from about $1 \times 10^5$/mL, about $1.1 \times 10^5$/mL, about $1.2 \times 10^5$/mL, about $1.3 \times 10^5$/mL, about $1.4 \times 10^5$/mL, about $1.5 \times 10^5$/mL, about $1.6 \times 10^5$/mL, about $1.7 \times 10^5$/mL, about $1.8 \times 10^5$/mL, about $1.9 \times 10^5$/mL, about $2 \times 10^5$/mL, about $2.2 \times 10^5$/mL, about $2.4 \times 10^5$/mL, about $2.6 \times 10^5$/mL, about $2.8 \times 10^5$/mL, about $3 \times 10^5$/mL, about $3.2 \times 10^5$/mL, about $3.4 \times 10^5$/mL, about $3.6 \times 10^5$/mL, about $3.8 \times 10^5$/mL, about $4 \times 10^5$/mL, about $4.2 \times 10^5$/mL, about $4.4 \times 10^5$/mL, about $4.6 \times 10^5$/mL, about $4.8 \times 10^5$/mL, about $5 \times 10^5$/mL, about $5.5 \times 10^5$/mL, about $6 \times 10^5$/mL, about $6.5 \times 10^5$/mL, about $7 \times 10^5$/mL, about $7.5 \times 10^5$/mL, about $8 \times 10^5$/mL, about $8.5 \times 10^5$/mL, about $9 \times 10^5$/mL, about $9.5 \times 10^5$/mL, about $1 \times 10^6$/mL, or any integer value in between.

In some embodiments, cells are directly labeled with an epitope-specific reagent for isolation by flow cytometry followed by characterization of cell phenotypes. In some embodiments, immune cells are isolated by contacting the immune cell specific antibodies. In some embodiments, PBMCs are isolated by contacting the PBMC specific antibodies. Sorting of antigen-specific T cells, or generally any cells of the present technology, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

IV. MYC Fusion Proteins

In some embodiments, the PTD-MYC fusion polypeptide comprises a protein transduction domain (PTD), a MYC polypeptide that promotes one or more of cell survival or proliferation, and optionally a protein tag domain, e.g., one or more amino acid sequences that facilitate purification of the fusion protein. In some embodiments, a cell contacted with MYC polypeptide exhibits increased survival time (e.g., as compared to an identical or similar cell of the same type that was not contacted with MYC), and/or increased proliferation (e.g., as compared to an identical or similar cell of the same type that was not contacted with MYC).

In some embodiments, the fusion polypeptide comprises (a) a protein transduction domain; and (b) a MYC polypeptide sequence. In some embodiments, the fusion polypeptide is a polypeptide of Formula (I):

protein transduction domain-MYC polypeptide sequence.

In some embodiments, a fusion polypeptide disclosed herein comprises (a) a protein transduction domain; (b) a MYC polypeptide sequence; and (c) one or more molecules that link the protein transduction domain and the MYC polypeptide sequence. In some embodiments, the fusion polypeptide is a polypeptide of Formula (II):

protein transduction domain-$X$-MYC polypeptide sequence, wherein —$X$— is a molecule that links the protein transduction domain and the MYC polypeptide sequence. In some embodiments, —$X$— is at least one amino acid.

In some embodiments, a fusion polypeptide disclosed herein comprises (a) a protein transduction domain; (b) a MYC polypeptide sequence; (c) at least two protein tags; and (d) optionally linker(s). In some embodiments, the fusion polypeptide is a polypeptide of Formula (III-VI):

protein transduction domain-$X$-MYC polypeptide sequence-$X$-protein tag 1-$X$-protein tag 2  (Formula (III)), or protein transduction domain-MYC polypeptide sequence-$X$-protein tag 1-$X$-protein tag 2  (Formula (IV)), or protein transduction domain-MYC polypeptide sequence-protein tag 1-$X$-protein tag 2  (Formula (V)), or protein transduction domain-MYC polypeptide sequence-protein tag 1-protein tag 2  (Formula (VI)), wherein —$X$— is a linker. In some embodiments, —$X$— is one or more amino acids.

In some embodiments, a fusion polypeptide disclosed herein comprises (a) a protein transduction domain; (b) a MYC polypeptide sequence; (c) a 6-histidine tag; (d) a V5 epitope tag: and (e) optionally linker(s). In some embodiments, the fusion polypeptide is a polypeptide of Formula (VII-XIV):

protein transduction domain-$X$-MYC polypeptide sequence-$X$-6-histidine tag-$X$-V5 epitope tag(Formula (VII)), or protein transduction domain-MYC polypeptide sequence-$X$-6-histidine tag-$X$-V5 epitope tag(Formula (VIII)), or protein transduction domain-MYC polypeptide sequence-6-histidine tag-$X$-V5 epitope tag  (Formula (IX)), or protein transduction domain-MYC polypeptide sequence-6-histidine tag-V5 epitope tag  (Formula (X)), protein transduction domain-$X$-MYC polypeptide sequence-$X$-V5 epitope tag-$X$-6-histidine tag (Formula (XI)), or protein transduction domain-MYC polypeptide sequence-$X$-V5 epitope tag-$X$-6-histidine tag(Formula (XII)), or protein transduction domain-MYC polypeptide sequence-V5 epitope tag-$X$-6-histidine tag  (Formula (XIII)), or protein transduction domain-MYC polypeptide sequence-V5 epitope tag-6-histidine tag  (Formula (XIV)), wherein —$X$— is a linker. In some embodiments, —$X$— is one or more amino acids.

As noted above, in some embodiments, the MYC fusion protein comprises one or more linker sequences. The linker sequences can be employed to link the protein transduction domain, MYC polypeptide sequence, V5 epitope tag and/or 6-histidine tag of the fusion protein. In some embodiments, the linker comprises one or more amino acids. In some embodiments, the amino acid sequence of the linker comprises KGELNSKLE. In some embodiments, the linker comprises the amino acid sequence of RTG.

Protein Transduction Domain (PTD)

In some embodiments, the MYC fusion protein includes a protein transduction domain. Peptide transport provides an alternative for delivery of small molecules, proteins, or nucleic acids across the cell membrane to an intracellular compartment of a cell. One non-limiting example and well-characterized protein transduction domain (PTD) is a TAT-derived peptide. Frankel et al. (see, e.g., U.S. Pat. Nos. 5,804,604, 5,747,641, 5,674,980, 5,670,617, and 5,652,122) demonstrated transport of a cargo protein (β-galactosidase or horseradish peroxidase) into a cell by conjugating a peptide containing amino acids 48-57 of TAT to the cargo protein. In some embodiments, TAT comprises an amino acid sequence of MRKKRRQRRR (SEQ ID NO: 7).

Another non-limiting example of a PTD is penetratin. Penetratin can transport hydrophilic macromolecules across the cell membrane (Derossi et al, *Trends Cell Biol.*, 8:84-87 (1998) incorporated herein by reference in its entirety). Penetratin is a 16 amino acid peptide that corresponds to amino acids 43-58 of the homeodomain of Antennapedia, a *Drosophila* transcription factor which is internalized by cells in culture.

Yet another non-limiting example of a PTD is VP22. VP22, a tegument protein from Herpes simplex virus type 1 (HSV-1), has the ability to transport proteins and nucleic acids across a cell membrane (Elliot et al., *Cell* 88:223-233, 1997, incorporated herein by reference in its entirety). Residues 267-300 of VP22 are necessary but cannot be sufficient for transport. Because the region responsible for transport function has not been identified, the entire VP22 protein is commonly used to transport cargo proteins and nucleic acids across the cell membrane (Schwarze et al., *Trends Pharmacol Sci,* 21:45-48, 2000).

In some embodiments, the PTD-MYC fusion polypeptide includes a protein transduction domain. By way of example, but not by way of limitation, in some embodiments, the protein transduction domain comprises the protein transduction domain of one or more of TAT, penetratin, VP22, vpr, EPTD, R9, R15, VP16, and Antennapedia. In some embodiments, the protein transduction domain comprises the protein transduction domain of one or more of TAT, penetratin, VP22, vpr, and EPTD. In some embodiments, the protein transduction domain comprises the protein transduction domain of at least one of TAT, penetratin, VP22, vpr, EPTD, R9, R15, VP16, and Antennapedia. In some embodiments, the protein transduction domain comprises a synthetic protein transduction domain (e.g., polyarginine or PTD-5). In particular embodiments, the protein transduction domain comprises a TAT protein transduction domain. In some embodiments, the protein transduction domain is covalently linked to the MYC polypeptide. In some embodiments, the protein transduction domain is linked to the MYC polypeptide via a peptide bond. In some embodiments, the protein transduction domain is linked to the MYC polypeptide via a linker sequence. In some embodiments, the linker comprises a short amino acid sequence. By way of example, but not by way of limitation, in some embodiments, the linker sequence is 1, 2, 3, 4, 5, 6, 7, 8, 9, or 10 amino acids in length.

The MYC fusion protein of the present technology can be arranged in any desired order. For example, in some embodiments, the MYC fusion protein can be arranged in order of a) the protein transduction domain linked in frame to the MYC polypeptide, b) the MYC polypeptide linked in frame to the V5 domain, and c) the V5 domain linked in frame to the 6-histidine epitope tag. In some embodiments, the MYC fusion protein has an order of components of a) the MYC polypeptide linked in frame to the protein transduction domain, b) the protein transduction domain linked in frame to the V5 domain, and c) the V5 domain linked in frame to the 6-histidine epitope tag. In some embodiments, one or more additional amino acid sequences or linkers can be included between each of the sequences. In some embodiments, additional amino acids can be included at the start and/or end of the polypeptide sequences.

In some embodiments, the protein transduction domain is a TAT protein transduction domain. In some embodiments, the protein transduction domain is $TAT_{[48-57]}$. In some embodiments, the protein transduction domain is $TAT_{[57-48]}$.

Protein Tag Domains

In some embodiments, the MYC fusion protein comprises a protein tag domain that comprises one or more amino acid sequences that facilitate purification of the fusion protein. In some embodiments, the protein tag domain comprises one or more of a polyhistidine tag, and an epitope tag. By way of example, but not by way of limitation, exemplary tags include one or more of a V5, a histidine-tag (e.g., a 6-histidine tag), HA (hemagglutinin) tags, FLAG tag, CBP (calmodulin binding peptide), CYD (covalent yet dissociable NorpD peptide), StrepII, or HPC (heavy chain of protein C). In some embodiments, the protein tag domain comprises about 10 to about 20 amino acids in length. In some embodiments, the protein tag domain comprises 2 amino acids to 40 amino acids in length, for example 6-20 amino acids in length. In some embodiments, the protein tag domain comprises 2 amino acids, 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids, 30 amino acids, 31 amino acids, 32 amino acids, 33 amino acids, 34 amino acids, 35 amino acids, 36 amino acids, 37 amino acids, 38 amino acids, 39 amino acids, or 40 amino acids. In some embodiments, two of the above listed tags (for example, V5 and the HIS-tag) are used together to form the protein tag domain.

In some embodiments, the histidine tag is a 6-histidine tag. In some embodiments, the histidine tag comprises the sequence HHHHHH (SEQ ID NO:8). In some embodiments, the fusion polypeptide disclosed herein comprises a V5 epitope tag. In some embodiments, the V5 tag comprises the amino acid sequence of: GKPIPNPLLGLDST (SEQ ID NO:9). In some embodiments, the V5 tag comprises the amino acid sequence of IPNPLLGLD (SEQ ID NO:10).

The protein tags can be added to the fusion protein disclosed herein by any suitable method. By way of example, but not by way of limitation, in some embodiments, a TAT-MYC polypeptide sequence is cloned into an expression vector encoding one or more protein tags, e.g., a polyHis-tag and/or a V5 tag. In some embodiments, a polyhistidine tag and/or a V5 tag is added by PCR (i.e., the PCR primers comprise a polyhistidine sequence and/or V5 sequence).

Construction of PTD-MYC Fusion Polypeptides

PTD-MYC fusion polypeptides (e.g., TAT-MYC fusion polypeptide) disclosed herein can be constructed by methods well known in the art. By way of example, but not by way of limitation, a nucleotide sequence encoding a TAT-MYC fusion polypeptide can be generated by PCR. In some embodiments, a forward primer for a human MYC sequence comprises an in frame N-terminal 9-amino-acid sequence of the TAT protein transduction domain (e.g., RKKRRQRRR). In some embodiments, a reverse primer for a human MYC sequence is designed to remove the stop codon. In some embodiments, the PCR product is cloned into any suitable expression vector. In some embodiments, the expression vector comprises a polyhistidine tag and a V5 tag.

In some embodiments, a fusion polypeptide disclosed herein comprises (a) TAT, and (b) c-MYC. In some embodiments, a fusion polypeptide disclosed herein comprises (a) TAT[48-57], and (b) c-MYC. In some embodiments, a fusion polypeptide disclosed herein comprises (a) $TAT_{[57-48]}$, and (b) c-MYC.

In some embodiments, a fusion polypeptide disclosed herein comprises (a) TAT, (b) c-MYC, (c) linker(s), (d) V5 tag, and (e) 6-histidine tag. In some embodiments, a fusion polypeptide disclosed herein comprises (a) $TAT_{[48-57]}$, (b) c-MYC, (c) linker(s), (d) V5 tag, and (e) 6-histidine tag. In some embodiments, a fusion polypeptide disclosed herein comprises (a) $TAT_{[57-48]}$, (b) c-MYC, (c) linker(s), (d) V5 tag, and (e) 6-histidine tag.

In some embodiments, the PTD-MYC fusion polypeptide comprises SEQ ID NO: 1; in some embodiments, the PTD-MYC fusion polypeptide is SEQ ID NO: 1.

```
                                              (SEQ ID NO: 1)
MRKKRRQRRRPLNVSFTNRNYDLDYDSVQPYFYCDEEENFYQQQQQSEL

QPPAPSEDIWKKFELLPTPPLSPSRRSGLCSPSYVAVTPFSLRGDNDGG

GGSFSTADQLEMVTELLGGDMVNQSFICDPDDETFIKNIIQDCMWSGF

SAAAKLVSEKLASYQAARKDSGSPNPARGHSVCSTSSLYLQDLSAAASE

CIDPSVVFPYPLNDSSSPKSCASQDSSAFSPSSDSLLSSTESSPQGSPE

PLVLREETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLR
```

-continued

```
QISNNRKCTSPRSSDTEENVKRRTHNVLERQRRNELKRSFFALRDQIPE

LENNEKAPKVVILKKATAYILSVQAEEQKLISEEDLLRKRREQLKHKLE

QLRKGELNSKLEGKPIPNPLLGLDSTRTGEITEHTEHH.
```

The fusion protein can be modified during or after synthesis to include one or more functional groups. By way of example but not by way of limitation, the protein can be modified to include one or more of an acetyl, phosphate, acetate, amide, alkyl, and/or methyl group. This list is not intended to be exhaustive, and is exemplary only. In some embodiments, the protein includes at least one acetyl group.

A PTD-MYC fusion polypeptide can be generated by any suitable method known the art, e.g. by recombinant protein expression in a cell, such as a bacterial cell, an insect cell, or mammalian cell. In some embodiments, a PTD-MYC fusion polypeptide is recombinantly produced by microbial fermentation. In some embodiments microbial fermentation is performed in a fermentation volume of from about 1 to about 10,000 liters, for example, a fermentation volume of about 10 to about 1000 liters. The fermentation can utilize any suitable microbial host cell and culture medium. In exemplary embodiments, *E. coli* is utilized as the microbial host cell. In alternative embodiments, other microorganisms can be used, e.g., *S. cerevisiae, P. pastoris, Lactobacilli, Bacilli* and *Aspergilli*. In an exemplary embodiment the microbial host cell is BL-21 Star™ *E. coli* strain (Invitrogen). In an exemplary embodiment the microbial host cell is BLR DE3 *E. coli.* strain.

In some embodiments the host cells are modified to provide tRNAs for rare codons, which are employed to overcome host microbial cell codon bias to improve translation of the expressed proteins. In exemplary embodiments, the host cells (e.g., *E. coli*) transformed with a plasmid, such as pRARE (CamR), which express tRNAs for AGG, AGA, AUA, CUA, CCC, GGA codons. Additional, suitable plasmids or constructs for providing tRNAs for particular codons are known in the art and can be employed in the methods provided.

Integrative or self-replicative vectors can be used for the purpose of introducing the PTD-MYC fusion polypeptide expression cassette into a host cell of choice. In an expression cassette, the coding sequence for the PTD-MYC fusion polypeptide is operably linked to promoter, such as an inducible promoter. Inducible promoters are promoters that initiate increased levels of transcription from DNA under their control in response to some change in culture conditions, e.g., the presence or absence of a nutrient or a change in temperature. In some embodiments, the nucleic acid encoding the PTD-MYC fusion polypeptide is codon optimized for bacterial expression.

Exemplary promoters that are recognized by a variety of potential host cells are well known. These promoters can be operably linked to PTD-MYC fusion polypeptide-encoding DNA by removing the promoter from the source DNA, if present, by restriction enzyme digestion and inserting the isolated promoter sequence into the vector. Promoters suitable for use with microbial hosts include, but are not limited to, the β-lactamase and lactose promoter systems (Chang et al. (1978) *Nature*, 275:617-624; Goeddel et al. (1979) *Nature,* 281: 544), alkaline phosphatase, a tryptophan (trp) promoter system (Goeddel (1980) *Nucleic Acids Res.* 8: 4057; EP 36,776), and hybrid promoters such as the tac promoter (deBoer et al. (1983) *Proc. Natl. Acad. Sci. USA* 80: 21-25). Any promoter for suitable for expression by the selected host cell can be used. Nucleotide sequences for suitable are published, thereby enabling a skilled worker operably to ligate them to DNA encoding PTD-MYC fusion polypeptide (see, e.g., Siebenlist et al. (1980) *Cell* 20: 269) using linkers or adaptors to supply any required restriction sites. In exemplary embodiments, promoters for use in bacterial systems can contain a Shine-Dalgarno (S.D.) sequence operably linked to the coding sequence. In some embodiments, the inducible promoter is the lacZ promoter, which is induced with Isopropyl β-D-1-thiogalactopyranoside (IPTG), as is well-known in the art. Promoters and expression cassettes can also be synthesized de novo using well known techniques for synthesizing DNA sequences of interest. In an exemplary embodiment, the expression vector for expression of the PTD-MYC fusion polypeptides herein is pET101/D-Topo (Invitrogen).

For expression of the PTD-MYC fusion polypeptides, the microbial host containing the expression vector encoding the PTD-MYC fusion polypeptide is typically grown to high density in a fermentation reactor. In some embodiments, the reactor has controlled feeds for glucose. In some embodiments, a fermenter inoculum is first cultured in medium supplemented with antibiotics (e.g., overnight culture). The fermenter inoculum is then used to inoculate the fermenter culture for expression of the protein. At an OD600 of at least about 15, usually at least about 20, at least 25, at least about 30 or higher, of the fermenter culture, expression of the recombinant protein is induced. In exemplary embodiments, where the inducible promoter is the lacZ promoter, IPTG is added to the fermentation medium to induce expression of the PTD-MYC fusion polypeptide. Generally, the IPTG is added to the fermenter culture at an OD600 which represents logarithmic growth phase.

In certain embodiments of the methods provided, induced protein expression is maintained for around about 2 to around about 5 hours post induction, and can be from around about 2 to around about 3 hours post-induction. Longer periods of induction can be undesirable due to degradation of the recombinant protein. The temperature of the reaction mixture during induction is preferably from about 28° C. to about 37° C., usually from about 30° C. to about 37° C. In particular embodiments, induction is at about 37° C.

The PTD-MYC fusion polypeptide is typically expressed as cytosolic inclusion bodies in microbial cells. To harvest inclusion bodies, a cell pellet is collected by centrifugation of the fermentation culture following induction, frozen at −70° C. or below, thawed and resuspended in disruption buffer. The cells are lysed by conventional methods, e.g., sonication, homogenization, etc. The lysate is then resuspended in solubilization buffer, usually in the presence of urea at a concentration effective to solubilize proteins, e.g., from around about 5M, 6M, 7M, 8M, 9M or greater. Resuspension can require mechanically breaking apart the pellet and stirring to achieve homogeneity. In some embodiments, the cell pellet is directly resuspended in urea buffer and mixed until homogenous. In some embodiments, the resuspension/solubilization buffer is 8M Urea, 50 mM Phosphate pH 7.5 and the suspension is passed through a homogenizer.

In some embodiments, the homogenized suspension is sulfonylated. For example, in some embodiments, the homogenized suspension is adjusted to include 200 mM Sodium Sulfite and 10 mM Sodium Tetrathionate. The solution is then mixed at room temperature until homogeneous. The mixed lysate is then mixed for an additional period of time to complete the sulfonylation (e.g., at 2-8° C. for ≥12 hours). The sulfonylated lysate was then centrifuged for an hour. The supernatant containing the sulfonylated PTD-MYC fusion polypeptides is then collected by centrifugation and the cell pellet discarded. The supernatant is then passed through a filter, e.g., 0.22 μm membrane filter to clarify the lysate.

The solubilized protein is then purified. Purification methods can include affinity chromatography, reverse phase chromatography, gel exclusion chromatography, and the like. In some embodiments, affinity chromatography is used. For example, the protein is provided with an epitope tag or histidine 6 tag for convenient purification. In the present methods, exemplary PTD-MYC fusion polypeptide comprise histidine 6 tag for purification using Ni affinity chromatography using Ni-resin.

In exemplary embodiments, the Ni-resin column is equilibrated in a buffer containing urea. In some embodiments, the equilibration buffer is 6M Urea, 50 mM Phosphate, 500 mM NaCl, and 10% Glycerol solution. The sulfonylated and clarified supernatant comprising the PTD-MYC fusion polypeptide is then loaded onto the Ni-resin column. The column is then washed with a wash buffer, e.g., 6M Urea, 50 mM Phosphate, 10% Glycerol, 500 mM NaCl, pH 7.5. The column was then washed with sequential wash buffers with decreasing salt concentration. For example, exemplary subsequent washed can include 6M Urea, 50 mM Phosphate, 10% Glycerol, and 2M NaCl, pH 7.5, followed another wash of 6M Urea, 50 mM Phosphate, 10% Glycerol, 50 mM NaCl, and 30 mM Imidazole, pH 7.5.

Following sequential application of the wash buffers the PTD-MYC fusion polypeptide is eluted from the column by addition of elution buffer, e.g., 6M Urea, 50 mM Phosphate, 10% Glycerol, and 50 mM NaCl, pH 7.5 with a gradient from 100 to 300 mM Imidazole, and collecting fractions. The protein containing fractions to be pooled are then filtered through a 0.22 μm membrane. Assessment of protein yield can be measured using any suitable method, e.g., spectrophotometry at UV wavelength 280.

In some embodiments, one or more additional purification methods can be employed to further purify the isolated PTD-MYC fusion polypeptides. In exemplary embodiments, the pooled fractions from the Ni-Sepharose chromatography step are further purified by anion exchange chromatography using a Q-Sepharose resin. In some embodiments, the pool is prepared for loading onto the Q-Sepharose column by diluting the samples to the conductivity of the Q Sepharose buffer (17.52+/−1 mS/cm) with the second wash buffer (e.g., 6M Urea, 50 mM Phosphate, 10% Glycerol, 2M NaCl, pH 7.5) from the Ni Sepharose chromatography step. The diluted pool is then loaded onto the Q-Sepharose column, followed by two chase steps using a chase buffer (e.g., 6M Urea, 50 mM Phosphate, 300 mM NaCl, and 10% Glycerol), with further sequential applications of the chase buffer until the UV trace reaches baseline, indicating that the protein has eluted from the column.

V. Methods of Cryopreservation

As provided previously, the present disclosure is directed to methods for the cryopreservation of immune cells, where the method comprises (a) contacting a composition comprising one or more immune cells isolated from a donor subject with an effective amount of a MYC fusion polypeptide, comprising (i) a protein transduction domain; (ii) a MYC polypeptide sequence, and cooling the immune cells to a temperature sufficient to freeze the composition. Exemplary MYC fusion polypeptides are provided herein. In some embodiments, the protein transduction domain sequence is a TAT protein transduction domain sequence. In some embodiments, the MYC fusion polypeptide comprises SEQ ID NO: 1.

In some embodiments, the immune cells are peripheral blood mononuclear cells (PBMCs). Accordingly, the present disclosure is also directed to methods for the cryopreservation of PBMCs, where the method comprises (a) contacting a composition comprising one or more PBMCs isolated from a donor subject with an effective amount of a MYC fusion polypeptide, comprising (i) a protein transduction domain; (ii) a MYC polypeptide sequence, and cooling the PBMCs to a temperature sufficient to freeze the composition. In some embodiments, the protein transduction domain sequence is a TAT protein transduction domain sequence. In some embodiments, the MYC fusion polypeptide comprises SEQ ID NO: 1.

In exemplary embodiments of the methods, a whole blood sample of about 30 mL to about 470 mL is isolated from a donor subject. Thus, a whole blood sample of about 30 mL, about 32 mL, about 34 mL, about 36 mL, about 38 mL, about 40 mL, about 42 mL, about 44 mL, about 46 mL, about 48 mL, about 50 mL, about 55 mL, about 60 mL, about 65 mL, about 70 mL, about 75 mL, about 80 mL, about 85 mL, about 90 mL, about 95 mL, about 100 mL, about 110 mL, about 120 mL, about 130 mL, about 140 mL, about 150 mL, about 160 mL, about 170 mL, about 180 mL, about 190 mL, about 200 mL, about 220 mL, about 240 mL, about 260 mL, about 280 mL, about 300 mL, about 320 mL, about 340 mL, about 360 mL, about 380 mL, about 400 mL, about 420 mL, about 440 mL, about 460 mL, about 470 mL, or any integer value in between, can be isolated from a donor subject. In some embodiments, the whole blood sample isolated from a donor subject is then immediately treated with an anticoagulant, such as EDTA (about 1.5% w/v). In some embodiments, the isolated whole blood sample is then allowed to incubate for a period of time (e.g., about 1-24 hours) at about 20° C. to allow the sample to separate the immune cells and/or PBMCs from other components of the whole blood sample (i.e., red blood cells, platelets, plasma, etc.). In some embodiments, separation is carried out using a density-gradient solution (DGS). In some embodiments, a SEPAX-100 cell processing system (Biosafe America Inc., Houston, TX) is employed. The separated cells can be washed one or more times during the cell separation process to remove residual blood components. In some embodiments, the cells are washed using a 2.5% (w/v) HSA (Human Serum Albumin) solution in saline, and then resuspended in the same wash solution to provide a cell suspension.

In some embodiments, samples of the cell suspension can be taken prior to treatment with the PTD-MYC fusion polypeptide (negative controls). In some embodiments, the remaining cells in the suspension can then be treated with the PTD-MYC fusion polypeptide, for example, at a concentration of about 0.5 μg/mL to about 500 μg/mL. In some embodiments, treated and non-treated (negative controls) samples can then be incubated at room temperature for an appropriate time, for example, about 1 hour.

In some embodiments, the immune cells (e.g., PBMCs) are contacted with an effective amount of a PTD-MYC fusion polypeptide for a period of time sufficient to be taken up by the cells prior to freezing. In some embodiments, the immune cells are contacted with an effective amount of a PTD-MYC for less than about 24 hours, less than about 23 hours, less than about 22 hours, less than about 21 hours, less than about 20 hours, less than about 19 hours, less than about 18 hours, less than about 17 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2 hours, less than about 1 hour, less than about 45 minutes, less than about 30 minutes, less than about 15 minutes, or less than about 10 minutes. In some embodiments, the immune cells (e.g., PBMCs) are contacted with an effective amount of a PTD-MYC fusion polypeptide for about 1 hour.

In some embodiments, the immune cells (e.g., PBMCs) are contacted with a PTD-MYC fusion polypeptide at a concentration of about 0.5 µg/mL to about 500 µg/mL. In some embodiments, that can be combined with any of the preceding embodiments, the cells are contacted with a PTD-MYC fusion polypeptide at a concentration of at least 0.5 µg/mL, at least 0.6 µg/mL, at least 0.7 µg/mL, at least 0.8 µg/mL, at least 0.9 µg/mL, at least 1 µg/mL, at least 2 µg/mL, at least 3 µg/mL, at least 4 µg/mL, at least 5 µg/mL, at least 6 µg/mL, at least 7 µg/mL, at least 8 µg/mL, at least 9 µg/mL, at least 10 µg/mL, at least 15 µg/mL, at least 20 µg/mL, at least 25 µg/mL, at least 30 µg/mL, at least 35 µg/mL, at least 40 µg/mL, at least 45 µg/mL, at least 50 µg/mL, at least 55 µg/mL, at least 60 µg/mL, at least 65 µg/mL, at least 70 µg/mL, at least 75 µg/mL, at least 80 µg/mL, at least 85 µg/mL, at least 90 µg/mL, at least 95 µg/mL, at least 100 µg/mL, at least 110 µg/mL, at least 120 µg/mL, at least 130 µg/mL, at least 140 µg/mL, at least 150 µg/mL, at least 160 µg/mL, at least 170 µg/mL, at least 180 µg/mL, at least 190 µg/mL, at least 200 µg/mL, at least 220 µg/mL, at least 240 µg/mL, at least 260 µg/mL, at least 280 µg/mL, at least 300 µg/mL, at least 320 µg/mL, at least 340 µg/mL, at least 360 µg/mL, at least 380 µg/mL, at least 400 µg/mL, at least 420 µg/mL, at least 440 µg/mL, at least 460 µg/mL, at least 480 µg/mL, at least 500 µg/mL, or any integer value in between.

Following incubation with the TAT-MYC polypeptide, the treated immune cells and/or treated PBMCs (TBX-3400) can then be re-washed (e.g., on the SEPAX-100) one or more times, to remove excess PTD-MYC from the cells with a wash solution (e.g., a 2.5% (w/v) HSA solution). Following the final wash step, the treated cells can be resuspended, for example, at a concentration of about $0.5 \times 10^6$ cells/mL to about $1 \times 10^8$ cells/mL. In some embodiments, the treated cells can be resuspended at a concentration of about $0.5 \times 10^6$ cells/mL, about $0.6 \times 10^6$ cells/mL, about $0.7 \times 10^6$ cells/mL, about $0.8 \times 10^6$ cells/mL, about $0.9 \times 10^6$ cells/mL, about $1 \times 10^6$ cells/mL, about $1.1 \times 10^6$ cells/mL, about $1.2 \times 10^6$ cells/mL, about $1.3 \times 10^6$ cells/mL, about $1.4 \times 10^6$ cells/mL, about $1.5 \times 10^6$ cells/mL, about $1.6 \times 10^6$ cells/mL, about $1.7 \times 10^6$ cells/mL, about $1.8 \times 10^6$ cells/mL, about $1.9 \times 10^6$ cells/mL, about $2 \times 10^6$ cells/mL, about $2.2 \times 10^6$ cells/mL, about $2.4 \times 10^6$ cells/mL, about $2.6 \times 10^6$ cells/mL, about $2.8 \times 10^6$ cells/mL, about $3 \times 10^6$ cells/mL, about $3.2 \times 10^6$ cells/mL, about $3.4 \times 10^6$ cells/mL, about $3.6 \times 10^6$ cells/mL, about $3.8 \times 10^6$ cells/mL, about $4 \times 10^6$ cells/mL, about $4.2 \times 10^6$ cells/mL, about $4.4 \times 10^6$ cells/mL, about $4.6 \times 10^6$ cells/mL, about $4.8 \times 10^6$ cells/mL, about $5 \times 10^6$ cells/mL, about $5.5 \times 10^6$ cells/mL, about $6 \times 10^6$ cells/mL, about $6.5 \times 10^6$ cells/mL, about $7 \times 10^6$ cells/mL, about $7.5 \times 10^6$ cells/mL, about $8 \times 10^6$ cells/mL, about $8.5 \times 10^6$ cells/mL, about $9 \times 10^6$ cells/mL, about $9.5 \times 10^6$ cells/mL, about $1 \times 10^7$ cells/mL, about $1.1 \times 10^7$ cells/mL, about $1.2 \times 10^7$ cells/mL, about $1.3 \times 10^7$ cells/mL, about $1.4 \times 10^7$ cells/mL, about $1.5 \times 10^7$ cells/mL, about $1.6 \times 10^7$ cells/mL, about $1.7 \times 10^7$ cells/mL, about $1.8 \times 10^7$ cells/mL, about $1.9 \times 10^7$ cells/mL, about $2 \times 10^7$ cells/mL, about $2.2 \times 10^7$ cells/mL, about $2.4 \times 10^7$ cells/mL, about $2.6 \times 10^7$ cells/mL, about $2.8 \times 10^7$ cells/mL, about $3 \times 10^7$ cells/mL, about $3.2 \times 10^7$ cells/mL, about $3.4 \times 10^7$ cells/mL, about $3.6 \times 10^7$ cells/mL, about $3.8 \times 10^7$ cells/mL, about $4 \times 10^7$ cells/mL, about $4.2 \times 10^7$ cells/mL, about $4.4 \times 10^7$ cells/mL, about $4.6 \times 10^7$ cells/mL, about $4.8 \times 10^7$ cells/mL, about $5 \times 10^7$ cells/mL, about $5.5 \times 10^7$ cells/mL, about $6 \times 10^7$ cells/mL, about $6.5 \times 10^7$ cells/mL, about $7 \times 10^7$ cells/mL, about $7.5 \times 10^7$ cells/mL, about $8 \times 10^7$ cells/mL, about $8.5 \times 10^7$ cells/mL, about $9 \times 10^7$ cells/mL, about $9.5 \times 10^7$ cells/mL, about $1 \times 10^8$ cells/mL, or any integer value in between.

Following cell treatment with PTD-MYC, the treated cells can be centrifuged and resuspended, at a pre-determined concentration (cells/mL). In some embodiments, the cells are resuspended in a suitable freezing medium. In some embodiments, the cell suspension medium is selected from among CHB media, CS10 media, or CS5 media. CHB media is a cell suspension media which contains 50% (v/v) fetal bovine serum (FBS), 40% (v/v) RPMI cell culture media, and 10% (v/v) dimethyl sulfoxide (DMSO). CS10 media (BioLife Solutions, Inc., Bothell, WA) is a cell culture media comprising 10% (v/v) DMSO and is essentially free of animal components or serum. CS5 (BioLife Solutions, Inc.) media is a cell culture media comprising 5% (v/v) DMSO and is essentially free of animal components or serum.

The resuspended PTD-MYC treated cells can then be vialed and cryogenically frozen. The composition comprising the PTD-MYC treated cells can be cryogenically frozen by any method known in the art. For example, composition comprising the PTD-MYC treated cells can be cryogenically frozen by a method that provides controlled cooling to the desired temperature. In some embodiments, composition comprising the PTD-MYC treated immune cells (e.g., PBMC) are cooled using a controlled-rate cryogenic freezer. In some embodiments, composition comprising the PTD-MYC treated immune cells (e.g., PBMC) are cooled at a rate of about −1° C. per min.

In some embodiments, the temperature sufficient to freeze the composition is about −80° C. to about −190° C. In some embodiments, the temperature sufficient to freeze the composition is about −80° C., about −82° C., about −84° C., about −86° C., about −88° C., about −90° C., about −92° C., about −94° C., about −96° C., about −98° C., about −100° C., about −105° C., about −110° C., about −115° C., about −120° C., about −125° C., about −130° C., about −135° C., about −140° C., about −145° C., about −150° C., about −155° C., about −160° C., about −165° C., about −170° C., about −175° C., about −180° C., about −185° C., about −190° C., or any integer value in between.

In some embodiments, the PTD-MYC treated cells are cryogenically frozen via loading into a CoolCell® cell freezing container (BioCision), followed by incubation at −80° C. The CoolCell® provide a cooling rate of about −1° C. per minute. In some embodiments, the TBX-3400 and control cells are cryogenically frozen via loading into a VIA Freeze™ system (GE Healthcare Life Sciences, Pittsburgh, PA) with a cooling rate of −1° C. per minute until the temperature reached −80° C. Following cryopreservation of the cell samples, the samples can be transferred to a liquid nitrogen freezer at −190° C., where the samples can be stored in the vapor phase of the liquid nitrogen.

In some embodiments of the methods provided herein, the one or more immune cells (e.g., PBMCs) isolated from a donor subject can be immediately treated with an anticoagulant following isolation. In some embodiments, the one or more immune cells (e.g., PBMCs) isolated from a donor subject can be immediately treated with the PTD-MYC fusion polypeptide following isolation. In other embodiments, the one or more immune cells isolated from a donor subject can be stored in a suitable buffer prior to treatment with the PTD-MYC fusion polypeptide. In some embodiments, the one or more immune cells isolated from a donor subject can be immediately treated with the PTD-MYC fusion polypeptide following isolation and the treated cells are stored in a suitable buffer prior to freezing.

In some embodiments, the anticoagulant can be one or more of ethylenediaminetetraacetic acid (EDTA), heparin, warfarin, rivaroxaban, dabigatran, apixaban, edoxaban, enoxaparin, fondaparinux, acid citrate dextrose (ACD-A), sodium citrate, oxalate, citrate phosphate double dextrose (CP2D), or any combination thereof.

In some embodiments, the one or more peripheral blood mononuclear cells (PBMC) can be a T-cell, a B-cell, an NK cell, a monocyte, a granulocyte, macrophage, or any combination thereof. In some embodiments, the one or more immune cells isolated from a donor subject can include B cells, T cells, natural killer (NK) cells, myeloid cells, or any combination thereof. In some embodiments, the one or more myeloid cells isolated from a donor subject can include monocytes, macrophages, dendritic cells, eosinophils, neutrophils, mast cells, basophils, granulocytes, or any combination thereof.

In some embodiments, the one or more B cells isolated from a donor subject can include a pre-B cell, a progenitor B cell, an early pro-B cell, a late pro-B cell, a large pre-B cell, a small pre-B cell, an immature B cell, a mature B cell, a naïve B cell, a plasma B cell, an activated B cell, an anergic B cell, a tolerant B cell, a chimeric B cell, an antigen-specific B cell, a memory B cell, a B-1 cell, a B-2 cell, an anergic AN1/T3 cell population, or a combination of two or more thereof.

In some embodiments, the one or more T cells isolated from a donor subject can include naïve T cells, CD4+ T cells, CD8+ T cells, memory T cells, activated T cells, anergic T cells, tolerant T cells, chimeric T cells, and antigen-specific T cells, regulatory T cells, or any combination thereof.

In some embodiments, the method further comprises thawing of the cryopreserved cells, such that the cells exhibit one or more of increased cell viability, increased cell recovery, or increased expression of CD25 after cell activation as compared to control PBMCs not contacted with an effective amount of the MYC fusion polypeptide.

In some embodiments, after thawing of the cryopreserved cells the immune cells can be assessed for viability and or ability to be activated. For example, lymphocytes can be assessed for activation by stimulation or activation by a single agent that induce immune cells activation. In another embodiment, after thawing of the cryopreserved cells the immune cells can be stimulated or activated with two agents, one that induces a primary signal and a second that is a co-stimulatory signal. Ligands useful for stimulating a single signal or stimulating a primary signal and an accessory molecule that stimulates a second signal can be used in soluble form. Ligands can be attached to the surface of a cell, to an Engineered Multivalent Signaling Platform (EMSP), or immobilized on a surface. In a one embodiment both primary and secondary agents are co-immobilized on a surface, for example a bead or a cell. In some embodiments, the molecule providing the activation signal by a single agent can be a CD3 ligand. In some embodiments, the molecule providing the primary activation signal can be a CD3 ligand, and the co-stimulatory molecule can be a CD28 ligand.

In some embodiments, the method further comprises thawing of the cryopreserved cells, such that the cells exhibit one or more of increased cell viability, increased cell recovery, cell activation, or increased expression of CD25 after cell activation as compared to control PBMCs not contacted with an effective amount of the MYC fusion polypeptide.

VI. Immune Cell Banking

In some embodiments, the present disclosure is directed to methods for establishing immune cell banks. As demonstrated by Example 6 (Tables 2 and 3), PBMCs contacted by the MYC fusion polypeptides of present technology were successfully cryopreserved without loss of viability. This facilitates the establishment of cell banks of immune cells that can be stored and used at a later time, thereby offering logistical advantages for immunotherapies, and enabling immune cells to be readily available for adoptive cell transfer.

VII. Kits

Kits according to this embodiment can comprise a carrier means, such as a box, carton, tube, having in close confinement therein one or more containers, such as vials, tubes, ampoules, bottles, syringes, or bags. The kits can also comprise associated instructions for using the MYC-fusion polypeptides, MYC-fusion polypeptide-modified immune cells, and/or the frozen composition of the present technology. In some embodiments, the kit comprises an effective amount of an adoptive cell therapy, such as MYC-fusion polypeptide-modified immune cells. In some embodiments, the kit comprises one for more reagents for the detection of the administered MYC-fusion polypeptides and/or MYC-fusion polypeptide-modified immune cells.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above can also further each include or incorporate the variations of any or all other variations, aspects or embodiments of the present technology.

Example 1: Materials and Methods

Activation of Peripheral Blood Mononuclear Cells (PBMCs). A 24-well plate was coated with a solution of an anti-CD3e antibody (500 µL, 5 µg/mL; BD Biosciences) in sterile DPBS. For control wells, only 500 µL of DPBS was added. The plates were allowed to incubated overnight at 4° C. prior to removing the solutions. Each well was then washed twice with 2 mL of sterile DPBS. Cells were then resuspended in complete RPMI medium (cRPMI) at a concentration of $2 \times 10^6$ cells/mL, and subsequently washed with 1 mL of DPBS. Next, 1.0 mL of the cell suspension was added to each well according to the plate layout. Next, a solution of an anti-CD28 antibody (100 µL, 200 µg/mL; BD Biosciences) was prepared in cRPMI and serially diluted 10-fold to make two stock solutions of the CD28 antibody in cRPMI (20 µg/mL, and 2 µg/mL). Next, 10 µL of the appropriate CD28 antibody solution or DPBS (controls or singly activated cells) was added to the designated wells. Assay plates were then incubated at 37° C., 5% $CO_2$ for 48 or 72 hours, followed by staining with the appropriate antibodies (anti-human CD25-PE, BD Biosciences) for visualization of activated by FACS analysis.

Example 2: Improved Cryopreservation of Immune Cells and/or PBMCs After Treatment with TAT-MYC In this example, a whole blood sample (450-470 mL) was isolated from a human donor subject and mixed with the blood anticoagulant, ethylenediaminetetraacetic acid (EDTA, about 1.5% w/v), After allowing the cells to incubate at least 24 hours at about 20° C., the whole blood sample is then separated into peripheral blood mononuclear cells (PBMCs) and waste (i.e., red blood cells, platelets, plasma, etc.) using a density-gradient solution (DGS) on a SEPAX-100 cell processing system (Biosafe America Inc., Houston, TX). The PBMCs were washed two times during the cell separation process with a 2.5% (w/v) HSA (Human Serum Albumin) solution in saline. Following the wash steps, the PBMCs were resuspended in the 2.5% (w/v) HSA solution at a concentration of $13.6 \times 10^6$ cells/mL to provide a cell suspension.

Following the cell separation process, samples of the PBMCs were taken from the cell suspension prior to treatment (negative control), and the remaining cells in the cell suspension were treated with TAT-MYC fusion protein (25 µg/mL) and incubated at room temperature for 1 hour. The treated PBMCs (called TBX-3400) were then re-washed on the SEPAX-100, and excess TAT-MYC is washed off of the cells with the 2.5% (w/v) HSA solution. Following the final wash step, the TBX-3400 were resuspended in in the 2.5% (w/v) HSA solution at a concentration of $2.7 \times 10^6$ cells/mL.

Following cell treatment with TAT-MYC, the control PBMCs and the TBX-3400 were centrifuged and resuspended, at a pre-determined concentration (cells/mL), in one of three cell suspension mediums: CHB media, CS10 media, or CS5 media. CHB media is a cell suspension media which contains 50% (v/v) fetal bovine serum (FBS), 40% (v/v) RPMI cell culture media, and 10% (v/v) dimethyl sulfoxide (DMSO). CS10 media (BioLife Solutions, Inc.) is a cell culture media comprising 10% (v/v) DMSO and is essentially free of animal components or serum. CS5 media (BioLife Solutions, Inc.) is a cell culture media comprising 5% (v/v) DMSO and is essentially free of animal components or serum.

The resuspended TBX-3400 and control PBMCs were then vialed and cryogenically frozen via one of two methods. In the first method, the cryogenic vials (containing the control PBMCs or TBX-3400) were loaded into a CoolCell® cell freezing container (BioCision), followed by incubation at −80° C. The samples were incubated for 24 hours in the CoolCell® cell freezing containers at −80° C. (which provided a cooling rate of −1° C./min). After freezing, the samples were then stored in the vapor phase of a liquid nitrogen freezer at −190° C. In the second method, the cryogenic vials (containing the control PBMCs or TBX-3400) were loaded into a VIA Freeze™ system (GE Healthcare Life Sciences, Pittsburgh, PA) with a cooling rate of −1° C./min until the temperature reached −80° C. After freezing, the samples were then stored in the vapor phase of a liquid nitrogen freezer at −190° C.

Control PBMC samples were suspended in each of the three media (CHB media, CS10 media, and/or CS5 media) and then split into separate samples to be frozen via the CoolCell® cell freezing container or the VIA Freeze™ system. TBX-3400 samples were suspended in each of the three media (CHB media, CS10 media, and/or CS5 media) and then frozen via the CoolCell® cell freezing container.

Example 3: Improved Cell Viability and Cell Recovery After Thawing Cryopreserved PBMCs Treated with TAT-MYC In this example, the cell viability and recovery of control PBMCs and the TBX-3400 were determined by flow cytometry. Briefly, cell counts were performed before cryopreservation and after thawing the cryopreserved cells. Briefly, frozen and/or cryopreserved cells were quickly thawed in a water bath (37° C.) or a Via Thaw system (GE Healthcare Life Sciences). The thawed cell suspension was then transferred into a 50 mL conical tube, and the cell suspension was diluted drop-wise with cRPMI (for osmotic balancing), then diluted slowly up to about 10 mL to about 30 mL with cRPMI. The cell suspension was then centrifuged at 160-400 RCF for 10 minutes at 20° C., and resuspended in 10 mL of cRPMI. Cells were then incubated at 37° C., 5% $CO_2$ overnight.

To determine cell viability, a sample of the cell suspension containing $1 \times 10^6$ cells/mL was transferred to a microcentrifuge tube and pelleted at 2,000 rpm for 5 minutes. The cell pellet was then resuspended in DPBS and 5 µL of 7-aminoactinomycin D (7-AAD) were added. Following a 10 minute incubation in the dark at room temperature, the samples were analyzed via flow cytometry to determine the cell viability after cryopreservation. FIG. 1 demonstrates that the TBX-3400 exhibits a significant increase in cell viability post-cryopreservation following treatment with the PTD-MYC fusion polypeptide.

Figure 2:
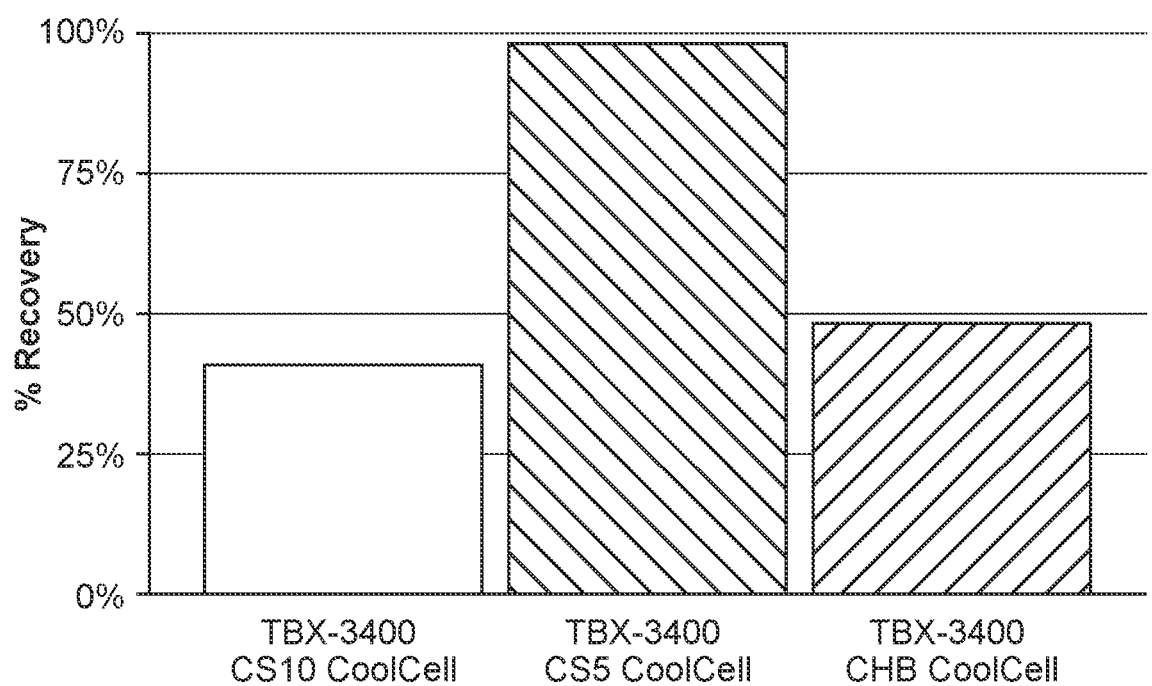
FIG. 2 illustrates the cell recovery (%) of immune cells (PBMC), following pre-treatment with a PTD-MYC fusion polypeptide, cryopreservation under various conditions, and thawing. Cells were frozen in CHB media, CS5 media, or CS10 media as indicated, and frozen in a CoolCell® container.

To determine cell recovery, cell counts were performed with a hemocytometer. Briefly, a sample of the cell suspension containing $1 \times 10^6$ cells/mL was lysed with RBC lysis buffer and allowed to incubate at room temperature. The cell suspensions were then mixed with trypan blue stain (1:1) and the cells were counted with the hemocytometer. FIG. 2 illustrates that the TBX-3400 which were cryopreserved in the CS5 cell suspension medium and frozen using the CoolCell® cell freezing container exhibit about a 95% recovery of viable cells, while TBX-3400 cryopreserved in CHB or CS5 cell suspension mediums demonstrated about 45% and 40% recovery, respectively.

Accordingly, these results demonstrate that the compositions and methods disclosed herein exhibit increased cell viability and/or increased cell recovery as compared to control PBMCs not contacted with an effective amount of the MYC fusion polypeptide.

Example 4: Determination of Cell Populations of Isolated PBMCs after Treatment with TAT-MYC In this example, the populations of isolated peripheral blood mononuclear cells (PBMCs) were determined by flow cytometry. Briefly, a cell suspension containing at least $3 \times 10^6$ cells/mL was centrifuged for 5 min at 1,600 rpm to pellet the cells. The cells were then washed 1× with DPBS and resuspended at a concentration of $1 \times 10^6$ cells/mL. Next, 1 µL/mL of freshly prepared LIVE/DEAD Fixable Near-IR Dead Cell Dye was added to the cell suspension. The dye was prepared by adding 50 µL of DMSO to one vial of LIVE/DEAD Fixable Near-IR Dead Cell Dye (ThermoFisher Scientific, Waltham, MA). The cells were then incubated in the dark at room temperature for about 30 minutes. Following 1× wash with DPBS, the cells were resuspended to a final concentration of 1×10$^6$ cells/mL in 1% BSA or DPBS.

Figure 3:
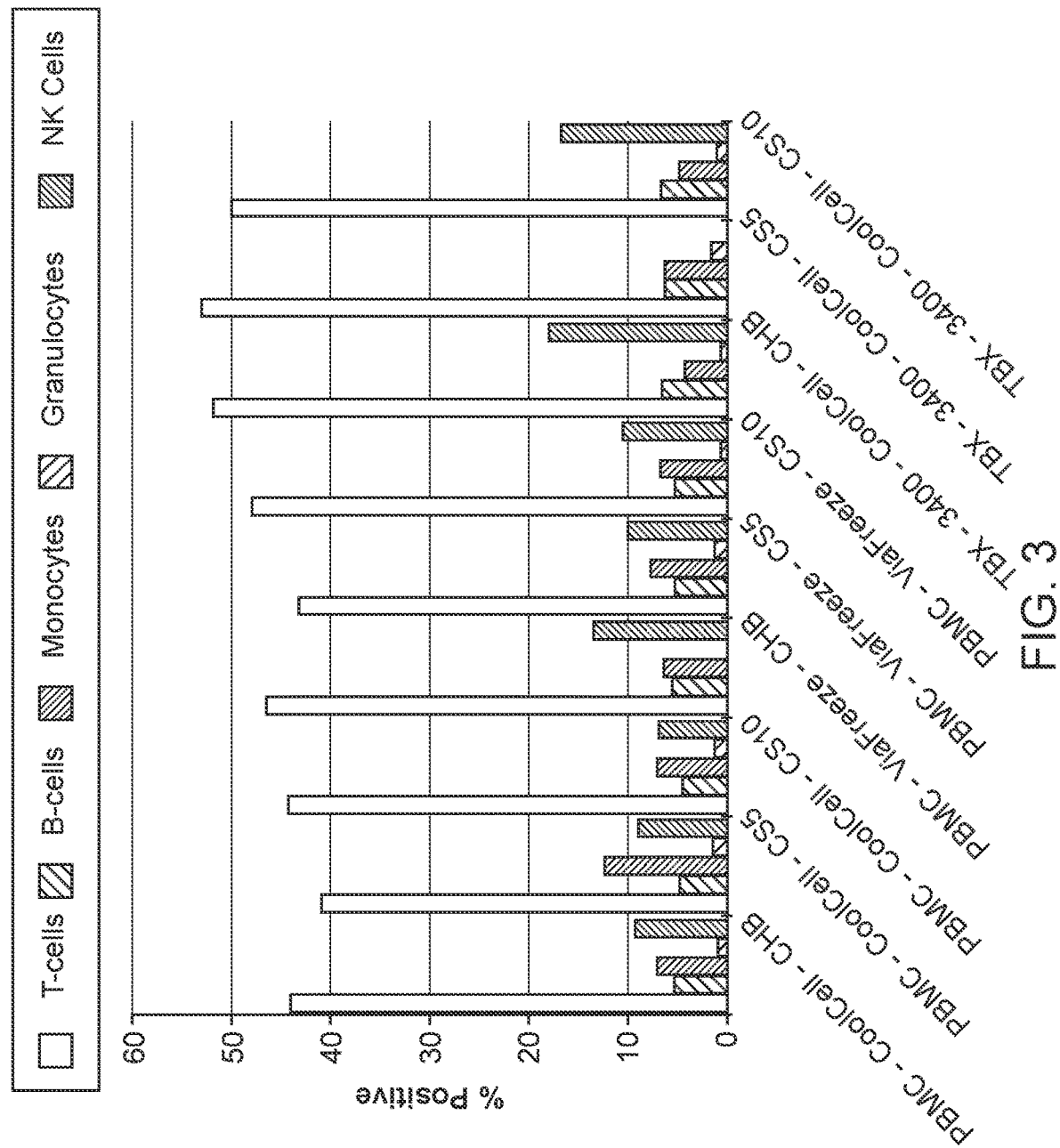
FIG. 3 illustrates the relative amounts of cell populations of immune cells (T-cells, B-cell, monocytes, granulocytes, and NK cells) isolated from donor subjects recovered, following pre-treatment with the PTD-MYC fusion polypeptide or vehicle control, cryopreservation under various conditions, and thawing. Cells were frozen in CHB media, CS5 media, or CS10 media as indicated, and frozen in a CoolCell® container of VIA Freeze™ controlled rate freezer. Cell populations were determined by flow cytometry and immunophenotyping of the various cell populations.

Further, the cell suspension was transferred to three staining tubes and stained with the appropriate antibodies as indicated in Table 1. The staining tubes were then allowed to incubate in the dark for 20 minutes at room temperature. Following incubation, 0.1 mL of an Optilyse B (Beckman Coulter) staining solution were added to each tube, followed by. Following incubation, the samples were analyzed via flow cytometry to determine the populations of PBMCs (FIG. 3).

TABLE 1

Staining with antibodies.

| Tube | Antibody 1 (volume per tube) | Antibody 2 (volume per tube) | Antibody 3 (volume per tube) | Antibody 4 (volume per tube) |
| --- | --- | --- | --- | --- |
| 1 | None | None | None | None |
| 2 | CD45-FITC (20 µL) | CD19-PE (20 µL) | CD3-APC (20 µL) | CD56-PC7 (20 µL) |
| 3 | CD45-FITC (20 µL) | CD15-PE (20 µL) | CD14-APC (20 µL) | None |

Figure 4:
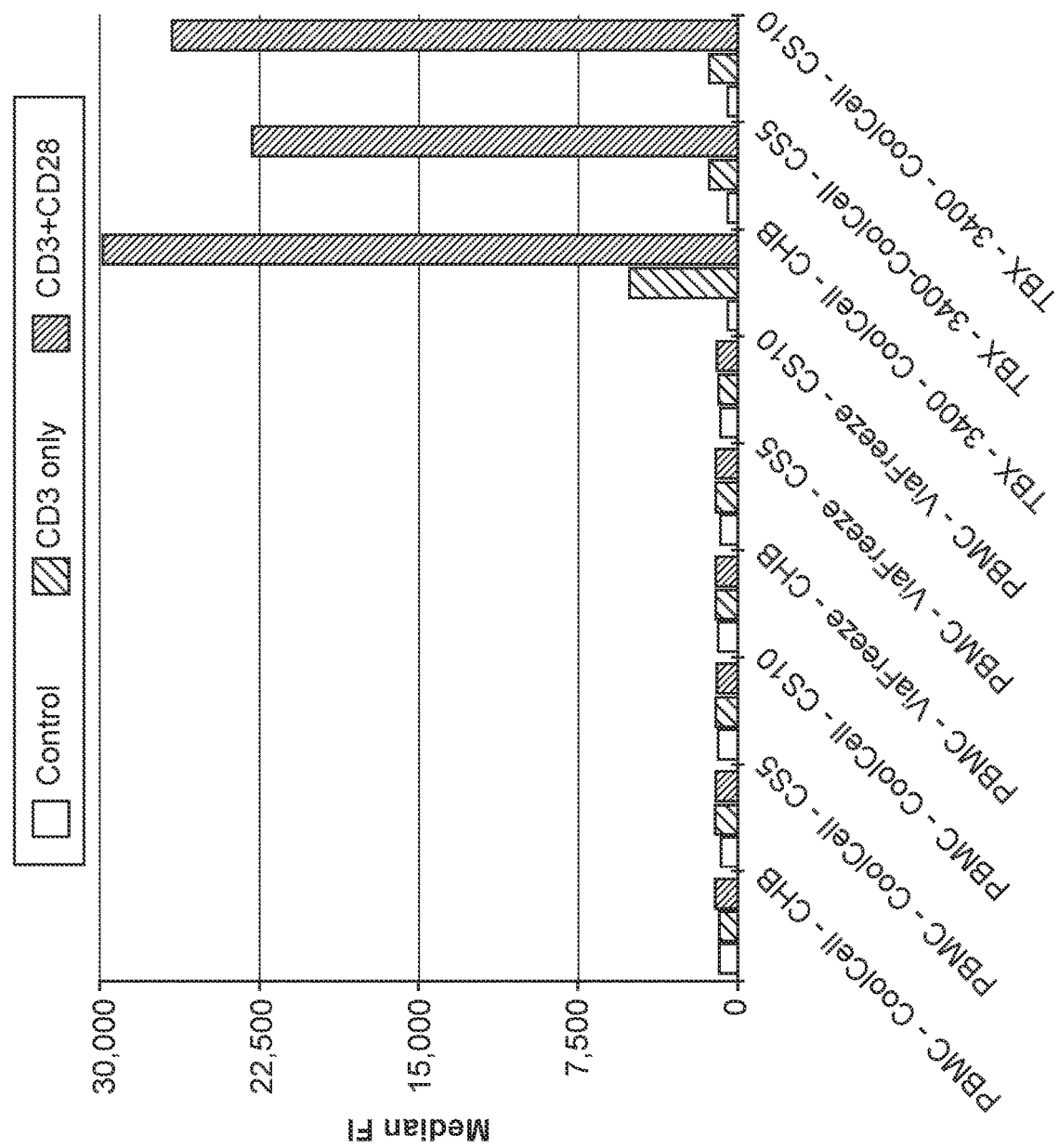
FIG. 4 illustrates cell activation of control cells and immune cells, expressed as median fluoresce intensity (Median FI) for CD25 expression, following pre-treatment with the PTD-MYC fusion polypeptide or vehicle control, cryopreservation under various conditions, and thawing. Cells were frozen in CHB media, CS5 media, or CS10 media as indicated, and frozen in a CoolCell® container of VIA Freeze™ controlled rate freezer. Cells were activated with either a single stimulatory molecule (CD3) alone, or in combination with a co-stimulatory molecule (CD28).

Example 5: Improved Cell Activation After Thawing Cryopreserved Immune Cells and/or PBMCs Treated with TAT-MYC In this example, the cell activation of control PBMCs and the TBX-3400 were determined by flow cytometry with either one activation agent or two co-activating agents. Briefly, following the thawing of cryopreserved control PBMCs or TBX-3400 cells, the cells were suspended in cRPMI at a concentration of 2×10$^6$ cells/mL, and 1 mL of the cell suspension was added to a 24 well plate coated with an anti-CD3 antibody. Further, 10 µL of a CD28 antibody (20 µg/mL) in cRPMI were added to the designated wells, followed by incubation at 37° C., 5% CO$_2$ for 72 hours. Following incubation, the samples were mixed thoroughly and stained with a CD25-FITC antibody. Following incubation, the samples were transferred to a FACS tube and analyzed via flow cytometry to determine the cell activation with CD3 alone, or in combination with CD28 (FIG. 4).

Figure 5:
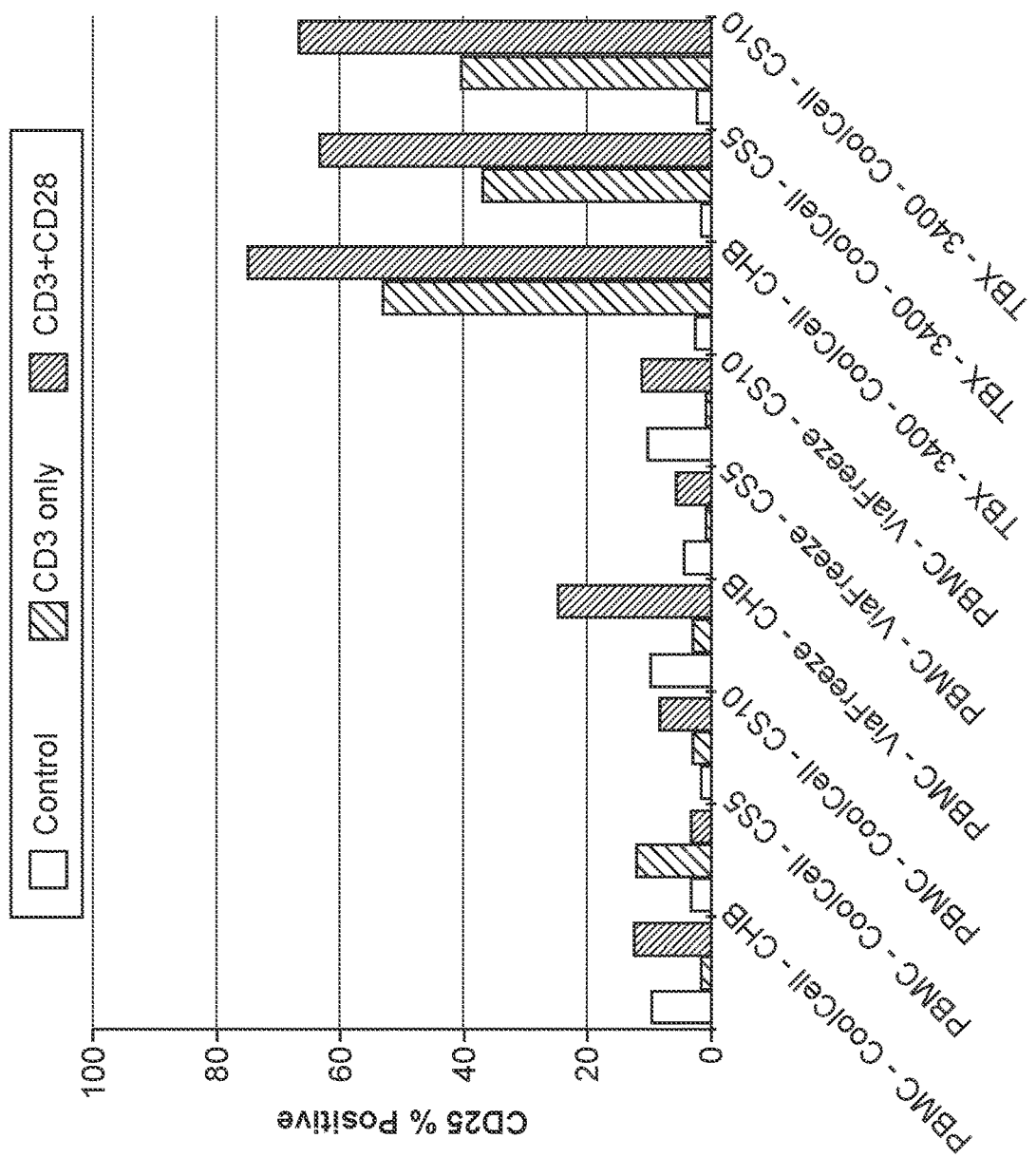
FIG. 5 illustrates cell activation of control cells and immune cells, expressed as % CD25 positive cells, following pre-treatment with the PTD-MYC fusion polypeptide or vehicle control, cryopreservation under various conditions, and thawing. Cells were frozen in CHB media, CS5 media, or CS10 media as indicated, and frozen in a CoolCell® container of VIA Freeze™ controlled rate freezer. Cells were activated with either a single stimulatory molecule (CD3) alone, or in combination with a co-stimulatory molecule (CD28).

Further, the fraction of CD25 positive cells was determined after cell activation of control PBMCs and the TBX-3400 by flow cytometry with either one activation agent or two co-activating agents. Following cell activation with CD3 and/or CD28, the samples were mixed thoroughly and stained with CD25-FITC (Beckman Coulter). FIG. 5 illustrates the fraction of CD25 positive cells as determined by flow cytometry after cell activation of control PBMCs and the TBX-3400 which have been previously cryogenically frozen and subsequently thawed.

Accordingly, these results demonstrate that the compositions and methods disclosed herein exhibit increased cell activation and/or increased expression of CD25 after cell activation as compared to control PBMCs not contacted with an effective amount of the MYC fusion polypeptide.

Example 6: Stability of PBMCs Treated with TAT-MYC

In this example, the stability of TBX-3400 was determined by flow cytometry. Total nucleated cell (TNC) counts and viability were measured pre-freeze/pre-cryopreservation and post-thaw for five different PBMC batches stored at either ≤−70° C. or ≤−150° C. for storage times ranging from 24 hours (24 h) to 42 days (42 d). Briefly, frozen and/or cryopreserved cells were quickly thawed in a water bath (37° C.) or a Via Thaw system (GE Healthcare Life Sciences). The thawed cell suspension was then transferred into a 50 mL conical tube, and the cell suspension was diluted drop-wise with cRPMI (for osmotic balancing), then diluted slowly up to about 10 mL to about 30 mL with cRPMI. The cell suspension was then centrifuged at 160-400 RCF for 10 minutes at 20° C., and resuspended in 10 mL of cRPMI. Cells were then incubated at 37° C., 5% CO$_2$ overnight.

To determine cell viability, a sample of the cell suspension containing 1×10$^6$ cells/mL was transferred to a microcentrifuge tube and pelleted at 2,000 rpm for 5 minutes. The cell pellet was then resuspended in DPBS and 54, of 7-aminoactinomycin D (7-AAD) were added. Following a 10 minute incubation in the dark at room temperature, the samples were analyzed via flow cytometry to determine the cell viability after cryopreservation.

Cell counts were performed with a hemocytometer. Briefly, a sample of the cell suspension containing 1×10$^6$ cells/mL was lysed with RBC lysis buffer and allowed to incubate at room temperature. The cell suspensions were then mixed with trypan blue stain (1:1) and the cells were counted with the hemocytometer.

As shown in Table 2, the MYC fusion polypeptide of the present technology is effective as a cryoprotectant for long-term storage of PBMCs, and, as shown in Table 3, the MYC fusion polypeptide is effective in maintaining the post-thaw stability of PBMCs at ambient temperature. The duration of storage had no effect on the recoveries of TNCs or TNC viability (Table 2)

TABLE 2

Cryopreserved TBX-3400 Stability.

| Batch | Manufacture Date | Storage Conditions | Study Initiation Date | Storage Time | Pre-Freeze % viability | Post-Thaw % viability | Pre-Freeze TNC Counts (live) | Post-Thaw TNC Counts (live) |
| --- | --- | --- | --- | --- | --- | --- | --- | --- |
| 081919 | 20 Aug. 2019 | ≤−70° C. | 21 Aug. 2019 | 24 h | 91.8 | 88.6 | 8.33E+06 | 8.33E+06 |
| 081919 | 20 Aug. 2019 | ≤−150° C. | 23 Aug. 2019 | 72 h | 91.8 | 87.5 | 8.33E+06 | 7.21E+06 |
| 082119 | 22 Aug. 2019 | ≤−70° C. | 23 Aug. 2019 | 24 h | 75.9 | 78.6 | 6.87E+06 | 7.13E+06 |
| 082819 | 20 Aug. 2019 | ≤−150° C. | 10 Oct. 2019 | 42 d | 89.7 | 89.5 | 3.46E+07 | 3.68E+07 |

TABLE 2-continued

Cryopreserved TBX-3400 Stability.

| Batch | Manufacture Date | Storage Conditions | Study Initiation Date | Storage Time | Pre-Freeze % viability | Post-Thaw % viability | Pre-Freeze TNC Counts (live) | Post-Thaw TNC Counts (live) |
|---|---|---|---|---|---|---|---|---|
| 091119 | 12 Sep. 2019 | ≤−150° C. | 10 Oct. 2019 | 28 d | 83.6 | 79.9 | 2.54E+07 | 2.06E+07 |
| 092519 | 26 Sep. 2019 | ≤−150° C. | 10 Oct. 2019 | 14 d | 85.6 | 83.9 | 3.64E+07 | 3.40E+07 |

TABLE 3

Cryopreserved TBX-3400 Stability-Post-Thaw Stability at Ambient Temperature

| Batch | Manufacture Date | Storage Conditions | Study Initiation Date | Time | Post-Thaw % viability t = 0 | Post-Thaw % viability t = 2 h | Post-Thaw % viability t = 4 h | Post-Thaw TNC Counts (live) t = 0 | Post-Thaw TNC Counts (live) t = 2 h | Post-Thaw TNC Counts (live) t = 4 h |
|---|---|---|---|---|---|---|---|---|---|---|
| 081919 | 20 Aug. 2019 | ≤−70° C. | 21 Aug. 2019 | 24 h | 88.6 | 87.0 | 86.7 | 8.33E+06 | 7.62E+06 | 5.83E+06 |

Accordingly, these results demonstrate that the compositions disclosed herein are useful in methods for long-term storage of immune cells and in methods for immune cell banking.

What is claimed is:

1. A cryogenically frozen composition comprising:
   (a) a MYC fusion polypeptide, comprising (i) a protein transduction domain; (ii) a MYC polypeptide sequence; and
   (b) one or more peripheral blood mononuclear cells (PBMCs) isolated from a donor subject;
   wherein the composition exhibits increased cell viability when thawed as compared to control PBMCs in the absence of the MYC fusion polypeptide after a freeze-thaw cycle.

2. The cryogenically frozen composition of claim 1, wherein the protein transduction domain sequence is a TAT protein transduction domain sequence.

3. The cryogenically frozen composition of claim 1, wherein the MYC fusion polypeptide comprises SEQ ID NO: 1.

4. The cryogenically frozen composition of claim 1, wherein the one or more peripheral blood mononuclear cells comprises a T-cell, a B-cell, an NK cell, a monocyte, a granulocyte, a macrophage, or any combination thereof.

5. The cryogenically frozen composition of claim 1, further comprising a cell suspension medium.

6. The cryogenically frozen composition of claim 5, wherein the cell suspension medium comprises CHB media, CS5 media, or CS10 media.

7. The cryogenically frozen composition of claim 1 wherein the composition exhibits increased cell recovery when thawed as compared to control PBMCs in the absence of the MYC fusion polypeptide after a freeze-thaw cycle.

8. The cryogenically frozen composition of claim 1, wherein the composition exhibits increased expression of CD25 after cell activation as compared to control PBMCs in the absence of the MYC fusion polypeptide after a freeze-thaw cycle.

9. A method of cryopreserving peripheral blood mononuclear cells (PBMCs), comprising:
   (a) contacting a composition comprising one or more PBMCs isolated from a donor subject with an effective amount of a MYC fusion polypeptide, comprising (i) a protein transduction domain; (ii) a MYC polypeptide sequence; and
   (b) cooling the PBMCs to a temperature sufficient to freeze the composition.

10. The method of claim 9, wherein the protein transduction domain sequence is a TAT protein transduction domain sequence.

11. The method of claim 9, wherein the MYC fusion polypeptide comprises SEQ ID NO: 1.

12. The method of claim 9, wherein the one or more peripheral blood mononuclear cells comprises a T-cell, a B-cell, an NK cell, a monocyte, a granulocyte, or any combination thereof.

13. The method of claim 9, further comprising suspending the PBMCs in a cell suspension medium.

14. The method of claim 13, wherein the cell suspension medium comprises CHB media, CS5 media, or CS10 media.

15. The method of claim 9, wherein the composition comprising one or more PBMCs is contacted with the MYC fusion polypeptide at a concentration of about 0.5 µg/mL to about 500 µg/mL.

16. The method of claim 9, wherein the composition comprising one or more PBMCs is contacted with the MYC fusion polypeptide at a concentration of about 0.5 µg/mL to about 10 g/mL.

17. The method of claim 9, wherein the composition comprising one or more PBMCs is contacted with the MYC fusion polypeptide for less than 24 hours prior to step (b).

18. The method of claim 9, wherein the composition comprising one or more PBMCs is contacted with the MYC fusion polypeptide for about 1 hour prior to step (b).

19. The method of claim 9, wherein the PBMCs are washed following step (a) and prior to step (b).

20. The method of claim 9, wherein the PBMCs are cooled using a controlled-rate cryogenic freezer.

21. The method of claim 9, wherein the PBMCs are cooled at a rate of about −1° C. per min.

22. The method of claim 9, wherein the temperature sufficient to freeze the composition is about −80° C. to about −190° C.

23. The method of claim 9, further comprising thawing of the cryopreserved cells, such that the cells exhibit one or more of increased cell viability, increased cell recovery, cell activation, or increased expression of CD25 after cell activation as compared to control PBMCs not contacted with an effective amount of the MYC fusion polypeptide.

24. An immune cell bank comprising the cryogenically frozen composition of claim 1.

* * * * *

```
                        SEQUENCE LISTING

<160> NUMBER OF SEQ ID NOS: 13

<210> SEQ ID NO 1
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Lys Lys Arg Arg Gln Arg Arg Pro Leu Asn Val Ser Phe
1               5                   10                  15

Thr Asn Arg Asn Tyr Asp Leu Asp Tyr Asp Ser Val Gln Pro Tyr Phe
                20                  25                  30

Tyr Cys Asp Glu Glu Glu Asn Phe Tyr Gln Gln Gln Gln Ser Glu
        35                  40                  45

Leu Gln Pro Pro Ala Pro Ser Glu Asp Ile Trp Lys Lys Phe Glu Leu
    50                  55                  60

Leu Pro Thr Pro Pro Leu Ser Pro Ser Arg Arg Ser Gly Leu Cys Ser
65                  70                  75                  80

Pro Ser Tyr Val Ala Val Thr Pro Phe Ser Leu Arg Gly Asp Asn Asp
                85                  90                  95

Gly Gly Gly Gly Ser Phe Ser Thr Ala Asp Gln Leu Glu Met Val Thr
            100                 105                 110

Glu Leu Leu Gly Gly Asp Met Val Asn Gln Ser Phe Ile Cys Asp Pro
        115                 120                 125

Asp Asp Glu Thr Phe Ile Lys Asn Ile Ile Ile Gln Asp Cys Met Trp
    130                 135                 140
```

-continued

```
Ser Gly Phe Ser Ala Ala Lys Leu Val Ser Glu Lys Leu Ala Ser
145                 150                 155                 160

Tyr Gln Ala Ala Arg Lys Asp Ser Gly Ser Pro Asn Pro Ala Arg Gly
                165                 170                 175

His Ser Val Cys Ser Thr Ser Ser Leu Tyr Leu Gln Asp Leu Ser Ala
            180                 185                 190

Ala Ala Ser Glu Cys Ile Asp Pro Ser Val Val Phe Pro Tyr Pro Leu
        195                 200                 205

Asn Asp Ser Ser Ser Pro Lys Ser Cys Ala Ser Gln Asp Ser Ser Ala
    210                 215                 220

Phe Ser Pro Ser Ser Asp Ser Leu Leu Ser Ser Thr Glu Ser Ser Pro
225                 230                 235                 240

Gln Gly Ser Pro Glu Pro Leu Val Leu His Glu Glu Thr Pro Pro Thr
                245                 250                 255

Thr Ser Ser Asp Ser Glu Glu Glu Gln Glu Asp Glu Glu Ile Asp
            260                 265                 270

Val Val Ser Val Glu Lys Arg Gln Ala Pro Gly Lys Arg Ser Glu Ser
        275                 280                 285

Gly Ser Pro Ser Ala Gly Gly His Ser Lys Pro Pro His Ser Pro Leu
290                 295                 300

Val Leu Lys Arg Cys His Val Ser Thr His Gln His Asn Tyr Ala Ala
305                 310                 315                 320

Pro Pro Ser Thr Arg Lys Asp Tyr Pro Ala Ala Lys Arg Val Lys Leu
                325                 330                 335

Asp Ser Val Arg Val Leu Arg Gln Ile Ser Asn Asn Arg Lys Cys Thr
            340                 345                 350

Ser Pro Arg Ser Ser Asp Thr Glu Glu Asn Val Lys Arg Arg Thr His
        355                 360                 365

Asn Val Leu Glu Arg Gln Arg Arg Asn Glu Leu Lys Arg Ser Phe Phe
    370                 375                 380

Ala Leu Arg Asp Gln Ile Pro Glu Leu Glu Asn Asn Glu Lys Ala Pro
385                 390                 395                 400

Lys Val Val Ile Leu Lys Lys Ala Thr Ala Tyr Ile Leu Ser Val Gln
                405                 410                 415

Ala Glu Glu Gln Lys Leu Ile Ser Glu Glu Asp Leu Leu Arg Lys Arg
            420                 425                 430

Arg Glu Gln Leu Lys His Lys Leu Glu Gln Leu Arg Lys Gly Glu Leu
        435                 440                 445

Asn Ser Lys Leu Glu Gly Lys Pro Ile Pro Asn Pro Leu Leu Gly Leu
450                 455                 460

Asp Ser Thr Arg Thr Gly His His His His His
465                 470                 475

<210> SEQ ID NO 2
<211> LENGTH: 439
<212> TYPE: PRT
<213> ORGANISM: Homo sapiens

<400> SEQUENCE: 2

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
                20                  25                  30

Gln Gln Gln Gln Gln Ser Glu Leu Gln Pro Pro Ala Pro Ser Glu Asp
```

```
                    35                  40                  45
Ile Trp Lys Lys Phe Glu Leu Leu Pro Thr Pro Pro Leu Ser Pro Ser
 50                  55                  60

Arg Arg Ser Gly Leu Cys Ser Pro Ser Tyr Val Ala Val Thr Pro Phe
 65                  70                  75                  80

Ser Leu Arg Gly Asp Asn Asp Gly Gly Gly Ser Phe Ser Thr Ala
                 85                  90                  95

Asp Gln Leu Glu Met Val Thr Glu Leu Leu Gly Gly Asp Met Val Asn
                100                 105                 110

Gln Ser Phe Ile Cys Asp Pro Asp Glu Thr Phe Ile Lys Asn Ile
            115                 120                 125

Ile Ile Gln Asp Cys Met Trp Ser Gly Phe Ser Ala Ala Lys Leu
        130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
            180                 185                 190

Val Val Phe Pro Tyr Pro Leu Asn Asp Ser Ser Pro Lys Ser Cys
        195                 200                 205

Ala Ser Gln Asp Ser Ser Ala Phe Ser Pro Ser Ser Asp Ser Leu Leu
210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
            275                 280                 285

Lys Pro Pro His Ser Pro Leu Val Leu Lys Arg Cys His Val Ser Thr
290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
            355                 360                 365

Glu Leu Lys Arg Ser Phe Phe Ala Leu Arg Asp Gln Ile Pro Glu Leu
            370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
            435

<210> SEQ ID NO 3
```

<211> LENGTH: 450
<212> TYPE: PRT
<213> ORGANISM: Homo sapiens

<400> SEQUENCE: 3

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
```

```
                385                 390                 395                 400
Asn Asn Glu Lys Ala Pro Lys Val Val Ile Leu Lys Lys Ala Thr Ala
                    405                 410                 415
Tyr Ile Leu Ser Val Gln Ala Glu Glu Gln Lys Leu Ile Ser Glu Glu
                    420                 425                 430
Asp Leu Leu Arg Lys Arg Arg Glu Gln Leu Lys His Lys Leu Glu Gln
                    435                 440                 445
Leu Arg
    450

<210> SEQ ID NO 4
<211> LENGTH: 434
<212> TYPE: PRT
<213> ORGANISM: Homo sapiens

<400> SEQUENCE: 4

Pro Leu Asn Val Ser Phe Thr Asn Arg Asn Tyr Asp Leu Asp Tyr Asp
1               5                   10                  15
Ser Val Gln Pro Tyr Phe Tyr Cys Asp Glu Glu Asn Phe Tyr Gln
            20                  25                  30
Gln Gln Gln Gln Ser Glu Leu Gln Pro Pro Ala Pro Ser Glu Asp Ile
        35                  40                  45
Trp Lys Lys Phe Glu Leu Leu Pro Thr Pro Pro Leu Ser Pro Ser Arg
    50                  55                  60
Arg Ser Gly Leu Cys Ser Pro Ser Tyr Val Ala Val Thr Pro Phe Ser
65                  70                  75                  80
Leu Arg Gly Asp Asn Asp Gly Gly Gly Gly Ser Phe Ser Thr Ala Asp
                85                  90                  95
Gln Leu Glu Met Val Thr Glu Leu Leu Gly Gly Asp Met Val Asn Gln
            100                 105                 110
Ser Phe Ile Cys Asp Pro Asp Asp Glu Thr Phe Ile Lys Asn Ile Ile
        115                 120                 125
Ile Gln Asp Cys Met Trp Ser Gly Phe Ser Ala Ala Ala Lys Leu Val
    130                 135                 140
Ser Glu Lys Leu Ala Ser Tyr Gln Ala Ala Arg Lys Asp Ser Gly Ser
145                 150                 155                 160
Pro Asn Pro Ala Arg Gly His Ser Val Cys Ser Thr Ser Ser Leu Tyr
                165                 170                 175
Leu Gln Asp Leu Ser Ala Ala Ala Ser Glu Cys Ile Asp Pro Ser Val
            180                 185                 190
Val Phe Pro Tyr Pro Leu Asn Asp Ser Ser Ser Pro Lys Ser Cys Ala
        195                 200                 205
Ser Gln Asp Ser Ser Ala Phe Ser Pro Ser Ser Asp Ser Leu Leu Ser
    210                 215                 220
Ser Thr Glu Ser Ser Pro Gln Gly Ser Pro Glu Pro Leu Val Leu His
225                 230                 235                 240
Glu Glu Thr Pro Pro Thr Thr Ser Ser Asp Ser Glu Glu Glu Gln Glu
                245                 250                 255
Asp Glu Glu Glu Ile Asp Val Val Ser Val Glu Lys Arg Gln Ala Pro
            260                 265                 270
Gly Lys Arg Ser Glu Ser Gly Ser Pro Ser Ala Gly Gly His Ser Lys
        275                 280                 285
Pro Pro His Ser Pro Leu Val Leu Lys Arg Cys His Val Ser Thr His
    290                 295                 300
```

```
Gln His Asn Tyr Ala Ala Pro Pro Ser Thr Arg Lys Asp Tyr Pro Ala
305                 310                 315                 320

Ala Lys Arg Val Lys Leu Asp Ser Val Arg Val Leu Arg Gln Ile Ser
                325                 330                 335

Asn Asn Arg Lys Cys Thr Ser Pro Arg Ser Ser Asp Thr Glu Glu Asn
                340                 345                 350

Val Lys Arg Arg Thr His Asn Val Leu Glu Arg Gln Arg Arg Asn Glu
                355                 360                 365

Leu Lys Arg Ser Phe Phe Ala Leu Arg Asp Gln Ile Pro Glu Leu Glu
            370                 375                 380

Asn Asn Glu Lys Ala Pro Lys Val Val Ile Leu Lys Lys Ala Thr Ala
385                 390                 395                 400

Tyr Ile Leu Ser Val Gln Ala Glu Glu Gln Lys Leu Ile Ser Glu Glu
                405                 410                 415

Asp Leu Leu Arg Lys Arg Arg Glu Gln Leu Lys His Lys Leu Glu Gln
                420                 425                 430

Leu Arg

<210> SEQ ID NO 5
<211> LENGTH: 67
<212> TYPE: PRT
<213> ORGANISM: Homo sapiens

<400> SEQUENCE: 5

Glu Leu Lys Arg Ser Phe Phe Ala Leu Arg Asp Gln Ile Pro Glu Leu
1               5                   10                  15

Glu Asn Asn Glu Lys Ala Pro Lys Val Val Ile Leu Lys Lys Ala Thr
            20                  25                  30

Ala Tyr Ile Leu Ser Val Gln Ala Glu Glu Gln Lys Leu Ile Ser Glu
        35                  40                  45

Glu Asp Leu Leu Arg Lys Arg Arg Glu Gln Leu Lys His Lys Leu Glu
    50                  55                  60

Gln Leu Arg
65

<210> SEQ ID NO 6
<211> LENGTH: 14
<212> TYPE: PRT
<213> ORGANISM: Unknown
<220> FEATURE:
<223> OTHER INFORMATION: Description of Unknown:
      E-box DNA binding domain

<400> SEQUENCE: 6

Lys Arg Arg Thr His Asn Val Leu Glu Arg Gln Arg Arg Asn
1               5                   10

<210> SEQ ID NO 7
<211> LENGTH: 10
<212> TYPE: PRT
<213> ORGANISM: Human immunodeficiency virus 1

<400> SEQUENCE: 7

Met Arg Lys Lys Arg Arg Gln Arg Arg Arg
1               5                   10

<210> SEQ ID NO 8
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Lys Pro Ile Pro Asn Pro Leu Leu Gly Leu Asp Ser Thr
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Pro Asn Pro Leu Leu Gly Leu Asp
1               5

<210> SEQ ID NO 11
<211> LENGTH: 454
<212> TYPE: PRT
<213> ORGANISM: Homo sapiens

<400> SEQUENCE: 11

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
```

```
            180                 185                 190
Leu Gln Asp Leu Ser Ala Ala Ala Ser Glu Cys Ile Asp Pro Ser Val
            195                 200                 205

Val Phe Pro Tyr Pro Leu Asn Asp Ser Ser Pro Lys Ser Cys Ala
        210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Gly Glu Leu Asn Ser Lys Leu Glu
1               5

<210> SEQ ID NO 13
<211> LENGTH: 9
<212> TYPE: PRT
<213> ORGANISM: Human immunodeficiency virus 1

<400> SEQUENCE: 13

Arg Lys Lys Arg Arg Gln Arg Arg Arg
1               5
```